United States Patent
Berdahl et al.

(10) Patent No.: US 10,842,376 B2
(45) Date of Patent: Nov. 24, 2020

(54) EYE-RELATED INTRABODY PRESSURE IDENTIFICATION AND MODIFICATION

(71) Applicant: Equinox Ophthalmic, Inc., Sioux Falls, SD (US)

(72) Inventors: John Berdahl, Sioux Falls, SD (US); George Tsai, Mission Viejo, CA (US); Vance Michael Thompson, Sioux Falls, SD (US)

(73) Assignee: Equinox Ophthalmic, Inc., Sioux Falls, SD (US)

(*) Notice: Subject to any disclaimer, the term of this patent is extended or adjusted under 35 U.S.C. 154(b) by 336 days.

(21) Appl. No.: 15/754,723

(22) PCT Filed: Aug. 25, 2016

(86) PCT No.: PCT/US2016/048784
§ 371 (c)(1),
(2) Date: Feb. 23, 2018

(87) PCT Pub. No.: WO2017/035406
PCT Pub. Date: Mar. 2, 2017

(65) Prior Publication Data
US 2018/0279877 A1 Oct. 4, 2018

Related U.S. Application Data

(60) Provisional application No. 62/311,052, filed on Mar. 21, 2016, provisional application No. 62/210,751, filed on Aug. 27, 2015.

(51) Int. Cl.
*A61B 5/00* (2006.01)
*A61B 3/16* (2006.01)
(Continued)

(52) U.S. Cl.
CPC .............. *A61B 3/165* (2013.01); *A61B 3/102* (2013.01); *A61B 3/12* (2013.01); *A61B 3/1241* (2013.01);
(Continued)

(58) Field of Classification Search
CPC ........... A61B 3/165; A61B 3/102; A61B 3/12; A61B 3/1241; A61B 3/14; A61B 5/031;
(Continued)

(56) References Cited

U.S. PATENT DOCUMENTS 2,555,636 A 6/1951 Felts et al.
4,305,399 A 12/1981 Beale
(Continued)

FOREIGN PATENT DOCUMENTS

AU 2016311449 1/2019
CN 102264277 11/2011
(Continued)

OTHER PUBLICATIONS

"U.S. Appl. No. 15/688,016, Non Final Office Action dated Oct. 5, 2018", 12 pgs.
(Continued)

*Primary Examiner* — Max F Hinderburg
(74) *Attorney, Agent, or Firm* — Schwegman Lundberg & Woessner, P.A.

(57) ABSTRACT

An apparatus for at least one of diagnosing or treating an eye condition can include a goggle enclosure, sized and shaped to be seated on an eye socket of an eye to provide one or more cavities within the enclosure that extend about an entire exposed anterior portion of the eye, a pump, in fluidic communication with the one or more cavities to apply a fluid pressure to the one or more cavities, the pump configured to adjust a fluid pressure within the one or more cavities of the goggle enclosure, and a control circuit, including a data
(Continued)

interface to receive data directly or indirectly indicating at least one of an intraorbital pressure, ICP, IOP, or a relationship between ICP and IOP, and based on processing the received data as a feedback control variable, controlling the pump to adjust the fluid pressure within the one or more cavities, the controlling including using further monitoring of the received data to control the pump.

25 Claims, 19 Drawing Sheets

(51) Int. Cl.

| | |
|---|---|
| A61B 5/03 | (2006.01) |
| A61B 3/12 | (2006.01) |
| A61B 3/10 | (2006.01) |
| A61B 3/14 | (2006.01) |
| A61B 5/0205 | (2006.01) |
| A61B 6/00 | (2006.01) |
| A61B 8/10 | (2006.01) |
| A61H 9/00 | (2006.01) |
| A61B 5/021 | (2006.01) |
| A61B 5/024 | (2006.01) |
| A61B 5/11 | (2006.01) |
| A61B 5/145 | (2006.01) |
| A61B 5/026 | (2006.01) |
| A61B 5/055 | (2006.01) |
| A61B 5/103 | (2006.01) |
| A61B 5/107 | (2006.01) |

(52) U.S. Cl.
CPC ............... *A61B 3/14* (2013.01); *A61B 3/16* (2013.01); *A61B 5/0205* (2013.01); *A61B 5/031* (2013.01); *A61B 5/6803* (2013.01); *A61B 5/6898* (2013.01); *A61B 6/50* (2013.01); *A61B 8/10* (2013.01); *A61H 9/0071* (2013.01); *A61B 5/0077* (2013.01); *A61B 5/021* (2013.01); *A61B 5/024* (2013.01); *A61B 5/026* (2013.01); *A61B 5/055* (2013.01); *A61B 5/1032* (2013.01); *A61B 5/1077* (2013.01); *A61B 5/1116* (2013.01); *A61B 5/14542* (2013.01); *A61B 2562/0261* (2013.01); *A61H 2201/501* (2013.01); *A61H 2201/5071* (2013.01); *A61H 2205/024* (2013.01); *A61H 2230/208* (2013.01); *A61H 2230/255* (2013.01); *A61H 2230/305* (2013.01); *A61H 2230/625* (2013.01); *A61H 2230/855* (2013.01)

(58) Field of Classification Search
CPC .... A61B 5/0205; A61B 5/6803; A61B 5/6898
See application file for complete search history.

(56) References Cited

U.S. PATENT DOCUMENTS

| | | | |
|---|---|---|---|
| 4,387,707 A | 6/1983 | Polikoff | |
| 4,724,843 A | 2/1988 | Fisher | |
| 4,907,595 A | 3/1990 | Strauss | |
| 5,201,312 A * | 4/1993 | Schenck | A61B 3/125 324/318 |
| 5,523,808 A | 6/1996 | Kohayakawa | |
| 5,601,548 A | 2/1997 | Smith et al. | |
| 5,625,426 A | 4/1997 | Liu | |
| 5,927,281 A | 7/1999 | Monteleone et al. | |
| 5,951,477 A | 9/1999 | Ragaluskals et al. | |
| 6,093,147 A | 7/2000 | Kontiola | |
| 6,129,682 A | 10/2000 | Borchert et al. | |
| 6,307,302 B1 | 10/2001 | Toda | |
| 6,673,014 B2 | 1/2004 | Badchi et al. | |
| 6,814,966 B1 | 11/2004 | Wax et al. | |
| 7,122,007 B2 | 10/2006 | Querfurth | |
| 7,137,952 B2 | 11/2006 | Leonardi | |
| 7,331,666 B2 | 2/2008 | Swab et al. | |
| 7,512,436 B2 | 3/2009 | Petty et al. | |
| 8,408,204 B2 | 4/2013 | Lurie | |
| 8,939,906 B2 | 1/2015 | Huang et al. | |
| 8,998,810 B2 | 4/2015 | Kontiola et al. | |
| 9,125,724 B2 | 9/2015 | Berdahl et al. | |
| 9,173,564 B2 | 11/2015 | Choo et al. | |
| 9,498,380 B2 | 11/2016 | Berdahl et al. | |
| 10,154,926 B1 | 12/2018 | Berdahl et al. | |
| 10,709,605 B1 | 7/2020 | Berdahl et al. | |
| 2002/0193675 A1* | 12/2002 | Rathjen | A61B 3/16 600/405 |
| 2003/0078486 A1 | 4/2003 | Klein et al. | |
| 2003/0088260 A1 | 5/2003 | Smedley et al. | |
| 2004/0111050 A1 | 6/2004 | Smedley et al. | |
| 2004/0237969 A1 | 12/2004 | Fuller | |
| 2007/0123796 A1 | 5/2007 | Lenhardt et al. | |
| 2007/0161875 A1* | 7/2007 | Epley | A61B 5/11 600/301 |
| 2007/0282405 A1 | 12/2007 | Wong, Jr. et al. | |
| 2008/0086048 A1 | 4/2008 | Dupps, Jr. et al. | |
| 2008/0171953 A1 | 7/2008 | Mische | |
| 2008/0221613 A1 | 9/2008 | Taske | |
| 2009/0043365 A1 | 2/2009 | Friedland et al. | |
| 2009/0306493 A1 | 12/2009 | Kontiola | |
| 2010/0056935 A1 | 3/2010 | McKinley et al. | |
| 2011/0022010 A1 | 1/2011 | Grenon et al. | |
| 2011/0071458 A1 | 3/2011 | Rickard | |
| 2011/0137182 A1 | 6/2011 | Bellezza et al. | |
| 2012/0222201 A1 | 9/2012 | Dondero | |
| 2013/0041245 A1 | 2/2013 | Cerboni | |
| 2013/0072828 A1 | 3/2013 | Sweis et al. | |
| 2013/0141690 A1 | 6/2013 | Taylor et al. | |
| 2013/0144185 A1 | 6/2013 | Fuller et al. | |
| 2013/0211285 A1 | 8/2013 | Fuller et al. | |
| 2013/0215376 A1 | 8/2013 | Guo et al. | |
| 2013/0238015 A1 | 9/2013 | Berdahl et al. | |
| 2013/0274638 A1 | 10/2013 | Jennings et al. | |
| 2014/0275935 A1 | 9/2014 | Walsh et al. | |
| 2015/0094806 A1 | 4/2015 | Scholten | |
| 2015/0164321 A1 | 6/2015 | Weibel et al. | |
| 2015/0313761 A1 | 11/2015 | Berdahl et al. | |
| 2017/0049620 A1 | 2/2017 | Berdahl et al. | |

FOREIGN PATENT DOCUMENTS

| | | |
|---|---|---|
| CN | 103479326 | 1/2014 |
| CN | 203989163 U | 12/2014 |
| CN | 108135738 | 6/2018 |
| JP | H03193037 | 8/1991 |
| JP | 2013255791 | 12/2013 |
| JP | 2018527143 A | 9/2018 |
| WO | WO-2007012008 A2 | 1/2007 |
| WO | WO-2007136993 A1 | 11/2007 |
| WO | WO-2007139927 A1 | 12/2007 |
| WO | WO-2010006180 A1 | 1/2010 |
| WO | 2016071428 | 5/2016 |
| WO | WO-2017035406 A2 | 3/2017 |
| WO | WO-2017035406 A3 | 3/2017 |
| WO | 2017156050 | 9/2017 |
| WO | WO-2018174835 A1 | 9/2018 |
| WO | 2020033736 | 2/2020 |

OTHER PUBLICATIONS

"U.S. Appl. No. 15/688,043, Corrected Notice of Allowability dated Sep. 13, 2018", 3 pgs.
"U.S. Appl. No. 15/688,043, Corrected Notice of Allowability dated Sep. 28, 2018", 3 pgs.
"Canadian Application Serial No. 2,998,477, Examiner's Rule 30(2) Requisition dated Oct. 5, 2018", 3 pgs.
"U.S. Appl. No. 15/688,043, Notice of Allowance dated Jul. 16, 2018", 9 pgs.
"U.S. Appl. No. 15/688,016, Advisory Action dated Jul. 25, 2018", 4 pgs.

(56) References Cited

OTHER PUBLICATIONS

"Australian Application Serial No. 2016311449, First Examination Report dated Jul. 27, 2018", 4 pgs.
"U.S. Appl. No. 15/688,043, Non Final Office Action dated Mar. 15, 2018", 11 pgs.
"International Application Serial No. PCT US2016 048784, International Preliminary Report on Patentability dated Mar. 8, 2018", 12 pgs.
"U.S. Appl. No. 15/345,053, Non Final Office Action dated Feb. 15, 2019", 11 pgs.
"Canadian Application Serial No. 2,998,477, Response Filed Mar. 18, 2019 to Examiner's Rule 30(2) Requisition dated Oct. 5, 2018", 23 pgs.
"U.S. Appl. No. 15/688,016, Final Office Action dated Mar. 25, 2019".
"European Application Serial No. 16763632.3, Communication Pursuant to Article 94(3) EPC dated Apr. 4, 2019", 5 pgs.
"U.S. Appl. No. 15/345,053, Response filed May 13, 2019 to Non Final Office Action dated Feb. 15, 2019", 9 pgs.
"U.S. Appl. No. 15/688,016, Response filed May 28, 2019 to Final Office Action dated Mar. 25, 2019", 10 pgs.
"U.S. Appl. No. 15/912,872, Non Final Office Action dated Jun. 6, 2019", 13 pgs.
"Canadian Application Serial No. 2,998,477, Office Action dated Jun. 25, 2019", 3 pgs.
"Korean Application Serial No. 10-2018-7008191, Notice of Preliminary Rejection dated Jul. 10, 2019", w English Translation, 15 pgs.
"U.S. Appl. No. 15/345,053, Final Office Action dated Aug. 22, 2019", 11 pgs.
"U.S. Appl. No. 15/688,016, Non Final Office Action dated Aug. 29, 2019", 12 pgs.
"U.S. Appl. No. 15/912,872, Examiner Interview Summary dated Aug. 30, 2019", 3 pgs.
"European Application Serial No. 16763632.3, Response Filed Aug. 14, 2019 to Communication Pursuant to Article 94(3) EPC dated Apr. 4, 2019", 15 pgs.
"U.S. Appl. No. 15/912,872, Response filed Sep. 6, 2019 to Non-Final Office Action dated Jun. 6, 2019", 12 pgs.
"Korean Application Serial No. 10-2018-7008191, Response Filed Sep. 4, 2019 to Notice of Preliminary Rejection dated Jul. 10, 2019", w English Claims, 26 pgs.
"Chinese Application Serial No. 201680056279.2, Office Action dated Sep. 12, 2019", w English translation, 21 pgs.
"U.S. Appl. No. 15/345,053, Response filed Oct. 22, 2019 to Final Office Action dated Aug. 22, 2019", 10 pgs.
"European Application Serial No. 16763632.3, Communication Pursuant to Article 94(3) EPC dated Oct. 18, 2019", 4 pgs.
"Eye-Related Intrabody Pressure Identification and Modification", (Oct. 28, 2019), 3.
"U.S. Appl. No. 15/688,016, Response filed Nov. 19, 2019 to Non Final Office Action dated Aug. 29, 2019", 10 pgs.
"U.S. Appl. No. 15/688,016, Examiner Interview Summary dated Nov. 25, 2019", 3 pgs.
"U.S. Appl. No. 15/345,053, Advisory Action dated Dec. 2, 2019", 3 pgs.
"International Application Serial No. PCT US2019 045767, International Search Report dated Nov. 26, 2019", 5 pgs.
"International Application Serial No. PCT US2019 045767, Written Opinion dated Nov. 26, 2019", 7 pgs.
"U.S. Appl. No. 15/912,872, Final Office Action dated Dec. 12, 2019", 13 pgs.
"Canadian Application Serial No. 2,998,477, Response filed Dec. 9, 2019 to Office Action dated Jun. 25, 2019", 19 pgs.
"Biosensor", Merriam-Webster dictionary, [Online]. Retrieved from the Internet: https: www.merriam-webster.com dictionary biosensor, (Jan. 6, 2020), 2 pgs.
"U.S. Appl. No. 15/345,053, Non Final Office Action dated Jan. 13, 2020", 12 pgs.
"Chinese Application Serial No. 201680056279.2, Response filed Jan. 16, 2020 to Office Action dated Sep. 12, 2019", w English Claims, 18 pgs.
"Korean Application Serial No. 10-2018-7008191, Final Office Action dated Jan. 23, 2020", w English Translation, 5 pgs.
"U.S. Appl. No. 15/912,872, Response filed Feb. 12, 2020 to Final Office Action dated Dec. 12, 2019", 9 pgs.
"U.S. Appl. No. 15/688,016, Notice of Allowance dated Feb. 20, 2020", 7 pgs.
"Canadian Application Serial No. 2,998,477, Office Action dated Feb. 17, 2020", 6 pgs.
"U.S. Appl. No. 15/912,872, Advisory Action dated Mar. 11, 2020", 3 pgs.
"U.S. Appl. No. 15/912,872, Response filed Jul. 9, 2018 to Non Final Office Action dated Jun. 8, 2018", 15 pgs.
Costa, Vital P., "Ocular perfusion pressure in glaucoma", Acta Ophthalmologica, (2014), e252-e266.
"U.S. Appl. No. 15/688,016, Final Office Action dated May 15, 2018", 11 pgs.
"U.S. Appl. No. 15/688,016, Response filed Jun. 12, 2018 to Final Office Action dated May 15, 2018", 10 pgs.
"U.S. Appl. No. 15/688,043, Response filed Jun. 15, 2018 to Non Final Office Action dated Mar. 15, 2018", 11 pgs.
"U.S. Appl. No. 15/912,872, Non Final Office Action dated Jun. 8, 2018", 13 pgs.
"U.S. Appl. No. 15/688,043, Corrected Notice of Allowability dated Nov. 20, 2018", 2 pgs.
"U.S. Appl. No. 15/912,872, Final Office Action dated Nov. 28, 2018", 14 pgs.
"U.S. Appl. No. 15/688,016, Response filed Dec. 31, 2018 to Non Final Office Action dated Oct. 5, 2018", 11 pgs.
"U.S. Appl. No. 15/912,872, Response filed Jan. 4, 2019 to Final Office Action dated Nov. 28, 2018", 10 pgs.
"U.S. Appl. No. 15/688,016, Examiner Interview Summary dated Dec. 31, 2018", 3 pgs.
"European Application Serial No. 16763632.3, Response filed Nov. 1, 2018 to Communication Pursuant to Rules 161(1) and 162 EPC dated Apr. 25, 2018", w English Claims, 11 pgs.
"U.S. Appl. No. 13/790,048, Final Office Action dated Feb. 5, 2015", 13 pgs.
"U.S. Appl. No. 13/790,048, Non Final Office Action dated Jun. 24, 2014", 9 pgs.
"U.S. Appl. No. 13/790,048, Notice of Allowance dated May 4, 2015", 12 pgs.
"U.S. Appl. No. 13/790,048, Response filed Apr. 2, 2015 to Final Office Action dated Feb. 5, 2015", 11 pgs.
"U.S. Appl. No. 13/790,048, Response filed Sep. 24, 2014 to Non Final Office Action dated Jun. 24, 2014", 16 pgs.
"U.S. Appl. No. 14/800,018, Examiner Interview Summary dated Mar. 2, 2016", 3 pgs.
"U.S. Appl. No. 14/800,018, Non Final Office Action dated Sep. 28, 2015", 15 pgs.
"U.S. Appl. No. 14/800,018, Notice of Allowance dated Jul. 20, 2016", 11 pgs.
"U.S. Appl. No. 14/800,018, Preliminary Amendment filed Jul. 28, 2015", 5 pgs.
"U.S. Appl. No. 15/345,053, Preliminary Amendment filed Nov. 16, 2016", 5 pgs.
"U.S. Appl. No. 15/345,053, Supplemental Preliminary Amendment filed Aug. 21, 2017", 7 pgs.
"U.S. Appl. No. 15/688,016, Non Final Office Action dated Oct. 20, 2017", 16 pgs.
"U.S. Appl. No. 15/688,016, Preliminary Amendment filed Aug. 20, 2917", 7 pgs.
"U.S. Appl. No. 15/688,016, Response filed Jan. 16, 2018 to Non Final Office Action dated Oct. 20, 2017", 9 pgs.
"U.S. Appl. No. 15/688,043, Preliminary Amendment filed Aug. 29, 2017", 7 pgs.
"U.S. Appl. No. 14/800,018 Response filed Jan. 15, 2016 to Non-Final Office Action dated Sep. 28, 2015", 20 pgs.
"Cataract Surgery to Lower Intraocular Pressure", Middle East African Journal of Ophthalmology, 16 (3), (Sep. 2009), 1-5.

(56) References Cited

OTHER PUBLICATIONS

"Cerebrospinal Fluid Pressure Is Decreased in Primary Open-angle Glaucoma", American Academy of Ophthalmology, Manuscript No. 2007-1002, (2008), 763-768.

"EyeGateII Transcription", youtube, [Online]. Retrieved from the Internet: <URL: https://www.youtube.com/watch?v=v7oSLebLWo, (Accessed Nov. 3, 2017), 1 pg.

"International Application Serial No. PCT/US2016/048784, International Search Report dated Mar. 21, 2017", 9 pgs.

"International Application Serial No. PCT/US2016/048784, Invitation to Pay Additional Fees and Partial Search Report dated Nov. 28, 2016", 7 pgs.

"International Application Serial No. PCT/US2016/048784, Written Opinion dated Mar. 21, 2017", 10 pgs.

Alexander, David J., et al., "Risk of Spaceflight-Induced Intracranial Hypertension and Vision Alterations", Evidence Report—Version 1.0, (Jul. 12, 2012), 1-106.

Allin, David, et al., "Laboratory Testing of the Pressio Intracranial Pressure Monitor", Neurosurgery, vol. 62, vol. 5, [Online]. Retrieved from the Internet: <URL: www.neurosurgery-online.com, (May 2008), 1158-1161.

Araci, Ismail E., et al., "An implantable microfluidic device for self-monitoring of intraocular pressure", Nature Medicine, vol. 20, No. 9, (Sep. 2014), 1074-1080.

Araci, Ismail E., "An implantable microfuidic device for self-monitoring of intraocular pressure", nature medicine, vol. 20, No. 9—Technical Reports, (Sep. 2014), 1074-1080.

Berdahl, J. P., et al., "Intracranial pressure and glaucoma", Curr Opin OPhthalmol (2), (Mar. 2010), 1 pg.

Berdahl, J. P., et al., "The translaminar pressure gradient in sustained zero gravity,idiopathic intracranial hypertension, and glaucoma", PubMed 79(6), (Dec. 2012), 1 pg.

Berdahl, John P., et al., "Body Mass Index Has a Linear Relationship with Cerebrospinal Fluid Pressure", IOVS, vol. 53, No. 3, (Mar. 2012), 1422-1427.

Berdahl, John, "Cerebrospinal Fluid Pressure and Glaucoma", Glaucoma Today, (Oct. 2009), 14-18.

Berdahl, John P., et al., "Intracranial pressure and glaucoma", Current Opinion in Ophthalmology 21-, (2010), 106-111.

Berdahl, John P., et al., "Intracranial Pressure in Primary Open Angle Glaucoma, Normal Tension Glaucoma, and Ocluar Hypertension: A Case-Control Study", IOVS, vol. 49, No. 12, (Dec. 2008), 5412-5418.

Berdahl, John P., "Recovery of Corneal Hysteresis after Reduction of Intraocular Pressure in Chronic Primary Angle-Closure Glaucoma", American Journal of Ophthalmology—Correspondence, (Oct. 2009), 623-624.

Berdahl, John P., "Systemic Parameters Associated With Cerebrospinal Fluid Pressure", J Glaucoma, vol. 22, No. 5, Suppl 1, [Online]. Retrieved from the Internet: <URL: www.glaucomajournal.com, (Jul. 2013), S17-S18.

Berdahl, John P., "The translaminar pressure gradient in sustained zero gravity, idiopathic inracranial hypertension and glaucoma", Medical Hypotheses 79, (2012), 719-724.

Fleischman, David, et al., "Cerebrospinal Fluid Pressure Decreases with Older Age", PLOS One, vol. 7, Issue 12, [Online]. Retrieved from the Internet: <URL: www.plosone.org, (Dec. 2012), 1-9.

Fleischman, David, et al., "Increasing intraocular pressure as treatment for papilledema", Experimental Eye Research 115, (2013), 278.

Fleischman, David, et al., "The role of cerebrospinal fluid pressure in glaucoma and other ophthalmic diseases: A review", Saudi Journal of Ophthalmology, 27, (2013), 97-106.

Goel, Manik, et al., "Aqueous Humor Dynamics: A Review", The Open Ophthalmology Journal, [Online]. Retrieved from the Internet: <URL: http://www.ncbi.nlm.nih.gov/pmc/articles/PMC3032230>, (2010), 52-59.

Goldman, Robert M., et al., "The Effects of Oscillating Inversion on Systemic Blood Pressure, Pulse Intraocular Pressure, and Central Retinal Arterial Pressure", The Physician and Sportsmedicine, vol. 13, No. 3, (Mar. 1985), 93-96.

Hayreh, Sohan Singh, "Cerebrospinal fluid pressure and glaucomatous optic disc cupping (response to Berdahl and colleagues)", Graefes Arch Clin Exp Opthtalmol, 247, (2009), 1291-1294.

Hillen, Mark, "In Practice (VIIP: A Space Odyssey)", The Ophthalmologist , vol. 11, (Sep. 2014), 30-34.

Huberman, Andrew, "Managing Glaucoma: Beyond Intraocular Pressure. 2011", Review of Opthalmology, [Online]. Retrieved from the Internet: <URL: : http://www.reviewofophthalmology.com/continuing_education/tabviewtest/lessonid/107804/, (Sep. 2011), 17 pgs.

Jacks, A. S., et al., "Spontaneous retinal venous pulsation: aetiology and significance", J Neurol Neurosurg Psychiatry; 74, [Online]. Retrieved from the Internet: <URL: www.jnnp.com, (2002), 7-9.

Jonas, Jost R., et al., "Anatomic Relationship between Lamina Cribrosa,Intraocular Space, and Cerebrospinal Fluid Space", Investigative Ophthalmology & Visual Science, Dec. 2003, vol. 44, No. 12, Investigative Ophthalmology & Visual Science, vol. 44, No. 12, (Dec. 2003), 5189-5195.

Jung, Jong Jin, et al., "Analysis of the Causes of Optic-Disc Swelling", Korean J Ophthalmol, 25 (1), (2011), 33-36.

Kent, Christopher, "IOP: Managing the Fluctuation Factor", Review of OPhthalmology,[Online]. Retrieved from the Internet: <URL: http://www.reviewofophthalmology.com/content/i/1533/c/28662/dnnprintmode/true/?skinsrc=[l]skins/rp2010/pageprint&containersrc=[l]containers/rp2010/blank, (Jun. 13, 2011), 6 pgs.

Kent, Christopher, "IOP: Managing the Fluctuation Factor", Review of Ophthamology, (Nov. 21, 2015), 6 pgs.

Morgan, William H., et al., "Retinal venous pulsation: Expanding our understanding and use of this enigmatic phenomenon", Progress in Retinal and Eye Research xxx, (2016), 1-26.

Muenster, Stefan, et al., "The Ability of Nitric Oxide to Lower Intraocular Pressure Is Dependent on Guanylyl Cyclase", Investigative Ophthalmology & Visual Science, vol. 58, No. 11, (Sep. 2017), 4826-4835.

Siaudvytyte, Lina, et al., "Update in intracranial pressure evaluation methods and translaminar pressure gradient role in glaucoma", ACTA Opththmalologica, 93, (2015), 9-15.

Wostyn, Peter, et al., "Glaucoma and the Role of Cerebrospinal Fluid Dynamics", Investigative Ophthalmology & Visual Sciences, (2015), 6630.

Wuthrich, U. W., "Postural change and intraocular pressure in glaucomatous eyes", Brit. J. Ophthal. 60, (1976), 111-114.

Xie, Xiaobin, et al., "Noninvasive intracranial pressure estimation by orbital subarachnoid space measurement: the Beijing Intracranial and Intraocular Pressure (iCOP) study", Critical Care, 17:R162, [Online]. Retrieved from the Internet: <URL: http://www.ncbi.nlm.nih.gov/pmc/articles/PMC4056099/pdf/cc12841.pdf, (2013), 12 pgs.

Yeoh, Ronald, "Hydrorupture of the posterior capsule in femtosecond-laser cataract surgery", J Cataract Refract Surg, vol. 38, (Apr. 2012), 730-731.

Young, Joshua, "ASFH CSF Pressure and Glaucoma (Guest: John P. Berdahl, M.D.)", As Seen From Here: 198 (Podcast—iTunes) (Transcribed), (Jul. 8, 2008), Run time: 15:14 Minutes.

Zhang, Zheng, et al., "Glaucoma and the Role of Cerebrospinal Fluid Dynamics", Investigative Ophthalmology & Visual Sciences, (2015), 6632.

"U.S. Appl. No. 15/345,053, Response filed Apr. 13, 2020 to Non Final Office Action dated Jan. 13, 2020", 9 pgs.

"U.S. Appl. No. 15/688,016, Corrected Notice of Allowability dated Jun. 15, 2020".

"U.S. Appl. No. 15/912,872, Non Final Office Action dated Apr. 30, 2020", 17 pgs.

"U.S. Appl. No. 15/912,872, Response filed Mar. 20, 2020 to Advisory Action dated Mar. 11, 2020", 9 pgs.

"Australian Application Serial No. 2019202196, First Examination Report dated Apr. 22, 2020", 5 pgs.

"Brazilian Application Serial No. 1120180038385, Office Action dated Jun. 24, 2020", w/ English Translation, 5 pgs.

(56) References Cited

OTHER PUBLICATIONS

"Canadian Application Serial No. 2,998,477, Response filed Jun. 9, 2020 to Office Action dated Feb. 17, 2020", 18 pgs.

"Chinese Application Serial No. 201680056279.2, Office Action dated May 22, 2020", w/ English Translation, 19 pgs.

"European Application Serial No. 16763632.3, Communication Pursuant to Article 94(3) EPC dated Mar. 26, 2020", 4 pgs.

"European Application Serial No. 16763632.3, Response filed Feb. 27, 2020 to Communication Pursuant to Article 94(3) EPC dated Oct. 18, 2019", 11 pgs.

"Korean Application Serial No. 10 2018-7008191, Response filed Mar. 25, 2020 to Final Office Action dated Jan. 23, 2020", w/ English Claims, 12 pgs.

"U.S. Appl. No. 15/345,053, Final Office Action dated Jul. 24, 2020", 11 pgs.

"Canadian Application Serial No. 2,998,477, Office Action dated Aug. 7, 2020", 6 pgs.

"Japanese Application Serial No. 2018-529509, Notification of Reasons for Refusal dated Aug. 11, 2020", w English translation, 9 pgs.

"Australian Application Serial No. 2019202196, Response filed Aug. 19, 2020 to First Examination Report dated Apr. 22, 2020", 19 pgs.

"Chinese Application Serial No. 201680056279.2, Response filed Sep. 27, 2020 to Office Action dated May 22, 2020", w English Claims, 19 pgs.

"European Application Serial No. 167636323, Communication Pursuant to Article 94(3) EPC dated Sep. 28, 2020", 5 pgs.

"U.S. Appl. No. 15/345,053, Response filed Sep. 23, 2020 to Final Office Action dated Jul. 24, 2020", 10 pgs.

"U.S. Appl. No. 15/912,872, Notice of Allowance dated Oct. 5, 2020", 8 pgs.

\* cited by examiner

EYE-RELATED INTRABODY PRESSURE IDENTIFICATION AND MODIFICATION

CLAIM OF PRIORITY

This patent application is a U.S. National Stage Application Under 35 U.S.C. 371 from International Application Number PCT/US2016/048784, filed Aug. 25, 2016, which claims the benefit of priority of Berdahl U.S. Provisional Patent Application Ser. No. 62/210,751, entitled "Detecting Intrabody Pressure Using Eye Blood Vessel Characteristic," filed on Aug. 27, 2015 and of Berdahl U.S. Provisional Patent Application Ser. No. 62/311,052, entitled "Apparatus and Methods for Ocular Pressure Modification," filed on Mar. 21, 2016 all of which are hereby incorporated by reference in their entirety.

BACKGROUND

Measuring eye pressure is important in diagnosing and treating diseases of the eye, such as glaucoma. Early diagnosis and treatment of glaucoma is a key to inhibiting or preventing loss of vision. Non-contacting tonometers are useful instruments for measuring eye pressure, but can cause patient discomfort in use.

U.S. Pat. No. 4,724,843 mentions a tonometer that fires a controlled puff of air onto the cornea.

U.S. Pat. No. 5,523,808 mentions a composite ophthalmic apparatus with an intraocular pressure measuring system for spraying a fluid from a nozzle against an eye.

U.S. Pat. No. 6,673,014 mentions noninvasive methods and apparatuses for measuring the intraocular pressure of the eye using vibratory excitation.

US Patent Application 2013/0211285 mentions systems and methods for noninvasively assessing intracranial pressure by controllably osculating at least a portion of a subject's ocular globe while applying a force sufficient to collapse an intraocular blood vessel and correlating the collapse pressure to intracranial pressure.

U.S. Pat. No. 9,125,724 mentions assemblies and methods that can be used to treat, inhibit, or prevent ocular conditions.

US Patent Application 2015/0313761 mentions assemblies and methods that can be used to treat, inhibit, or prevent ocular conditions.

OVERVIEW

An apparatus for at least one of diagnosing or treating an eye condition can include a goggle enclosure, sized and shaped to be seated on an eye socket of an eye to provide one or more cavities within the enclosure that extend about an entire exposed anterior portion of the eye, a pump, in fluidic communication with the one or more cavities to apply a fluid pressure to the one or more cavities, the pump configured to adjust a fluid pressure within the one or more cavities of the goggle enclosure, and a control circuit, including a data interface to receive data directly or indirectly indicating at least one of an intraorbital pressure, ICP, IOP, or a relationship between ICP and IOP, and based on processing the received data as a feedback control variable, controlling the pump to adjust the fluid pressure within the one or more cavities, the controlling including using further monitoring of the received data to control the pump.

This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Figure 1A:
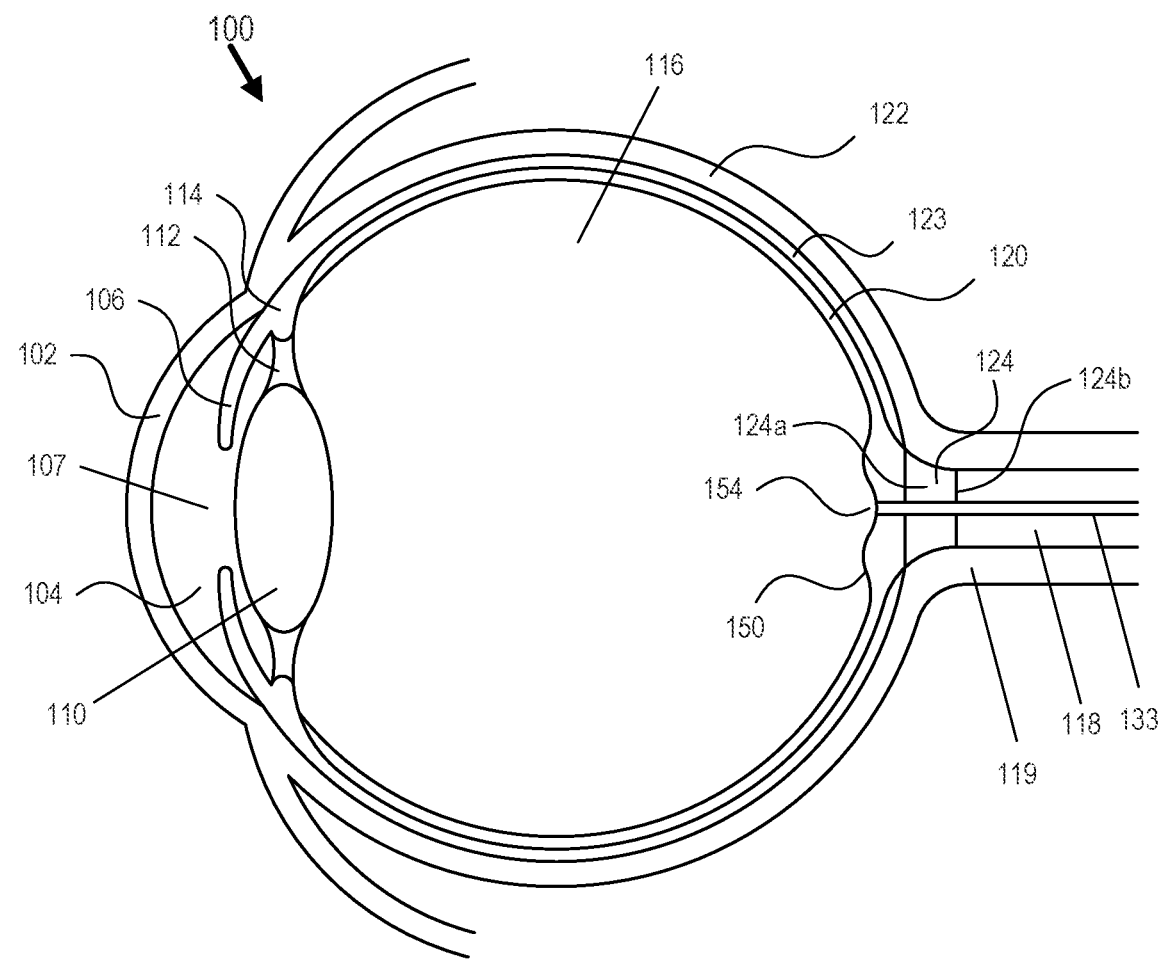
FIG. 1A shows a lateral cross section of an example of a human eye.

FIG. 1A shows a lateral cross section of an example of a human eye 100. The eye 100 includes two chambers within the sclera 122; an anterior chamber 104 and a posterior chamber 116. The anterior chamber 104 is defined generally as the space between the cornea 102 and the iris 106 and is filled with aqueous humor. The pupil 107 is a hole defined by the iris 106 that allows light to enter the eye 100. The lens 110 is located behind the iris 106 and is supported by ligaments 112. The ciliary processes 114, which include the ciliary body and ciliary muscle, surround the lens 110 and are located behind the iris 106.

The posterior chamber 116, located between the anterior chamber 104 and the retina 120, is filled with vitreous humor. The retina 120 is supported structurally and physiologically by the choroid 123 located between the retina 120 and the sclera 122.

Collectively, the anterior and posterior chambers 104, 116 are referred to as the intraocular space of the eye 100. The anterior chamber 104 is distinct from the posterior chamber 116, however, the separation between the two chambers is elastic so that fluid pressures due to the aqueous humor and viscous humor are equal or approximately equal at any given time. The pressure of the fluids in the intraocular space can be referred to as the intraocular pressure, or IOP.

The optic nerve 118 connects the retina 120 to the brain to deliver visual stimuli from the retina 120 to the brain for processing. The optic nerve 118 is surrounded by the dural sheath 119 and bathed in cerebrospinal fluid (CSF). As the dural sheath 119 is in fluid communication with the intracranial space, CSF pressure is equal to or approximately equal to the intracranial pressure (ICP).

The optic disc 150 (or optic nerve head) connects the optic nerve 118 to the retina 120. The optic disc 150 is visible on the surface of the retina 120 and can assume a generally circular shape, such as an oval, with an orange-pink coloration indicating the presence of well-perfused nerve tissue. The optic disc 150 can include a centrally-located, cup-like depression referred to as the optic cup 154 that can appear pale in contrast to the orange-pink color of the optic disc 150.

The ratio of the diameter of the optic cup 154 to the diameter of the optic disc 150 can be referred to as the cup-to-disc ratio. In an eye 100 that is generally healthy, such as a non-glaucomatous eye, a cup-to-disc ratio of approximately 0.3 is generally considered normal. Cup-to-disc ratios greater than or less than approximately 0.3 can indicate damage to the optic nerve 118, such as with the progression of an eye disease including glaucoma and optic disc edema.

The intraocular space is separated from the intracranial space by the lamina cribrosa 124, a mesh-like, collagenous membrane structure located in the posterior portion of the sclera 122. Fibers of the optic nerve 118 can weave through the lamina cribrosa 124 to connect the retina 120 to the brain while the lamina cribrosa 124 can maintain a pressure differential between the intraocular and intracranial spaces. The intraocular surface of the lamina cribrosa 124a is exposed to IOP whereas the intracranial surface of the lamina cribrosa 124b is exposed to ICP.

The lamina cribrosa 124 is more flexible than the adjacent sclera 122 and can deform under the influence of a translaminar pressure difference (TPD), which is the difference between the IOP and the ICP (e.g., TPD=IOP−ICP) at any given time. The translaminar pressure gradient (TPG) can be represented by the difference between the IOP and the ICP divided by the thickness of the lamina cribrosa 124. In a normal eye 100, IOP is generally greater than ICP and thus, the lamina cribrosa is ordinarily subjected to a posteriorly directed pressure difference, such as to cause the laminar cribrosa 124 to bow outwardly from the intraocular space to form the optic cup 154 in the optic disc 150. In an eye 100 that is generally healthy, a physiologically normal TPD is approximately 4 mmHg. Under the influence of the physiologically normal TPD, the lamina cribrosa 124 can support the optic disc 150 in a nominal position, such as to form a cup-to-disc ratio of about 0.3.

Changes in TPD can indicate the presence of an eye condition, such as an abnormal eye condition, in the eye 100. As TPD increases from the physiologically normal TPD, such as due to the effects of increasing IOP, decreasing ICP, or both, the lamina cribosa 124 can deflect posteriorly from the nominal position causing the optic cup 154 to increase in diameter, such as to increase the cup-to-disc ratio to a value greater than about 0.3. As TPD decreases from the physiologically normal TPD, such as due to the effects of increasing ICP, decreasing IOP, or both, the lamina cribrosa 124 can deflect anteriorly from the nominal position causing the optic cup 154 to decrease in diameter, such as to decrease the cup-to-disc ratio to a value less than about 0.3.

Changes TPD can be positively correlated with diseases of the eye 100. For example, glaucoma can arise from an imbalance between IOP and ICP. An increase in IOP or a decrease in ICP can create a pressure differential across the optic nerve 118. ICP can affect the optic nerve 118, such as in pseudotumor cerebri (idiopathic intracranial hypertension) in which elevated ICP can force the optic nerve to bow forward, such as from a physiologically normal position, and in glaucoma, where reduced ICP can force the optic nerve 118 to cup, such as in cupping of the optic nerve 118, such as because a high IOP and a low ICP can force the optic nerve backwards, such as from a physiologically normal position.

Eye diseases, such as glaucoma, can also result from other disorders, such as a metabolic disease or disorder. In a normal eye 100, such as an eye 100 with physiologically normal function, axonal transport through the optic nerve can service the metabolic needs of ganglion cells across the lamina cribrosa. In an abnormal eye 100, such as an eye without physiologically normal function, such as an eye 100 experiencing an elevated IOP, a reduced ICP, or both, axonal transport can be impeded, or potentially stopped, from passing through the lamina cribrosa, such as may cause ganglion cell death and the occurrence of glaucoma.

Changes in TPD can be positively correlated with visual field loss, such as loss associated with damage to the optic nerve 118 due to a reduction in axonal transport. Axonal transport can describe the collection of cellular processes required to maintain the viability of nerve cells in the eye 100, such as metabolic processes. A decrease in axonal transport can occur when cellular processes supporting the optic nerve 118 and retina 120 are impeded, such as when a patient experiences a TPD in one or both eyes 100 that is elevated or reduced from the physiologically normal TPD.

The duration of time that axonal transport is impeded in the eye 100 can affect the extent of damage suffered by the optic nerve 118. While the deleterious effects on the optic nerve 118 of acute decreases in axonal transport, such as due to short-term increases or decreases of TPD from a physiologically normal TPD, can be reversible, chronic changes in axonal transport, such as due to long-term increases or decreases of TPD from a physiologically normal TPD, can be related to permanent damage of the optic nerve 118.

The eye 100 is supplied with oxygenated blood from the circulatory system by several branches of the ophthalmic artery, including the central retinal artery 130, the anterior ciliary artery, and the posterior ciliary artery. The central retinal artery 130 perfuses the optic nerve 118 and the retina 120. The anterior and posterior ciliary arteries together perfuse the ciliary processes 114, the iris 116, the sclera 122, and the choroid 132. Deoxygenated blood is returned to the circulatory system via the central retinal vein 133 and the vortex veins which drain into the superior and inferior ophthalmic veins. The central retinal vein 133 passes through the subarachnoid space of the optic nerve 118 and is bathed in CSF at the ICP of the patient before draining into the cavernous sinus. As a result, the pressure in the central retinal vein 133 is equal to or higher than the ICP. A linear correlation exists between the pressure in the central retinal vein 133 and ICP.

The eye 100 can be subjected to at least three different pressures at any given time, such as an atmospheric pressure on the exposed anterior portion of the eye 100, an IOP in the intraocular space of the eye 100, and an ICP on the posterior portion of the eye 100 surface. Blood vessels in the eye 100, such as venous blood vessels including the central retinal vein 133, can pass through the subarachnoid space of the optic nerve 118 and can be bathed in cerebrospinal fluid at the intracranial pressure of the patient, such as before draining into the cavernous sinus. As a result, the pressure in a venous blood vessel, such as the intraluminal pressure in the central retinal vein 133, can be equal to or greater than ICP.

The ocular pulse cycle can be characterized by the ocular pulse amplitude, such as the difference between systolic and diastolic intraocular pressure. The ocular pulse cycle, such as the systolic and diastolic intraocular pressure of the eye 100, can be related to the cardiac cycle of the patient. The intracranial pulse cycle can be characterized by the intracranial pulse amplitude, such as the difference between systolic and diastolic intracranial pressure. The intracranial pulse cycle, such as the systolic and diastolic intracranial pressures, can be related to the cardiac cycle of the patient.

Figure 1B:
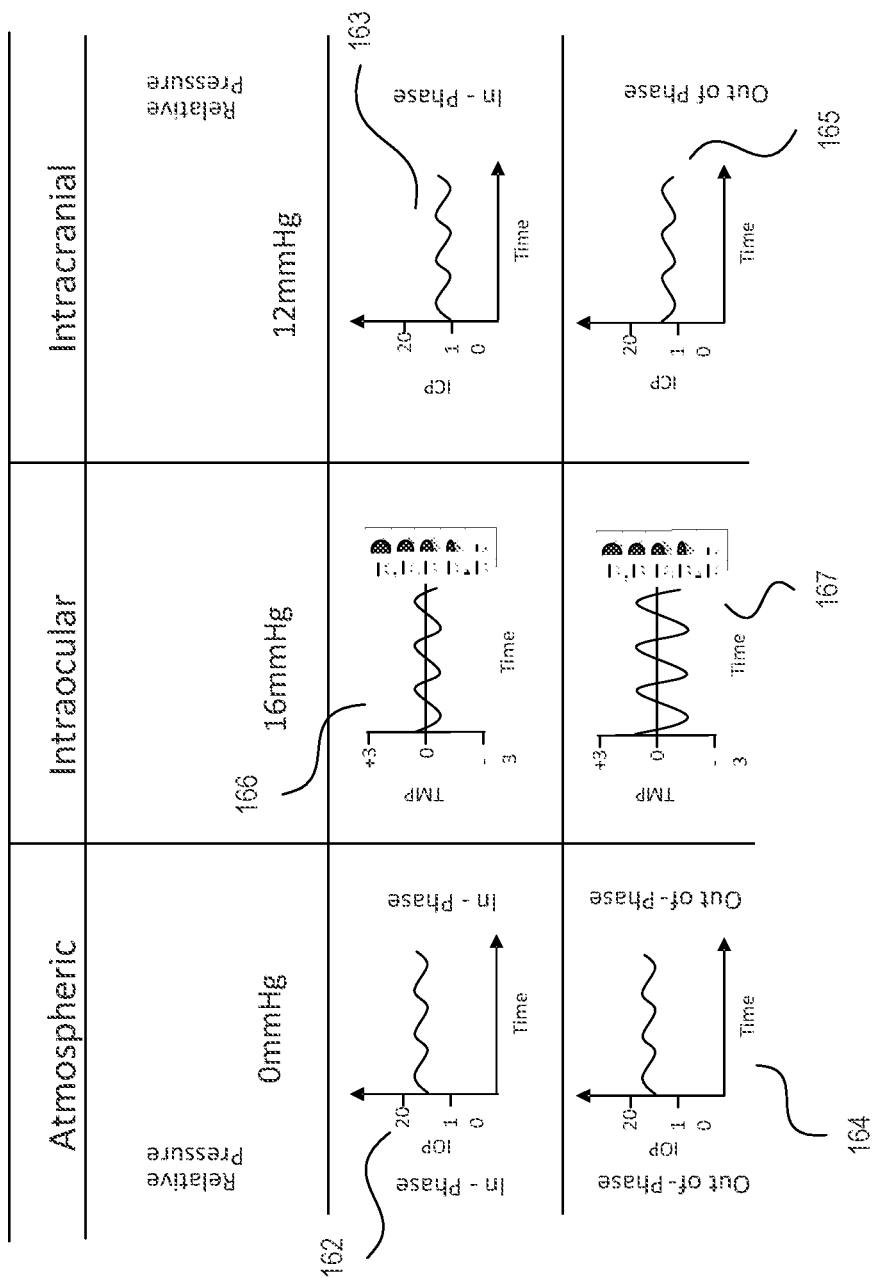
FIG. 1B shows an example of pressures associated with a physiologically normal eye.

FIG. 1B shows an example of pressures associated with a physiologically normal eye 100. IOP can be greater than ICP, such as about 4 mmHg greater than ICP. IOP can include a quasi-static IOP component, such as an average IOP, such as can slowly vary over time due to physiological conditions of the eye 100, and a dynamic IOP component, such as a varying component of IOP, such as can vary with at least one indication of the cardiac cycle of the patient. At 162, the dynamic IOP component can be in-phase, such as with an indication of the cardiac cycle of the patient. At 164, the dynamic IOP component can be out-of-phase with an indication of the cardiac cycle of the patient. ICP can include a quasi-static ICP component, such as an average ICP, such as can slowly vary over time due physiological conditions of the patient, and a dynamic IOP component, such as a varying component of ICP, such as can vary with at least one indication of the cardiac cycle of the patient. At 163, the dynamic ICP component can be in-phase, such as with an indication of the cardiac cycle of the patient. At 165, the dynamic ICP component can be out-of-phase with an indication of the cardiac cycle of the patient.

Transmural pressure (TMP) can be defined as the difference between the intraluminal pressure of a vessel of the patient eye 100, such as the pressure in the central retinal vein 133 including ICP, and a chamber pressure of the patient eye 100, such as IOP. The TMP can be related to an eye characteristic, such as an SVP including an indication of SVP, such as a change in caliber of a blood vessel in the eye 100. At 166, the in-phase dynamic IOP component and the in-phase dynamic ICP component can combine, such as destructively interfere, such as to minimize the dynamic component of TMP. At 167, the in-phase dynamic IOP component and the in-phase dynamic ICP component can combine, such as constructively interfere, such as to maximize the dynamic component of TMP.

Spontaneous venous pulsations (SVP) occur in venous vessels of the eye 100, such as the central retinal vein. SVP occur near the site of large venous pressure changes, such as the pressure gradient between IOP and ICP experienced at the retrobulbar optic nerve, within highly compliant vessels, such as veins of the eye 100. The pulsation characteristics of SVP can depend upon several variables, such as IOP and ICP.

ICP can be non-invasively estimated by temporarily increasing IOP in an eye 100 of a patient. In an example, an instrument can be placed in contact with the eye 100, such as an anterior portion of the eye 100, and the instrument pressed against the eye 100, such as to increase the IOP of the eye 100. One or more blood vessels, such as venous blood vessels, in the eye 100 can be observed by a person other than the patient, such as a medical professional, while the IOP of the eye 100 is increased until at least one criterion, such as an eye characteristic change criterion, is achieved. In an example, an eye characteristic change criterion can include the collapse of the central retinal vein 133, such as due to increased IOP in the eye 100.

Removal of the instrument pressed against the eye 100 can decrease the IOP of the eye 100, such as to allow a collapsed vessel to regain a generally circular cross-sectional shape. One or more blood vessels, such as venous blood vessels, in the eye 100 can be observed by a person other than the patient, such as a medical professional, while the IOP of the eye 100 is decreased until a criterion, such as an eye characteristic rebound criterion, is achieved. Detection of an eye characteristic rebound criterion can indicate that the affected body tissue has recovered to an ambient state, such as a normal physiological state as existed before applying the instrument pressed against the eye 100. In an example, an eye characteristic rebound criterion can include the recovery of the central retinal vein 133 to an ambient cross-sectional shape, such as a generally circular shape.

An eye characteristic can describe a physical feature of the body of a patient, such as at least one of a physical feature of a patient eye 100 or a physical feature of the patient body related to the patient eye 100. An indication of an eye characteristic can include a numerical value associated with a particular level or quantity of an eye characteristic. A numerical value can represent a single indication of an eye characteristic, such as a first value or a second value, or a change in an indication of an eye characteristic, such as the difference between the first value and the second value.

Indications of eye characteristics associated with the eye 100 can change under the influence of forces applied to the body of a patient, such as when the body of a patient is subjected to inertial forces. Inertial forces can be generated within the eye 100, such as by sudden acceleration or deceleration of the eye 100.

Indications of eye characteristic associated with the eye 100 can change under the influence of changes in hydrostatic pressures, such as differential hydrostatic pressures, in the body of the patient. Eye characteristic associated with the eye 100 can change due to changes in hydrostatic IOP and ICP, such as a patient transitioning from a first body position, such as a standing position, to a second body position, such as a sitting or prone position. Changes in indications of eye characteristics subjected to differential hydrostatic pressures can include a change in the caliber or diameter of blood vessels, such as at least one of a retinal vein or a retinal artery. A change in the caliber or diameter of a blood vessel can include a pulsation, such as a pulsation detected by an imaging device due to changes in systemic blood pressure, such as during systole and diastole, can be indicative of the cardiac cycle.

Indications of eye characteristics associated with the eye 100 can change under the influence of forces applied to the eye 100, such as when the eye 100 is subjected to gauge pressures applied to the cavity 212 of the goggle enclosure 210 by the apparatus 200. Forces can be generated on the anterior surface of the eye 100 by applying fluid pressures, such as positive or negative gauge pressures, to the cavity 212 with the pump 220.

Indications of eye characteristics associated with the eye 100 can be calculated, or otherwise estimated, as a function of one or more parameters including one or more indications of eye characteristics and one or more indications of body parameters, such as at least one of body mass index (BMI) of a patient or chronological age of a patient. An indication of ICP can include an estimate of CSF pressure, such as an estimate of CSF pressure calculated based upon knowledge of blood pressure, BMI, and chronological age of the patient.

An eye characteristic can include an intrabody pressure of the eye 100. An intrabody pressure can include a pressure associated with the eye 100, such as at least one of an IOP, an ICP, an episcleral venous pressure (EVP), or a pressure between the eye 100 and the body of the patient, such as a translaminar pressure difference (TPD), translaminar pressure gradient (TPG), or an orbital pressure. Intracranial pressure (ICP) can sometimes be referred to as cerebrospinal fluid pressure (CSFP).

An eye characteristic can include a physical characteristic of the eye 100, such as a physical characteristic that describes or can be associated with the structure of the eye 100. A structure of the eye 100 can include components of the eye, such as the lamina cribrosa 124, the retina 120 including the retinal nerve fiber layer (RNFL), and the choroid 123. A physical characteristic of a structure of the eye 100 can include at least one of the thickness of the structure, the color of the structure, the reflectance of the structure, such as can be related to the color and reflectivity of the structure, or motion of the structure in the eye 100, such as relative to at least one of a structure outside the eye 100, such as at least one of a visualization assistance device or a goggle enclosure 210, or with respect to a structure of the eye 100. In an example, an eye characteristic can include the motion of the lamina cribrosa, such as at least one of motion with respect to a structure outside the eye 100, or motion with respect to a structure of the eye, such as motion of the lamina cribrosa with respect to the anterior surface of the eye 100. A structure of the eye 100 can include a blood vessel of the eye 100, such as an arterial vessel or a venous vessel such as can include the central retinal vein 133. A physical characteristic of the blood vessel of the eye 100 can include a cross-sectional caliber (or diameter) of the blood vessel, such as the caliber of the central retinal vein 133 or the shape of the blood vessel, such as the cross-sectional shape of the central retinal vein 133. In an example, pressure in the central retinal vein 133 can approximate ICP. A physical characteristic of a blood vessel of the eye 100 can include at least one of the color or the reflectance (or intensity of reflected light) characteristics of the blood vessel.

An eye characteristic can include a body parameter of the patient associated with the eye 100. A body parameter can include other metrics, such as chronological age and body mass index (BMI). A body parameter can include an indication of a fluid pressure applied to the eye 100, such as a fluid pressure applied to an anterior portion of the eye 100. A body parameter can include an indication of the cardiac cycle, such as an indication of heart rate, an indication of systemic blood pressure, such as systolic and diastolic pressures, or an indication of spontaneous venous pulsation. An indication of the cardiac cycle can include at least one characteristic of an SVP, such as the frequency of the SVP, the change in vessel caliber due to the SVP, the phase of SVP relative to systemic blood pressure, such as systemic systole and diastole, the velocity of blood flow during SVP, or blood column oscillation associated with SVP.

An eye characteristic can include a flow characteristic of the eye 100, such as a flow characteristic of a blood vessel of the eye 100. A flow characteristic of a blood vessel of the eye 100 can include at least one of average or other central tendency of velocity of blood flow, such as can be related to levels of IOP and CSF, systolic and diastolic velocity of blood flow, and density of blood flow. Flow characteristics of a blood vessel can change in a periodic fashion, for example, the flow characteristics can be related to the cardiac cycle. Flow characteristics in a blood vessel can be related to IOP, CSF, or both IOP and CSF, such as flow velocities in a vessel can be affected by changes in CSF. A flow characteristic can include a composite characteristic, such as an eye characteristic calculated from one or more eye characteristics. Composite characteristics can include the pulsatility index (PI) and the resistivity index (RI). ICP can be estimated using a method, such as can include measuring venous outflow pressure, measuring central retinal arterial blood flow, and estimating ICP using the venous outflow data and at least one of a pulsatility or resistivity relationship.

The apparatus 200 can be used in or in combination with one or more sensing instruments 513 to apply fluid pressures, such as therapeutic pressures, to the eye 100. Applying therapeutic pressures to the eye 100 can modify pressure indications associated with the eye 100, such as indications of physiological parameters, to treat one or more eye conditions of the eye 100.

Figure 2:
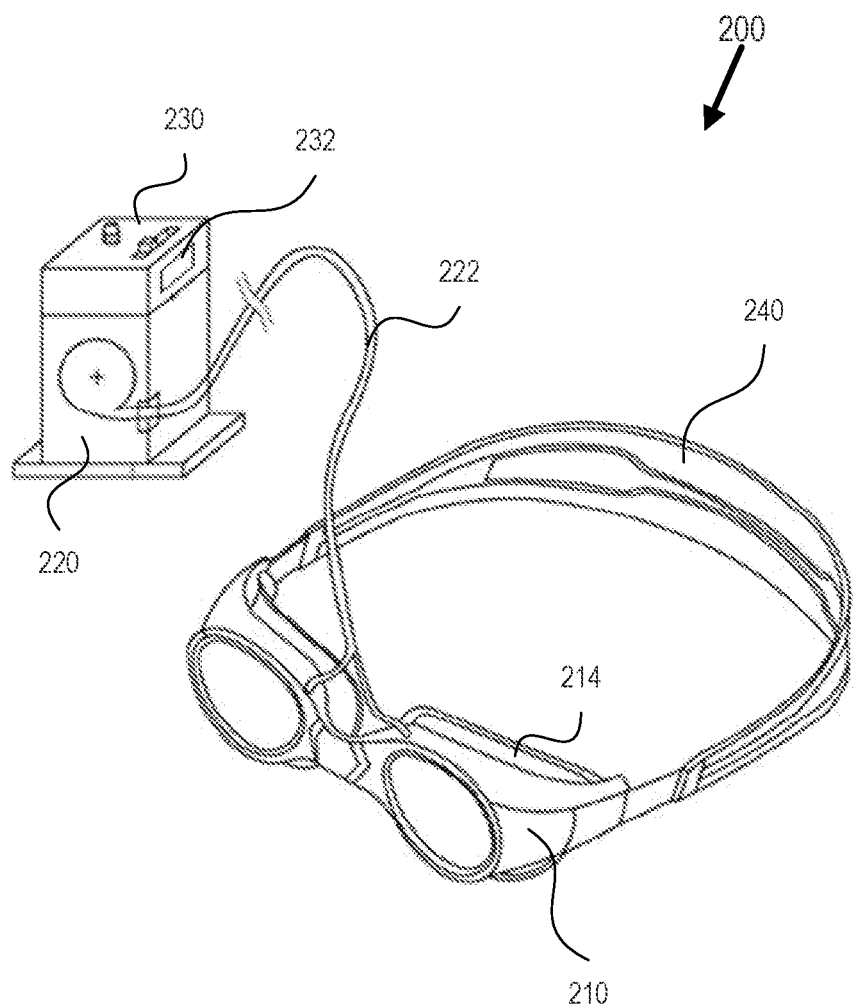
FIG. 2 shows an example of an assembly, such as for applying fluid pressure to an external surface of the eye, such for at least one of diagnosing or treating an eye condition, such as can include an abnormal eye condition.

FIG. 2 shows an example of an apparatus 200, such as for applying fluid pressure to an external surface of the eye 100, such for at least one of diagnosing or treating an eye condition, such as can include an abnormal eye condition. Applying fluid pressures to the eye 100 can induce changes in the eye 100, such as to change characteristics of the eye 100, such as fluid pressures associated with the eye 100.

The apparatus 200 can include an goggle enclosure 210, a pump 220 in fluid communication with the goggle enclosure 210, a control circuit 230 in electrical communication with the pump 220, and a locating device 240 connected to the goggle enclosure 210. In an example, the apparatus 200 can include one or more enclosures 210, such as to form a set of goggles that can be located over the eyes 100 of a patient for diagnosing or treating for an eye condition. In an example, an image processor circuit can include at least one of the control circuit 230 or a VAD image processor circuit.

The apparatus 200 can provide adjustable control over IOP in a patient eye 100 such as to balance IOP with ICP or otherwise control TPD in the patient eye 100 to treat an abnormal eye condition. In an example, an abnormal eye condition, such as glaucoma, can be treated by using the goggles and pump for drawing a small vacuum to the external surface of the patient eye 100 in the goggle enclosure 210, such as a vacuum of 10-15 mmHg relative to the surrounding ambient atmospheric pressure outside of the goggles, such as to reduce IOP and balance TPD. In an example, an abnormal eye condition, such as Vision Impairment and Intracranial Pressure (or VIIP), such as due to microgravity-induced increases in ICP, can be treated by applying a positive pressure to the surface of the patient eye 100 in the goggle enclosure 210, such as to increase ICP and balance TPD. VIIP can include a one or more of a variety of abnormal eye conditions, such as hyperopic shifts, scotoma, cotton wool spots, choroidal folds, optic nerve sheath distension, globe flattening, and optic nerve edema.

The goggle enclosure 210 can be sized and shaped to surround the patient eye 100, such as to be seated on an eye socket of the eye 100, and be spaced from the eye 100 without contacting the eye 100. The goggle enclosure 210 placed against the patient can include or define a cavity 212 between the goggle enclosure 210 and the patient. The goggle enclosure 210 can extend about the eye 100, such as the entire exposed anterior portion of the eye 100. The goggle enclosure 210 can include a seal material 214, such as can be located around the perimeter of the goggle enclosure 210. The goggle enclosure 210 can be positioned over the eye 100, such that the seal material 214 can be located against the patient, such as to form a gasket between the goggle enclosure 210 and the patient. In an example, the goggle enclosure 210 can be located against the skin of the patient to form a gasket between the goggle enclosure 210 and the patient, such as to maintain a desired fluid pressure level within the enclosure using the pump. In an example, the gasket can form a hermetic seal, such as can include an airtight seal, between the cavity 212 and the surrounding environment.

The goggle enclosure 210 can be constructed of a material that can be sufficiently rigid to support or maintain a differential fluid pressure between the cavity 212 and another region, such as the atmosphere surrounding the goggle enclosure 210 or another cavity 212. The differential fluid pressure can include the difference between the fluid pressures in the cavity 212 and the fluid pressure of the ambient environment outside the goggle enclosure 210. A fluid pressure within the cavity 212 can act on the front surface of the eye 100, such as to apply a positive or negative force to the anterior portion of the eye 100, without physically contacting the eye 100 with any non-gaseous fluid body or device, such as to influence IOP in a patient eye 100, such as to decouple IOP from ICP. The goggle enclosure 210 can be constructed from an optically transparent material, such as to allow a patient to see outward through the goggle enclosure 210. The optically transparent material can also allow observation of the eye 100, such as features of the intraocular space, inward through the goggle enclosure 210, such as by a medical professional using a measurement instrument.

Figure 3:
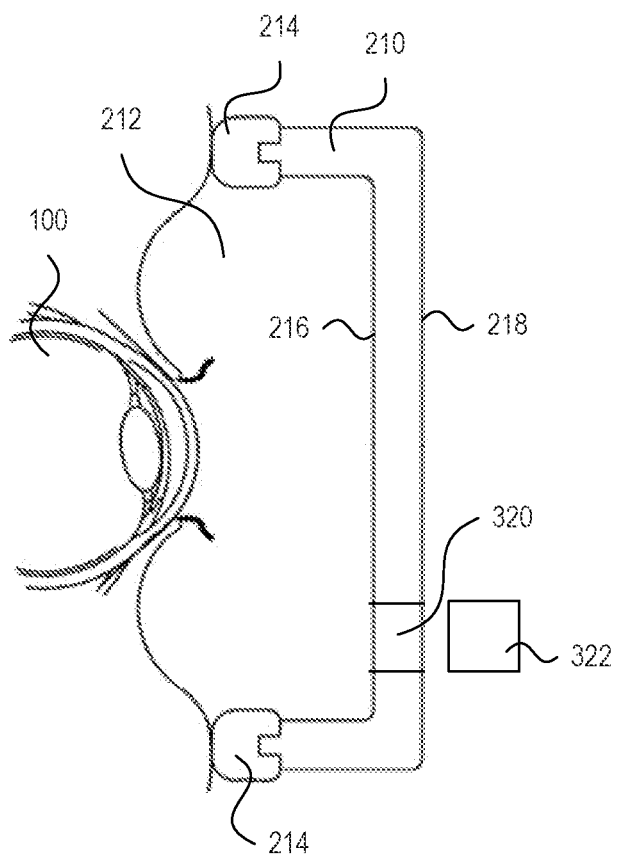
FIG. 3 shows an example of a goggle enclosure including a port.

FIG. 3 shows an example of a goggle enclosure 210 including a port 320. The port 320 can act as a channel between the interior surface 216 and the exterior surface 218 of the goggle enclosure 210, such as to allow fluidic communication between the cavity 212 and the atmosphere surrounding the goggle enclosure 210. The port 320 can allow one or more objects, such as one or more measurement instruments, to be inserted through the port 320, such as to locate the objects in proximity to the eye 100. The port 320 can be located on any surface of the goggle enclosure 210. A first sealing interface (e.g., valve or seal) can be located between the measurement instrument and the port 320, such as to form a hermetic or other seal between the measurement instrument and the port 320. The first sealing interface can include one or more sealing structures, such as one or more of a membrane, sleeve, O-ring, or bellows, such as can be made of one or more sealing materials, such as plastic, rubber, copolymer, or elastomeric materials.

The goggle enclosure 210 can include a stopper 322, such as can be inserted into the port 320 to inhibit or prevent gas or liquid or other fluid from traveling between the cavity 212 and the atmosphere surrounding the goggle enclosure 210. A second sealing interface can be located between the stopper 322 and the port 320, such as to form a hermetic seal between the stopper 322 and the port 320. The stopper 322 can assume any volumetric shape, such as a volumetric shape that can be used in combination with the port 320 and the second sealing interface forms a hermetic seal. The stopper 322 can include a shape with at least one tapered surface, such as a frustum of a cone or conic section, such as the at least one tapered surface can be inserted into the port 320, the tapered surface forming a second sealing interface conformable with the port 320, such as to form a hermetic seal. The stopper 322 can assume a shape that can be formed to the port 320 by the patient. In an example, a quantity of a pliable or moldable material can be formed by hand for insertion into the port 320, such as to form the stopper 322 and the second sealing interface conformable with the port 320. The stopper 322 can be constructed from an optically transparent material, such as to allow a patient to see outward through the stopper 322. The stopper 322 can include a surface covering device, such as a thin film configured to be impermeable to gas, to cover the port 320. The surface covering device can include at least one adhesive surface, such as an adhesive surface configured to adhere to a surface of the goggle enclosure 210, such as at least one of the interior surface 216 or exterior surface 218 of the goggle enclosure 210.

Figure 4:
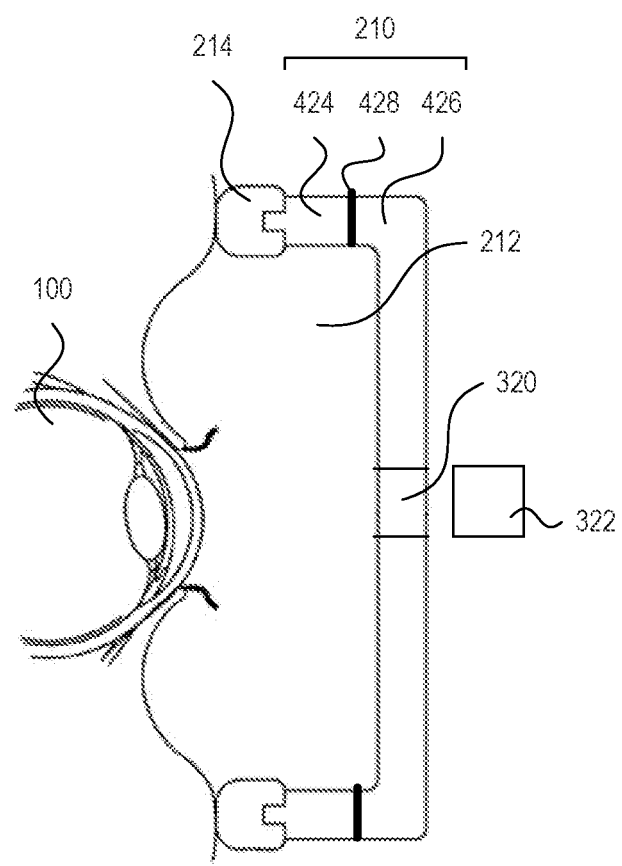
FIG. 4 shows an example of a multi-part goggle enclosure.

FIG. 4 shows an example of a multi-part goggle enclosure 210. The goggle enclosure 210 can include a base 424 and a cap 426 that can join with the base 424 at an interface 428. The base 424 can be sized and shaped to surround the eye 100 and be spaced from the eye 100 without contacting the eye 100. The base 424 can include or define a portion of one or more enclosed cavities 212 when placed against the patient, such as against the eye socket of the eye 100. The base 424 can include a seal material 214, such as can be located around a perimeter of the base 424. The base 424 can be positioned over the eye 100, such that the seal material 214 can be located against the skin of a user, such as to form a gasket between the base 424 and the skin. The base 424 can be secured to a patient, such as to maintain the location of the base 424 over the eye of the patient, such as with at least one of a locating strap, such as a locating strap connected to the base 424 and configured to generally encircle the head of the patient, or an adhesive, such as an adhesive applied to the interface between the base 424 and the patient.

The cap 426 can attach to the base 424, such as at the interface 428, to form the goggle enclosure 210, such as to define the cavity 212 within the goggle enclosure 210. The cap 426 can include a port 320, such as to locate one or more objects such as can include one or more measurement instruments (or portions thereof) in proximity to the eye 100. A measurement instrument can be attached to the cap 426, such as to bring a distal portion of the measurement instrument in proximity to the eye 100. In an example, a measurement instrument can be attached to the cap 426 such as by removing the stopper 322 from the port 320, inserting at least a portion of the measurement instrument into the port 320, and attaching the measurement instrument to the cap 426. The measurement instrument can be attached to the cap 426 such as to create a hermetic seal between the measurement instrument and the cap 426, such as with one or more of a threaded connection, a friction connection, or a fastened connection such as can include one or more fastening devices extending between the base 424 and the cap 426. The one or more measurement instruments can be integral to or attached to the cap 426, for example, the measurement instrument can be permanently affixed to the cap 426.

The interface 428 can include the junction between the base 424 and the cap 426. In an example, the cap 426 can join with the base 424 at the interface 428, such as to form the goggle enclosure 210. The interface 428 can form a hermetic seal between the base 424 and the cap 426, such as to support or maintain a differential fluid pressure between the cavity 212 and another region, such as the atmosphere surrounding the goggle enclosure 210 or another cavity 212. The interface 428 can include a tongue-and-groove joint seal, where the tongue-and-groove joint seal can include a tongue feature integral to the base 424, a groove feature integral to the cap 426, and a continuous seal component, such as an O-ring gasket, seated in the groove feature of the cap 426 and configured to deform and seal against the cap 426 when impinged upon by the tongue feature of the base 424, such as to create the goggle enclosure 210. The interface 428 can include a the tongue-and-groove joint seal including a tongue feature integral to the cap 426, a groove feature integral to the base 424, and a continuous seal component, such as an O-ring gasket, seated in the groove feature of the base 424 and configured to deform and seal against the base 426 when impinged upon by the tongue feature of the cap 426, such as to create the goggle enclosure 210.

The goggle enclosure 210 can affect visualization of the eye 100 by the measurement instrument, such as by changing the focus between the eye 100 and the measurement instrument. The focus between the eye 100 and the measurement instrument can be assisted or corrected, such as using a correction lens that can include at least one of a converging lens, a diverging lens, or a combination of both.

The correction lens can be located between the eye 100 and the measurement instrument, such as between the eye 100 and the goggle enclosure 210, or between the goggle enclosure 210 and the measurement instrument. The correction lens can be attached to the goggle enclosure 210, such as at the interior surface 216, the exterior surface 218, or both. The correction lens can be integrated into the goggle enclosure 210, such as to form part of the structure of the goggle enclosure 210. A correction lens can be integrated into the cap 426, such as to allow a medical professional or other user the opportunity to select an appropriate correction factor for use with a given measurement instrument.

Referring again to FIG. 2, the pump 220 can be in fluid communication with the cavity 212 of the goggle enclosure 210, such as through a tube 222. The pump 220 can affect one or more physical characteristics of the environment of the cavity 212, such as the humidity, the temperature, or the fluid pressure of the environment.

The pump 220 can apply and adjust fluid pressures, such as positive or negative gauge pressures, in the cavity 212 of the goggle enclosure 210, such as to generate a force on the eye. A gauge pressure can include a localized pressure in the cavity 212, referenced from atmospheric pressure outside of the cavity in its immediate surroundings, such as an atmospheric fluid pressure. A positive gauge pressure can include a fluid pressure in the cavity 212 that is greater than atmospheric pressure. A positive gauge pressure in the cavity 212 can exert a force to increase pressure on the anterior portion of the eye 100 relative to the IOP in the eye 100, such as to increase the IOP of the eye 100. A negative gauge pressure can include fluid pressure in the cavity 212 that is less than atmospheric pressure. A negative gauge pressure in the cavity 212 can exert a force to decrease pressure on the anterior portion of the eye 100 relative to the IOP in the eye 100, such as to decrease the IOP of the eye 100.

The pump 220 can include one or more devices that can be selected to apply a gauge pressure to the cavity 212 of the goggle enclosure 210. The pump 220 can include one or more of a compressor pump, a vacuum pump, or a reversible pump, such as to allow the pump 220 to create a positive or negative gauge pressure in the goggle enclosure 210. The pump 220 can include a reservoir, such as to contain a positive or negative gauge pressure, to apply a gauge pressure to the cavity 212 such as without requiring continuous operation of the pump 220. In an example, the pump 220 can operate for a period of time, such as to create a working gauge pressure in the reservoir, and then turn off for a period of time, such as until the gauge pressure in the reservoir crosses a threshold gauge pressure, to maintain the working gauge pressure in the reservoir. The pump 220 can include a reservoir, such as to contain a positive gauge pressure, and a venturi valve, such as in communication with the reservoir and the cavity 212, to generate a negative gauge pressure in the cavity 212, such as by releasing gaseous fluid from the positive gauge pressure reservoir through the venturi valve to create a vacuum including a negative gauge pressure in the cavity 212.

The pump 220 can include a controllable vent in fluid communication with the cavity 212, such as to adjust the gauge pressure within the goggle enclosure 210. The controllable vent can include a valve, such as to regulate the flow of gaseous fluid between the cavity 212 and the surrounding environment, and an actuator connected to the valve and the control circuit 230, such as to open and close the valve in response to a command signal sent from the control circuit 230, such as required to maintain a desired gauge pressure within the cavity 212.

The pump 220 can apply pressures, such as positive or negative gauge pressures delivered to the goggle enclosure 210, to generate a force on the eye. The appropriate duration of gauge pressures applied to the eye can vary depending on the eye condition treated.

Diagnostic regimens, such as for diagnosing eye conditions, such as abnormal eye conditions, can require application of gauge pressures delivered by the pump 220 to the cavity 212 for relatively short periods of time, such as for periods of time measured in seconds or minutes. In an example, a procedure to diagnosis an abnormal eye condition, such as an acute or a chronic abnormal eye condition, such as glaucoma and optic disc edema, can include application of gauge pressures with the apparatus 200 for at least one of 1 second, 2 seconds, 3 seconds, 4 seconds, 5 seconds, 6 seconds, 7 seconds, 8 seconds, 9 seconds, 10 seconds, 11 seconds, 12 seconds, 13 seconds, 14 seconds, 15 seconds, 16 seconds, 17 seconds, 18 seconds, 19 seconds, 20 seconds, 21 seconds, 22 seconds, 23 seconds, 24 second, 25 seconds, 26 seconds, 27 seconds, 28 seconds, 29 seconds, 30 seconds, 31 seconds, 32 seconds, 33 seconds, 34 seconds, 35 seconds, 36 seconds, 37 seconds, 38 seconds, 39 seconds, 40 seconds, 41 seconds, 42 seconds, 43 seconds, 44 seconds, 45 seconds, 46 seconds, 47 second, 48 seconds, 49 seconds, 50 seconds, 51 seconds, 52 seconds, 53 seconds, 54 seconds, 55 seconds, 56 seconds, 57 seconds, 58 seconds, 59 seconds, 60 seconds, 1 minute, 2 minutes, 3 minutes, 4 minutes, 5 minutes, 6 minutes, 7 minutes, 8 minutes, 9 minutes, 10 minutes, or more than 10 minutes.

Therapeutic regimens for acute eye conditions can require application of gauge pressures delivered by the pump 220 to the cavity 212 for relatively short periods of time, such as for periods of time measured in minutes, hours, days, or weeks. In an example, a therapeutic regimen to treat an acute eye condition, such as glaucoma and optic disc edema, can include application of gauge pressures with the apparatus 200 for at least one of 1 hour, 2 hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, and 24 hours, 1 day, 2 days, 3 days, 4 days, 5 days, 6 days, and 7 days, 1 week, 2 weeks, 3 weeks, or 4 weeks.

A therapeutic regimen for acute eye conditions can require application of gauge pressures for intermittent intervals of time, such as periodic or aperiodic intervals. A periodic regimen can include applying therapeutic pressures periodically, such as on a diurnal cycle including applying therapeutic pressures generally during the night, until resolution of the acute eye condition. An aperiodic regimen can include applying therapeutic pressures aperiodically, such as applying therapeutic pressure when an indication of physiological parameter including IOP falls outside a specified range and discontinuing therapeutic pressure when the indication of the physiological parameter falls within a desired level or range.

Therapeutic regimens for chronic eye conditions, such as glaucoma or optic disc edema, can require application of gauge pressures delivered by the pump 220 to the cavity 212 for relatively long periods of time, such as for periods of time measured in days, weeks, months or years. In an example, a therapeutic regimen to treat a chronic eye condition, such as glaucoma and optic disc edema, can include application of gauge pressures with the apparatus 200 for at least one of 1 day, 2 days, 3 days, 4 days, 5 days, 6 days, and 7 days, 1 week, 2 weeks, 3 weeks, and 4 weeks, 1 month, 2 months, 3 months, 4 months, 5 months, 6 months, 7 months, 8 months, 9 months, 10 months, 11 months, and 12 months, 1 year, 2 years, 3 years, 4 years, 5 years, 6 years, 7 years, 8 years, 9 years, or 10 years. In an example, a therapeutic regimen to treat a chronic eye condition, such as glaucoma and optic disc edema, can include the application of gauge pressure delivered to the eye with the apparatus 200 for the lifetime of the patient.

A therapeutic regimen for chronic eye conditions can require application of gauge pressures for intermittent intervals of time, such as periodic or aperiodic intervals. A periodic regimen can include applying therapeutic pressures periodically, such as on a diurnal cycle including applying therapeutic pressures generally during the night to restore axonal transport, for the lifetime of the patient. An aperiodic regimen can include applying therapeutic pressures aperiodically, such as applying therapeutic pressure when an indication of a physiological parameter including IOP falls outside a specified range and discontinuing therapeutic pressure when the indication of the physiological parameter falls within a desired level or range.

The pump 220 can modulate the gauge pressures applied to the one or more enclosures, such as periodically and aperiodically. A periodic gauge pressure can include gauge pressures that vary in magnitude at regular intervals, such as with sinusoidal signals, periodic non-sinusoidal signals, and repeating processes. In an example, the gauge pressure applied to the goggle enclosure 210 can vary in a substantially sinusoidal fashion with a period of approximately 24-hours, such as to compensate for the natural diurnal cycle of IOP in the eye 100 of the patient. A periodic gauge pressure can include gauge pressures that vary in frequency, such as the time between repeating intervals in the periodic signal. In an example, the gauge pressure applied to the enclosure can vary in frequency, such as when the gauge pressure applied to the cavity 212 can vary as a function of cardiac activity, such as heart rate and blood pressure, the cardiac activity measured by a detection device, such as a blood pressure monitoring device.

An aperiodic gauge pressure can include gauge pressures that vary in magnitude at irregular intervals, such as non-periodic signals and non-repeating processes. The gauge pressure applied to the enclosure can vary in an aperiodic fashion that is dependent upon an indication of a body parameter, such as the position of a patient with respect to a coordinate system, the position of the patient measured by an inclinometer. In an example, an indication of a body position can include a change in body position, such as the change in body position of a patient transitioning from a first body position, such as a standing position, to a second body position, such as a sitting or prone position. The gauge pressure applied to the goggle enclosure 210 can vary in an aperiodic fashion that is dependent upon the summation of one or more periodic and aperiodic signals. In an example, the gauge pressure applied to the goggle enclosure 210 can include a periodic component, such as the gauge pressure due to cardiac activity, and an aperiodic components, such as the gauge pressure due to the body position of a patient.

The control circuit 230 can coordinate operation of the apparatus 200, such as the application of fluid pressure to the cavity 212. The control circuit 230 can include a central processor unit (CPU), such as a microcontroller or a microprocessor running one or more programs or algorithms, memory, such as cache memory, a data interface 232, such as including one or more input channels, such as to receive one or more data input signals from one or more components of the apparatus 200, a data output channel, such as to transmit an indication of a processed data signal to another component of the apparatus 200, and a user interface (UI), such as a UI designed to receive an indication of a data input signal, such as information derived from a user interaction with the apparatus 200, and display an indication of a data output signal, such as information regarding operating parameters or conditions of the apparatus 200. The CPU can process one or more data input signals, such as to form a data output signal including a processed composite signal. The control circuit 230 can be used in a control system, such as a feedback control system, to operate or enhance performance of the apparatus 200, such as for at least one of a diagnostic or therapeutic application.

The locating device 240 can secure the goggle enclosure 210 to the patient, such as to maintain the location of the goggle enclosure 210 over the eye 100 of the patient. The locating device 240 can be adjustable, such as to conform with the specific anatomy of the patient. The locating device 240 can include an adjustable strap. The locating device 240 can be integral to the goggle enclosure 210, such as the locating device can be permanently attached to the goggle enclosure 210. The locating device 240 can include an adhesive, such as an adhesive applied to the goggle enclosure 210 and located between the goggle enclosure 210 and the skin of the patient, to attach the goggle enclosure 210 to the skin of the patient. The adhesive can include any material suitable to maintain a seal, such as a hermetic seal, between the cavity 212 and the surrounding environment, such as an adhesive approved for use on skin including a medical grade adhesive.

Figure 5:
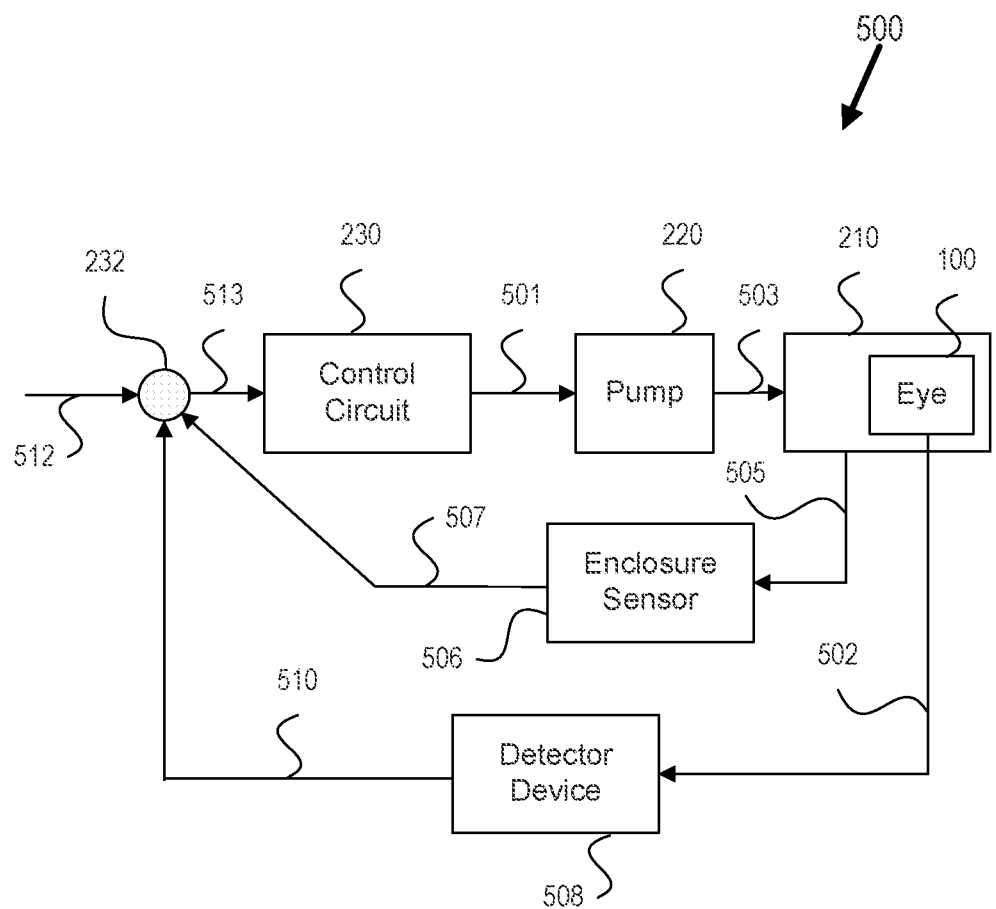
FIG. 5 shows an example of a feedback control system.

FIG. 5 shows an example of a feedback control system 500. The feed control system 500 can be used to control, such as modify, the behavior of the apparatus 200. The feedback control system 500 can include a goggle enclosure 210, a pump 220, a control circuit 230, an enclosure sensor 506, and a detector device 508.

The goggle enclosure 210 can cover the eye 100. An eye characteristic of the eye 100 can be described by an eye parameter 502. The eye parameter 502 can be detected by a detector device 508, such as to convert the eye parameter 502 into an electrical signal that can represent an indication of the eye parameter 502, such a detected eye parameter signal 510. The enclosure pressure parameter 505 can be detected by an enclosure pressure sensor 506, such as to convert the enclosure pressure parameter 505 into an electrical signal that can represent an indication of the enclosure pressure parameter 505, such as a detected enclosure pressure parameter 507. A data interface 232 can receive signals, such as at least one of a detected eye parameter signal 510, a target eye parameter signal 512, or a detected enclosure sensor signal 507. A target eye parameter signal 512 can include an electrical signal representing an indication of a target eye parameter, such as a target value of an eye characteristic. The data interface 232 can be in communication, such as electrical communication, with the control circuit 230. The control circuit 230 can receive the signals from the data interface 232, process the signals from the data interface 232, such as to form a pump control signal 501, and transmit an indication of the pump control signal 501 to the pump 220. The pump 220 can operate in response to the pump control signal 501, such as to generate a fluid pressure level 503, for delivery to the goggle enclosure 210.

Figure 6:
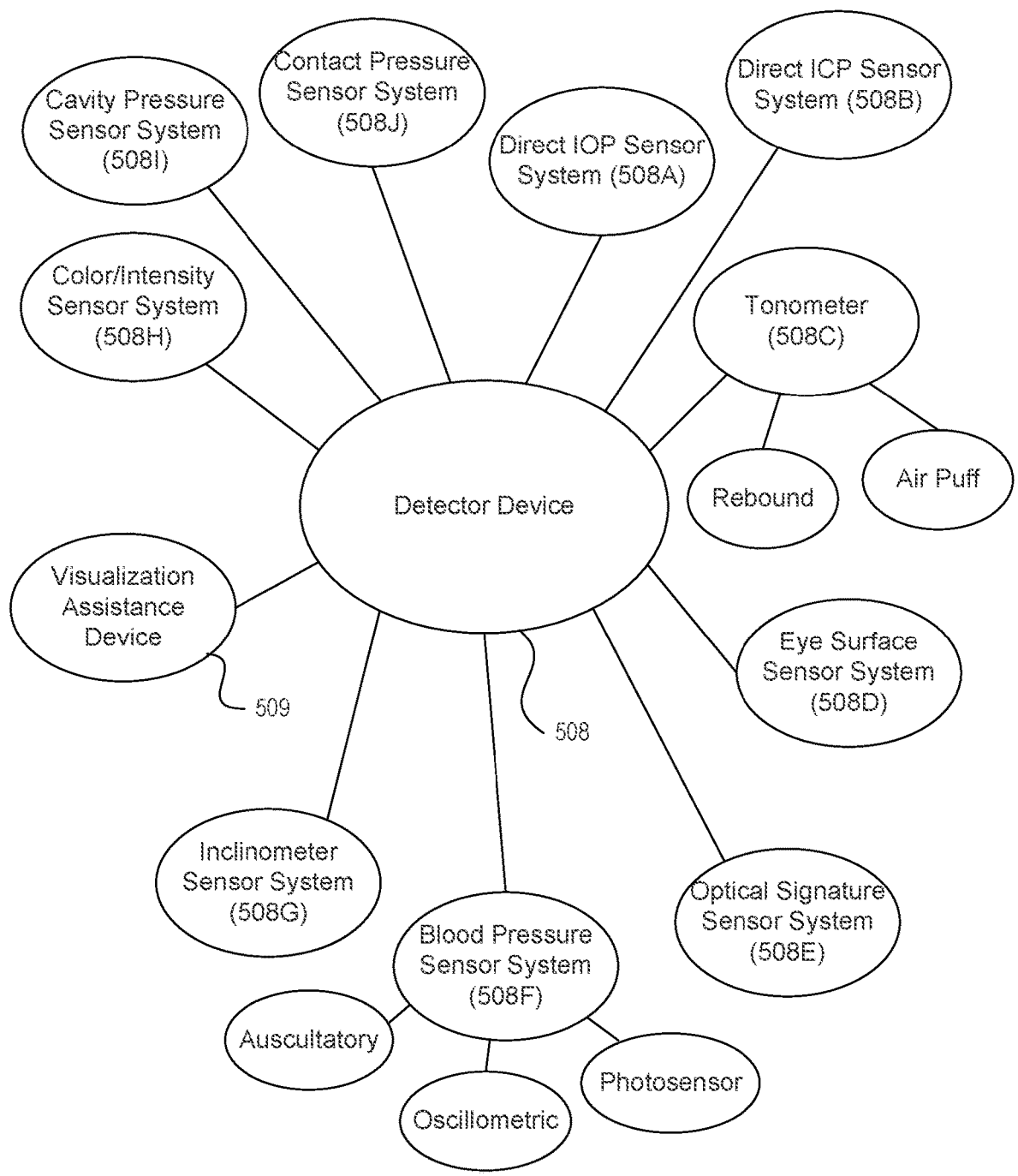
FIG. 6 shows examples of detector devices that can be used in or in combination with the apparatus.

FIG. 6 shows examples of detector devices 508 that can be used in or in combination with the apparatus 200. A detector device 508 can include a pressure sensor or other device that can detect a direct measurement of an intrabody pressure, such as at least one of intraorbital pressure, ICP, IOP, or a relationship between ICP and IOP, such as through detection of a parameter related to at least one of an intraorbital pressure, ICP or IOP. In an example, the relationship between ICP and IOP can include an indication of at least one of SVP, a cup-to-disc ratio, a change in radius of curvature of the eye 100, such as flattening of the posterior globe, or a change in axial length of the eye 100, such as a change in the distance between an anterior surface of the eye 100 and a posterior surface of the eye 100. The sensor system 508A can be implanted or located within the humor of the eye 100, such as the viscous or aqueous humor, or anchored to an interior surface of the eye 100. The sensor system 508A can be configured to be used in or in combination with an intraocular lens, such as a stand-alone sensor in proximity to an intraocular lens, or as a sensor integrated into a replacement intraocular lens and implanted into the eye 100, such as during cataract surgery.

The sensor 508A can include a passive sensor or non-powered sensor, such as a manometer sensor system. The manometer sensor system can include a manometer pressure sensor and a manometer data receiver. The manometer pressure sensor can include a sensing device, such as a sensing device that can be integrated into an implantable ocular replacement lens and implanted within the intraocular space, such as the manometer pressure sensor can be visible through the cornea. The manometer pressure sensor can include a meniscus, such as an interface between at least two working fluids of the manometer. In an example, the meniscus can be located at a first level, such as when subjected to a first fluid pressure including a first IOP, and located at a second level, such as when subjected a second fluid pressure including a second IOP, such as the first and second fluid pressures are different.

The manometer data receiver can include an imaging device, such as a VAD 509. The VAD 509 can include a camera system 509E, such as at least one of a fundus camera, a video camera, or a smartphone camera. The camera system 509E can be attached to a frame, such as the goggle enclosure 210. The camera system 509E can be located in proximity to the patient eye 100, such as to establish a clear line of sight between the camera system 509E and the manometer pressure sensor, such as to be visible through the cornea. For example, the imaging device can include or be similar to one or more of a commercially available device, such the device from Apple Inc. (Cupertino, Calif.) offered for sale under the trademark GOOGLE GLASS®. In an example, the camera system 509E can be located in the cavity 212 of the goggle enclosure 210, such as with the camera directed towards the eye 100 and configured to focus and visualize the pressure display indicator of the sensor, such as the meniscus of the manometer pressure sensor.

The sensor 508A can include an active or powered sensor, such as a wireless transmitting sensor system. The system can include a pressure transducer and pressure transducer local interface. The pressure transducer can include at least one of a battery-powered sensor or a transcutaneously-powered transducer, such as can be implanted within the intraocular space to detect an indication of an eye characteristic, such as IOP. The pressure transducer local interface can be in electrical communication with the pressure transducer, such as to wirelessly transmit energy to the pressure transducer, such as to power the pressure disk sensor, and wirelessly receive data from the pressure transducer, such as an indication of IOP. For example, the sensor 508A can include or be similar to one or more of the eye pressure measurement system and devices from Implandata Ophthalmic Products GmbH (Hannover, Germany) offered for sale under the trademark EYEMATE®. In an example, the pressure transducer local interface can be integrated into the apparatus 200, such as located in the goggle enclosure 210. The goggle enclosure 210 can locate the pressure transducer local interface in proximity to the pressure transducer, such as to allow for wireless communication between the pressure transducer and the pressure transducer local interface.

The detector device 508 can include a direct ICP sensor 508B, such as to detect an indication of ICP, such as by direct exposure to ICP. The sensor 508B can be located within or in communication with a portion of the body exposed to ICP, such as a ventricle of the brain or the spinal cord. The sensor 508B can include a powered ICP sensor, such as at least one of a battery-powered sensor or a transcutaneously-powered sensor, such as can be at least partially implanted within the body to sense an indication of ICP, and an indicator capture device, such as a device to wirelessly collect data about the indication of ICP from the powered sensor. For example, the sensor 508B can include or be similar to one or more of the devices and methods described in the paper "Laboratory testing of the Pressio intracranial pressure monitor", by Allin, et al., published in Neurosurgery, Vol. 62, #5, May 2008, p. 1158. In an example, the sensor 508B can be implanted in the patient, such as a ventricle of the brain through a surgical approach, and connected electrically to the control circuit, such as through the data interface 232.

The detector device 508 can include a device that detects an indirect measurement of an intrabody pressure, such as at least one of intraorbital pressure, ICP, IOP, or a relationship between ICP and IOP, such as through detection of a parameter related to at least one of an intraorbital pressure, ICP or IOP.

The detector device 508 can include an indirect IOP sensor, such as a tonometer 508C, or other such device that can detect an indication of IOP through detection of an indication related to IOP. Applanation tonometry can infer IOP based upon the applied force needed to flatten (or applanate) a portion of the cornea. An applanation tonometer can include a non-contact tonometer, such as an air-puff tonometer or an ocular response analyzer. An applanation tonometer can include a contact tonometer, such as a Goldmann tonometer, a Perkins tonometer, a dynamic contour tonometer, an electronic indentation tonometer, a rebound tonometer, a pneumatonometer, an impression tonometer, a non-corneal tonometer, or a transpalpebral tonometer.

Figure 7:
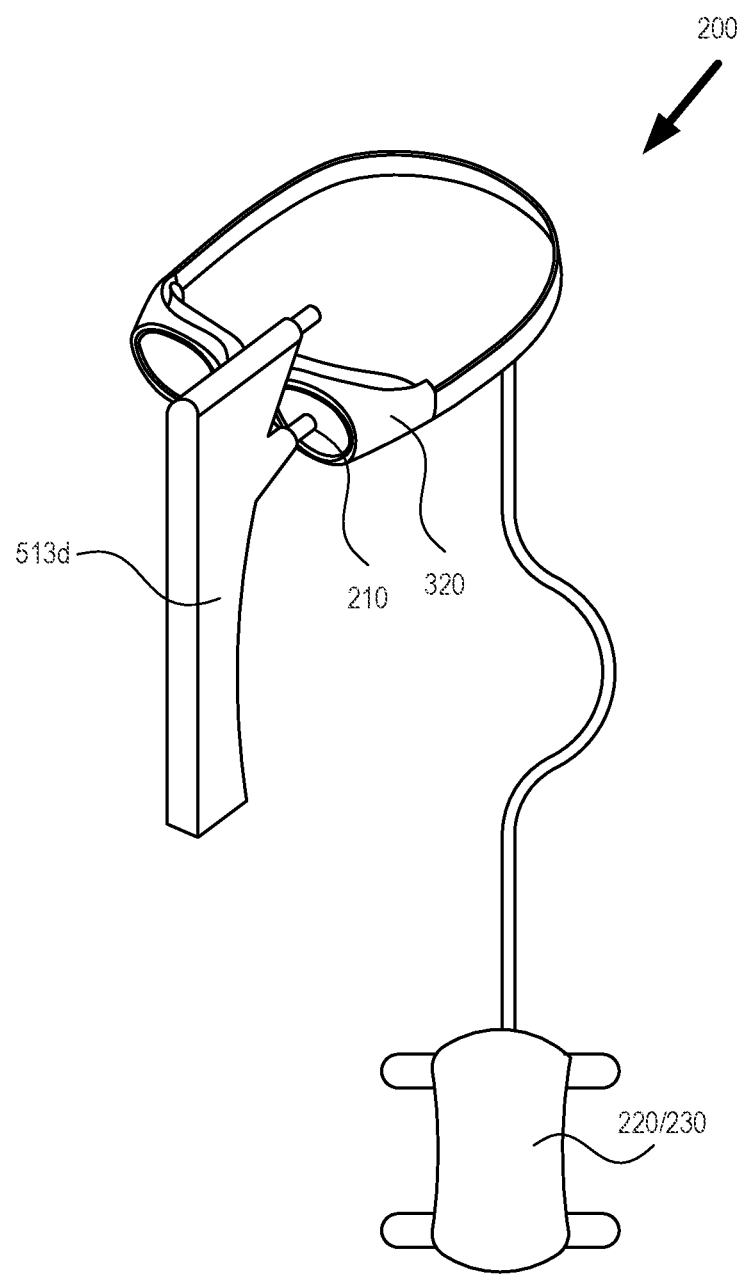
FIG. 7 shows an example of a tonometer included in or used in combination with an example of an apparatus.

FIG. 7 shows an example of a tonometer 508C included in or used in combination with an example of an apparatus 200. The goggle enclosure 210 of the apparatus 200 can include a port 320 through which a portion of the tonometer 508C can extend, such as to locate such portion of the tonometer 508C in close proximity to the eye 100. The port 320 can include a valve or sealing interface, such as to form enough of a hermetic seal between the port 320 and the tonometer 508C, so that a gauge pressure can be maintained within the cavity 212 of the goggle enclosure 210 while operating the tonometer 508C to measure the IOP of the eye 100. The tonometer 508C can include a contact tonometer, such as a rebound tonometer including the rebound tonometer device from Icare Finland Oy (Espoo, Finland) offered for sale under the trademark ICARE™.

The tonometer 508C can include a non-contact tonometer, such as an air puff tonometer. The air puff tonometer can include an actuating element, such as can provide a jet of pressurized air applied to the surface of the eye 100. When used in or in combination with the apparatus 200, such as an apparatus 200 with a cavity 212 at a first fluid pressure, the air puff tonometer can be configured to generate a jet of pressurized air, such as a jet of pressurized air at a second fluid pressure that can be selected relative to (e.g., to be greater than) the first fluid pressure applied to the cavity 212, such as to applanate the eye 100 in the presence of the first fluid pressure applied to the cavity 212. For example, the tonometer 508C can include or be similar to the air puff tonometer device from Topcon Medical Systems Incorporated (Oakland, N.J., USA) offered for sale under the trademark CT-80 NON-CONTACT COMPUTERIZED TONOMETER™. In an example, the goggle enclosure 210 can integrate with the CT-80, such as to locate the measuring nozzle and measuring window within the goggle enclosure 210.

The detector device 508 can include an eye surface sensor system 508D, such as a device that can be in substantial contact with the eye 100, such as the scleral or corneal surface of the eye 100. The eye surface sensor 508D can measure a deformation of the surface of the eye 100. Such deformation can be correlated to an indication of an intrabody pressure, such as IOP. The eye surface sensor system 508D can be included in, or used in combination with a contact lens, such as a corrective or cosmetic contact lens. The eye surface sensor 508D can include a wirelessly powered microsensor device attached to a contact lens-type device, such as to detect one or more circumferential changes of the surface of the eye 100, such as due to changes in one or more intrabody pressures of the eye 100, such as can include IOP. The eye surface sensor 508D can include an indicator capture device, such as an antenna or other transmitter and an indicator capture interface circuit, such as can include a receiver to wirelessly collect information about one or more indications of one or more eye characteristics of the eye 100 sensed from the eye surface sensor. For example, the eye surface sensor system 508D can include or be similar to a contact lens-based detection system device from Sensimed AG (Lausanne, Switzerland) offered for sale under the trademark SENSIMED TRIGGERFISH®. In an example, the indicator capture interface circuit can be integrated into the apparatus 200, such as located in the goggle enclosure 210. The goggle enclosure 210 can locate the indicator capture interface circuit in proximity to the pressure transducer, such as to allow for wireless communication between the indicator capture device and the indicator capture interface circuit.

The detector device 508 can include or be used in combination with an optical signature sensor system 508E, such as can include an implant device that can be located within the eye 100, such as in at least one of the aqueous or viscous humor, and a detector unit. The implant device can include a sensor, such as can include a pressure-sensitive nanophotonic structure. The detector unit can be integrated into the goggle enclosure 210, such as in proximity to the implant device, such as in a direct line of sight with the implant device. The detector unit can include an energy source such as can excite the implant device, such as with electromagnetic energy, such as from at least one of the ultraviolet, visible, or near infrared frequency ranges, and receive reflected electromagnetic energy from the implant device. The received reflected electromagnetic energy can include an indication of an eye parameter, such as IOP. The received reflected electromagnetic energy can be processed by a sensor interface control circuit, such as to detect one or more changes in the optical signature of the light, such as due to a change in the IOP of the eye 100.

The detector device 508 can include a blood pressure sensor system 508F, such as can include a device that can detect one or more indications of blood pressure, such as by at least one of auscultation, oscillometric, or photoplethysmography (or PPG) detection. An indication of blood pressure can include one or more indications of one or more cardiac cycle blood pressure parameters, such as can include systolic pressure, diastolic pressure, orbital pressure, or episcleral venous pressure, and one or more related parameters, such as heart rate. Orbital pressure can include the pressure, such as the contact pressure, between the eye 100 and the eye socket, such as the bones that form the eye socket, such as the frontal, lacrimal, ethmoid, zygomatic, maxillary, palatine, and sphenoid bones.

An auscultation device can be included and used to detect one or more sounds originating from within the body, such as can be generated by the cardiac cycle including at least one of heart beat or blood flow in blood vessels. An auscultation device can include at least one of a stethoscope, such as an acoustic or electronic stethoscope, or a stethoscope used in or in combination with a sphygmomanometer, such as a mercury or aneroid sphygmomanometer.

An oscillometric device can be included and used to detect vibration in a blood vessel, such as vibration due to flow of blood in a blood vessel. An oscillometric device can include one or more sensors, such as at least one of an electrostatic sensor or a capacitive sensor, and can be located in in contact with or in proximity to the patient, such as to detect vibration, such as due to blood flow in a blood vessel of the patient.

A PPG device can be included and used to detect reflectance of light, such as from the skin of a patient. A PPG device can include a light radiation source, such as a source of light that can irradiate the skin of a patient, and a light radiation receiver, such as a receiver to receive reflected light from the skin of the patient. The light radiation source can generate light at a selected wavelength, or at different wavelengths, such as at least one of a green light, such as with a wavelength of about 525 nanometers, or an infrared light, such as with a wavelength of about 800 nanometers. For example, the PPG device can include or be similar to the device from Apple Inc. (Cuppertino, Calif.) offered for sale under the trademark APPLE WATCH®. In an example, the APPLE WATCH can be in electrical communication with the apparatus 200, such as through a wireless interface communicating with the control circuit 230.

The detector device 508 can include an inclinometer sensor 508G. An inclinometer sensor 508G can provide an indication of an eye parameter, such as an indication of one or more hydrostatic pressures associated with the eye 100, such as a differential hydrostatic pressure. The inclinometer sensor 508G can include a combination of sensors, such as at least one of a tilt sensor, an accelerometer, a multi-axis inclinometer, or a multi-axis accelerometers. The inclinometer sensor 508G can indicate a patient's relative position with respect to a more global reference frame, such as the ground. In an example, an inclinometer sensor 508G can indicate an angle of 0 degrees when the patient is standing upright relative to the ground (e.g., the patient is perpendicular to the ground) and an angle of 90 degrees when the patient is lying down (e.g., the patient is parallel to the ground). The inclinometer sensor 508G can indicate the patient's relative position with respect to a local reference frame, such as an anatomical reference frame, such as can include sagittal, coronal, and transverse planes. In an example, an inclinometer sensor 508G can indicate an angle of 0 degrees when the patient is in a supine position (e.g., lying down, face up) and an angle of 180 degrees when the patient is in a prone position (e.g., lying down, face down).

The detector device 508 can include a color/intensity sensor system 508H. A color/intensity sensor system can include an imaging system, such as a visualization assistance device 509, such as a camera system 509E, and a color/intensity processing software, such as running on the CPU of the control circuit 230. In an example, the camera system 509E can perform a visualization of a portion of the eye 100, such as a first and subsequent visualizations, that can include information about an indication of at least one of color or color intensity, such as a digital image. The camera system 508E can digitize an image, such as a first and subsequent digital images, such as for processing, and transmit the digitized image, such as to the control circuit 230. The difference between an indication, such as an indication of at least one of color or color intensity, can be determined, such as with at least one of a comparator circuit or a color/intensity processing software, such as between a first and subsequent digital image, and the difference between the indication stored, such as with an electronic storage device.

The detector device 508 can include a pressure sensor, such as a cavity pressure sensor 508I, to detect fluid pressure, such as in a confined volume. The cavity pressure sensor 508I can include a sensing element such as can include at least one of a piezoelectric material, a piezoresistive material, a capacitive material, such as a sensor based on the Hall effect, or a resistive material, such as a strain gauge sensor.

The detector device 508 can include a pressure sensor, such as a contact pressure sensor system 508J, to detect one or more surface pressures. The contact pressure sensor system 508J can include a contact transducer, such as at least one of piezoresistive, piezoelectric, capacitive, optical, potentiometric, or electromagnetic sensing element, and a wireless signal interface, such as to power the contact transducer and detect signals from the transducer. The contact pressure sensor 508J can include at least one of a strain sensor or a capacitive mat. The capacitive mat can include a first conductive member, a second conductive member in proximity to the first conductive member, and an insulating member, such as a dielectric material located between the first and second conductive members. As the first conductive member approaches the second conductive member, such as due to the influence of opposing contact forces, such as forces generated between the sclera 122 and the eye socket, a change in capacitance between the first and second conductive members can be detected, such as a change proportional to the distance between the first and second conductive members. The contact pressure sensor system 508J can detect an indication of blood pressure, such as by detecting an indication of a contact pressure between two surfaces, such as variations in force due to systolic and diastolic pressure. The contact pressure sensor system 508J can be placed between the sclera 122 and the eye socket, such as to detect orbital pressure. Orbital pressure can include one or more forces applied by the eye 100 to the eye socket due to blood pressure in the eye 100, such as can vary in time, such as due to systolic and diastolic blood pressures.

Figure 8:
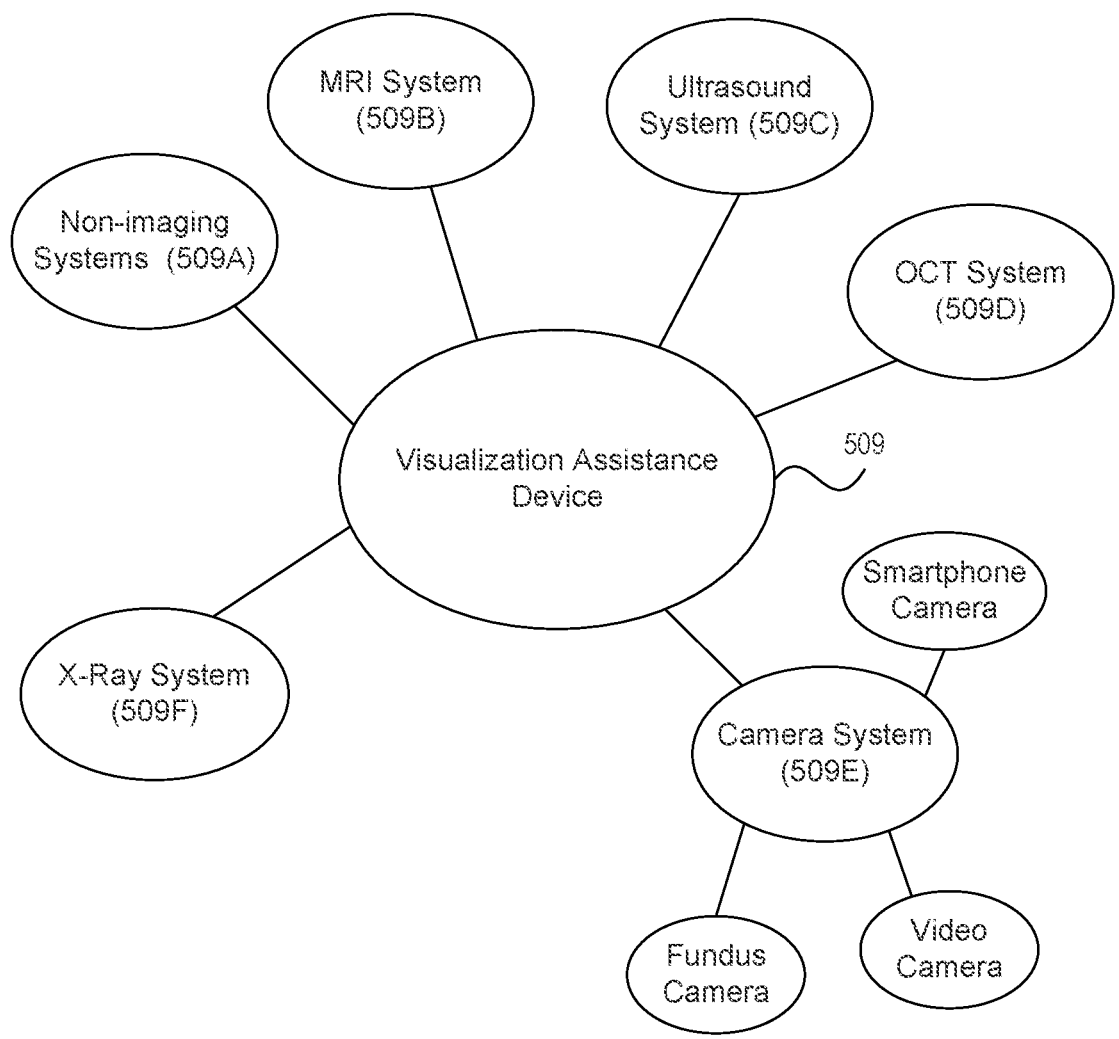
FIG. 8 shows examples of a visualization assistance device (or VAD) that can be included in or used in combination with the apparatus.

FIG. 8 shows examples of a visualization assistance device 509 (or VAD) that can be included in or used in combination with the apparatus 200, such as to help perform a visualization of the patient eye 100. The VAD 509 can visualize a portion of the eye, such as at different fluid pressures within the enclosure, such as to monitor an indication of an eye characteristic. A visualization can include a representation of a physical structure, such as at least one of an indication of a physical structure of the patient eye 100 or an indication of an eye characteristic of the patient eye 100, such as an image including an analog or digital image. The image can be undocumented, such as the image can be perceived by a human observer without storing the image, such as to computer memory. The image can be documented, such as the image can be perceived and stored, such as to computer memory, by an observer with the use of an imaging device, such as a VAD 509

The VAD 509 can include a system that can receive an image, such as with a visualization detector, and convert the received image to a signal, such as a received electrical signal. The received electrical signal can include an array of discrete values, such as pixels and voxels, representing the received image, such as a digital image. The VAD 509 can process, such as digitally process, a visualization, such as one or more images, with an image processor circuit, such as a VAD processor circuit, such as a VAD processor circuit integral to the VAD 509.

The VAD 509 can include a lens or other device to help a human observer's eye to detect an indication of an eye parameter, such as a cup-to-disc ratio of a patient eye 100. The eye of an observer can detect a change of an indication of a physiological parameter, such as by comparing a first cup-to-disc ratio of a patient eye 100 due to a first gauge pressure applied to the patient eye 100 with the apparatus 200 to a second cup-to-disc ratio of a patient eye 100 due to a second gauge pressure applied to the patient eye 100 with the apparatus 200, such as the observer can estimate the change in the indication of the physiological parameter due to the change in pressure applied by the apparatus 200. The VAD 509A can include one or more devices, such as at least one of a magnifier, such as a bio-microscope, or an ophthalmoscope, such as with a light source, to enhance detection of an indication of an eye characteristic.

The VAD 509 can include a magnetic resonance imaging (MRI) system 509B. The MRI system 509B can include an MRI visualization detector such as can include one or more sensors that can detect radio frequency (RF) energy, such as energy in a frequency range from about 20 kilohertz to about 300 megahertz. The MRI system 509B can be used create a two-dimensional or three-dimensional image of the eye.

The VAD 509 can include an ultrasound system 509C. The ultrasound system 509C can include an ultrasound visualization detector such as can include one or more sensors, such as at least one of a piezoelectric transducer, a piezoelectric transceiver, or an array of piezoelectric transducers and transceivers, that can detect ultrasonic energy, such as energy in a frequency range from about 20 kilohertz to about ten gigahertz.

The VAD 509 can include an optical coherence tomography (OCT) system 509D. The OCT system 509D can include a visualization detector such as can include one or more sensors, such as can include at least one of a charge coupled device (CCD) or a complementary metal-oxide semiconductor (CMOS) devices, to detect visible light, such as from an imaged object, and convert the light into electrical signals suitable for electronic storage, such as in an array of pixels. In an example, axonal transport can be imaged, such as with an OCT system 509D. In an example, an axonal transport imaging device can include at OCT system 509D. In an example, a laminar cribrosa position or shape detection device can include an OCT system 509D. In an example, an OCT system 509D, such as a phase-variance OCT system, can detect blood flow, such as change in blood flow velocity, in a vessel.

The VAD 509 can include a camera system 509E. The camera system 509E can include at least one of a fundus camera, a video camera, or a smartphone camera, such as a smartphone with video capture capability. In an example, axonal transport can be imaged, such as with a fluorescein angiography technique, such as by illuminating the retina of an eye 100, such as with light at a wavelength of 490 nanometers, and capturing the resulting image with a camera system 509E. In an example, an axonal transport imaging device can include a camera system 509E.

The VAD 509 can include an X-ray system 509F, such as to detect energy at one or more frequencies greater than visible light, such as in a frequency range greater than about 300 terahertz, and convert the energy into electrical signals suitable for recording, such as in an array of pixels. In an example, an imaging device can include at least one of an X-ray computed tomography (X-ray CT) or a computerized axial tomography (CAT) system.

Figure 9:
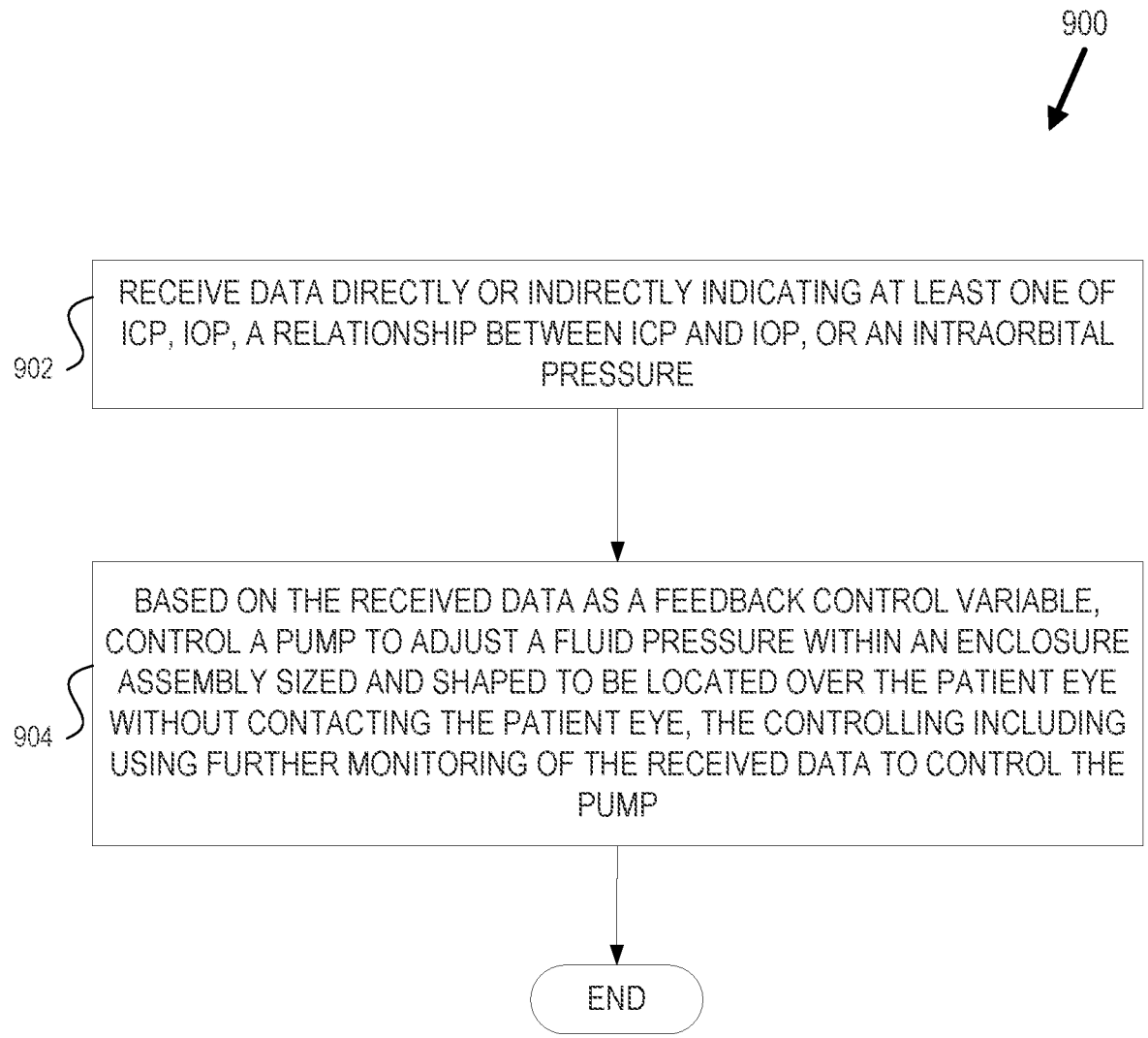
FIG. 9 shows an example of a method for using the apparatus.

FIG. 9 shows an example of a method 900 for using the apparatus 200, such as to apply a fluid pressure to an eye 100 within the cavity 212 of the goggle enclosure 210. At 902, the apparatus 200 can receive data directly or indirectly indicating at least one of an intraorbital pressure, ICP, IOP, or a relationship between ICP and IOP. The received data can be detected from a patient, such as a patient wearing the apparatus 200 including an goggle enclosure 210 sized and shaped to be seated on an eye socket of an eye 100 to provide one or more cavities 212 within the goggle enclosure 210 that extend about an entire exposed anterior portion of the eye 100. The apparatus 200 can receive data at the control circuit 230, such as through the data interface 232, such as from a detector device 508 or a storage device, such as an electronic storage device.

At 904, the apparatus 200 can, based on the received data as a feedback control variable, control the pump 220, such as to adjust a fluid pressure within the goggle enclosure 210 sized and shaped to be located over the patient eye 100 without contacting the patient eye 100, where controlling the pump 220 can include further monitoring of the received data to control the pump 220.

Receiving data directly indication at least one of an intraorbital pressure, ICP, IOP, or a relationship between ICP and IOP, can include receiving, such as from a detector device 508, an indication of a sensed IOP with a fluid pressure sensor previously implanted within an intraocular space of the eye, such as a direct IOP sensor system 508A. In an example, the manometer data receiver, such as the camera system 509E, can receive a first image of a first manometer level at a first pressure, such as at a CCD or CMOS device, and a second image of a second manometer level at a second pressure. The camera system 508E can digitize the first and second images, such as for processing, and transmit the digitized first and second images, such as to the control circuit 230. The difference between the first manometer level and the second manometer level can include an indication, such as a direct indication, of the sensed IOP of the eye 100, such as due to the second fluid pressure. In an example, the pressure transducer local interface can receive a signal, such as a wireless signal, from the pressure transducer, such as implanted in the intraocular space of the patient eye 100. The pressure transducer local interface can digitize the wireless signal, such as for processing, and transmit the digitized wireless signal, such as to the control circuit 232. The wireless signal can include an indication, such as a direct indication, of the sensed IOP of the eye 100.

Receiving data directly indicating at least one of an intraorbital pressure, ICP, IOP, or a relationship between ICP and IOP, can include receiving, such as from a detector device 508, an indication of a sensed ICP sensed by a fluid pressure sensor previously placed in fluid communication with a cerebrospinal region, such as the direct ICP sensor system 508B. In an example, the indicator capture device can receive a signal, such as a wireless signal, from the powered ICP sensor, such as implanted in the ventricle of the brain of the patient eye 100. The indicator capture device can digitize the wireless signal, such as for processing, and transmit the digitized wireless signal, such as to the control circuit 230. The wireless signal can include an indication, such as a direct indication, of the sensed ICP of the patient.

Receiving data directly indicating at least one of an intraorbital pressure, ICP, IOP, or a relationship between ICP and IOP, can include receiving, such as from a detector device 508, an indication of a sensed intraorbital pressure sensed by a sensor previously placed in fluid communication with an orbit of the skull, such as a contact pressure sensor system 508J. In an example, the contact pressure sensor system 508J can include a capacitive mat. A signal, such as a signal proportional to orbital pressure, can be received, digitized, and transmitted by the wireless signal interface to the control circuit 230. The wireless signal can include an indication, such as a direct indication, of the sensed intraorbital pressure of the patient.

Receiving data indirectly indicating at least one of intra-orbital pressure, ICP, IOP, or a relationship between ICP and IOP, can include receiving, such as from a detector device 508, an indication of at least one of a systemic blood pressure, a differential hydrostatic pressure, or an orbital pressure, such as a sensor system including a wireless sensor and a wireless sensor receiver. The sensor system can include at least one of a blood pressure sensor system 508F and an inclinometer sensor system (508G). In an example, the wireless sensor receiver can receive a signal, such as a wireless signal, from the wireless sensor, such as in contact with the patient, such as the skin of the patient. The wireless sensor receiver can digitize the wireless signal, such as for processing, and transmit the digitized wireless signal, such as to the control circuit 230.

Receiving data indirectly indicating at least one of intra-orbital pressure, ICP, IOP, or a relationship between ICP and IOP, can include receiving, such as from a VAD 509, an indication of displacement, such as from a reference datum. An indication of displacement can include an indication of at least one of an eye characteristic, a translaminar pressure difference (TPD), such as a cup-to-disc ratio, an SVP, an induced venous pulsation, or at least one of a lamina cribrosa shape or position, such as referenced from a fixed datum. The sensor system can include an OCT system 509D. In an example, the OCT system can receive an indication of displacement, such as through detection of reflected light. In an example, the OCT system 509D can emit light, such as a specific wavelength of light, receive reflected light, such as from a distant surface, with a detector, such as at least one of a CCD or CMOS detector. The OCT system can digitize the detected reflected light, and transmit the digitized signal, such as to the control circuit 230.

Receiving data indirectly indicating at least one of intra-orbital pressure, ICP, IOP, a relationship between ICP and IOP, can include receiving, such as from a user, an indication of body parameter, such as at least one of a body mass index (BMI) and chronological age, such as to calculate an estimate of intraorbital pressure, ICP, IOP, or a relationship between ICP and IOP. In an example, the user interface (or UI) of the control circuit 230 can include a data input device, such as a keypad, such as to allow the control circuit 230 to receive data from a user. The received data can be stored, such as in RAM, such as for use in operation of the apparatus 200.

Receiving data indirectly can include receiving, such as from a detector device 508, an indication of an eye blood vessel characteristic including the caliber of a blood vessel, such as with an OCT system 509D. The OCT system 509D can visualize a portion of the patient eye 100, such as a portion including at least one blood vessel including a venous blood vessel, through the goggle enclosure 210, such as an enclosure constructed from an optically transparent material, while the patient eye 100 can be subjected to a fluid pressure applied to the cavity 212 with the pump 220. Optical disturbances introduced by the goggle enclosure 210 can be mitigated with the use of a correction lens, such as at least one of a correction lens placed between the OCT system 509D and the goggle enclosure 210, a correction lens placed between the goggle enclosure 210 and the patient eye 100, or a correction lens integrated into the goggle enclosure 210.

The OCT system 509D can visualize changes in an indication of the caliber of a blood vessel, such as changes in response to adjusting fluid pressure in the goggle enclosure 210. Adjusting fluid pressure in the goggle enclosure 210 can cause the blood vessel to deform, such as to distend under decreasing fluid pressure in the goggle enclosure 210 and collapse under increasing fluid pressure in the goggle enclosure 210. The OCT system 509D can perform a visualization, such as one or more visualizations, of the blood vessel, such as one or more visualizations performed while adjusting fluid pressure in the goggle enclosure 210, and capture representations of the visualization, such as in a digital image.

The OCT system 509D can detect changes, such as in an indication of the caliber of a blood vessel, such as by comparing a first digital image of a portion of the patient eye 100, such as due to a first fluid pressure in the goggle enclosure 210, and a subsequent digital image of a portion of the patient eye 100, such as due to a subsequent fluid pressure in the goggle enclosure 210, such as the first and subsequent fluid pressures are different. The OCT system 509D can determine an eye characteristic change criterion, such as collapse of a blood vessel visualized in the patient eye 100, based on detected changes in an indication of the caliber of the blood vessel.

Analyzing can include detecting a change, such as a change identified by comparing images, such as a first digital image due to a first fluid pressure and a subsequent digital image due to a subsequent fluid pressure, such as a subsequent fluid pressure sufficient to initiate collapse of the blood vessel. Processing, such as image processing, can include using a comparator circuit. The comparator circuit can compare first and subsequent digital images, such as corresponding array elements in the digital images, such as at least one of pixels or voxels. The comparator circuit can determine a difference, such as between the first and subsequent digital images, such as to identify changes between a blood vessel characteristic of the first and subsequent digital images.

Receiving data indirectly can include receiving, such as from a detector device 508, an indication of a translaminar pressure difference (TPD), such as an indication of a cup-to-disc relationship including a cup-to-disc ratio. Visualizations of the cup-to-disc ratio can be received using a VAD 509, such as at least one of an MRI system 509B, an ultrasound system 509C, an OCT system 509D, a camera system 509E, such as a fundus, video, or smartphone camera 509E, or an X-ray system 509F.

The cup-to-disc ratio can indicate the relative magnitudes of IOP and ICP in a patient eye 100, such as a ratio of IOP to ICP. The relationship between IOP and ICP can be estimated, such as by a calibration of the cup-to-disc ratio of the eye 100, such as each patient eye 100, such as by varying applied fluid pressure levels in the apparatus 200, and performing visualizations of the eye 100, such as at the varying applied fluid pressure levels. In an example, the IOP of a patient eye 100 can be varied, such as with the apparatus 200, by applying incremental fluid pressure steps to the goggle enclosure 210, such as by incrementally increasing or decreasing fluid pressure in the goggle enclosure 210. At each incremental fluid pressure step, a visualization of the cup-to-disc ratio can be performed, such as with at least one of a VAD 509, and each visualization can be processed, such as by storing the visualization to a storage device. Assuming ICP remains relatively constant during the calibration, the relationship between IOP and ICP, such as the cup-to-disc ratio, can be identified from the incremental visualizations for the patient eye 100, such as by identifying the cup-to-disc ratio of each visualization stored, and processed, such as by the control circuit 230, into a mathematical equation, such as relating ICP to IOP, based on the data obtained during the calibration.

Controlling the pump 220 can include setting a therapeutic pressure in the goggle enclosure 210, such as can include establishing the amount of therapeutic pressure, or the therapeutic pressure level, to apply to the goggle enclosure 210 to treat an abnormal eye condition. Establishing the therapeutic pressure level can include processing a received indication of an eye characteristic, receiving a target value for the indication of the eye characteristic, determining the difference between the received indication of the eye characteristic and the received target value of the indication of the eye characteristic, selecting a therapeutic pressure level based on the difference between the received indication of an eye characteristic and the received target values of an indication of the eye characteristic, and transmitting a control signal to a device operable to deliver the therapeutic pressure level to the goggle enclosure 210, such as the pump 220.

Processing a received indication of an eye characteristic can include assigning a value, such as a numerical value, to a received indication of the eye characteristic. The numerical value of the received indication can include a value detected by a detector device 508 that has been calibrated, such as with a calibration standard. In an example, the received indication of the eye characteristic, such as the IOP of an eye 100, can include the value of IOP detected with a detector device 508, such as a rebound tonometer that has been calibrated with a calibration standard including at least one of a force standard or a displacement standard. The numerical value of the received indication of the eye characteristic can be weighted, such as with a numerical factor to convert the received indication from a first set of parameter units to a second set of parameter units, such as with the CPU of the control circuit 230. In an example, the received indication can be received at a first input channel of the control circuit 230 with a first set of parameter units, such as millivolts or milliamps, and converted to a second set of parameter units, such as pounds-per-square-inch (psi) or millimeters of mercury (mmHg), by weighting the received indication with a numerical factor representing a conversion factor between the first and second set of parameter units, such as mmHg per millivolt (mmHg/mv), with the CPU of the control circuit 230.

Processing a received indication of an eye characteristic can include calculating a composite indication of an eye characteristic, such as where the composite indication can include a function of one or more received indications. The composite indication can be calculated with a processing unit, such as the CPU of the control circuit 230. In an example, a composite indication of an eye characteristic, such as an indication of an estimate of TPD, can be calculated, such as by finding the difference between a received indication of IOP and an estimate of an indication of ICP, such as the estimate of an indication of ICP can be a function of a received indication of blood pressure and one or more indications of body parameters, such as BMI and chronological age.

Receiving a target value of an indication of an eye characteristic can include receiving at least one target eye parameter, such as one or more indications of eye characteristics, and one and more indications of body parameters, such as from a user of the apparatus 200, such as from a medical professional prescribing use of the apparatus 200 to a patient, through the UI of the control circuit 230. In an example, a target eye parameter can include a target value for TPD of the eye 100, such as a target value in a range of about 2 mmHg to about 6 mmHg, including TPD target values of about 2 mmHg, about 3 mmHg, about 4 mmHg, about 5 mmHg, and about 6 mmHg. In an example, a target value can include a target value for IOP of the eye 100, such as a target value in a range of about 10 mmHg to about 20 mmHg, including IOP target values of about 10 mmHg, about 11 mmHg, about 12 mmHg, about 13 mmHg, about 14 mmHg, about 15 mm Hg, about 16 mmHg, about 17 mmHg, about 18 mmHg, about 19 mmHg, and about 20 mmHg. In an example, a target value can include one or more indications of body parameters of the patient, such as BMI and patient age.

Receiving a target value of an indication of an eye characteristic can include calculating a composite target value of the indication of the eye characteristic, such as with the CPU of the control circuit 230, based upon received target values, such as one or more indications of an eye characteristic and one or more indications of the body parameters of the patient. In an example, a composite target value of an indication of TPD can be calculated as the weighted sum of an indication of an eye characteristic, such as blood pressure, and one or more indications of body parameters, such as body-mass index (BMI), patient age, and one or more experimental constant values related to one or more indications of eye characteristics including one or more experimental constant values derived from a curve-fitting algorithm.

Receiving a target value of an indication of an eye characteristic can include receiving a target value profile, such as a list of target values corresponding to discrete points in time, for one or more indications of eye characteristics. The magnitude of the received target values can vary with respect to time, such as periodically with time or aperiodically with time. In an example, a received target value profile can include a list of target values for IOP where the magnitude of the IOP target values vary periodically, such as on a diurnal cycle or a cycle that repeats approximately every 24-hour time period.

Determining the difference between the received indication of an eye characteristic and the received target value of the indication of the eye characteristic can include combining the received indication and the received target value with one or more mathematical operations, such as to form an error signal. The error signal can be used as a control signal, such as for the pump 220, to set a gauge pressure, such as a therapeutic pressure level, in the goggle enclosure 210. In an example, the error signal can include a value resulting from subtracting a value of the received target value from a value of the received indication with the CPU of the control circuit 230.

A mathematical operation can include any numerical, symbolic, or logical (e.g., Boolean) operation applied to one or more numbers or one or more arrays of numbers, such as a time-based series of values representing an indication of a eye characteristic. Numerical operations can include addition, subtraction, multiplication, division, weighting, such as by multiplying a number by a constant value to obtain a weighted value, and conversion by a function, such as converting a number to a logarithmic representation of the number.

A device operable to deliver the therapeutic pressure level to the goggle enclosure 210, such as the pump 220, can have one or more operating characteristics, such as power curve for an electric motor where the output power (e.g., a dependent variable) varies as a function motor speed (e.g., an independent variable). A control signal can be generated, such as to incorporate the operating characteristics of the pump 220, to apply a therapeutic pressure level to the goggle enclosure 210, such as by controlling the pump 220 with the control signal.

Selecting a therapeutic pressure level to apply to the goggle enclosure 210 can include generating a control signal related to the therapeutic pressure level, such as by at least one of calculating a control signal or identifying a control signal. Calculating a control signal can include applying one or more mathematical operations to one or more signals, such as received indications of eye characteristics and the error signal. In an example, a control signal can include combining the error signal and a function representing the operating characteristics of the pump 220 with one or more mathematical operations, such as to form a pump control signal.

Identifying a control signal can include comparing the error signal to an array of control signal values, such as to identify a control signal related to the therapeutic pressure level. An array of control signal values can include a lookup table where there exists a functional relationship between an independent variable, such as the error signal, and a dependent variable, such as the control signal.

The functional relationship between and independent and dependent variables can include a linear function of the independent variable to generate the control signal. A linear function can include combinations of mathematical operations applied to at least one of one or more indications of eye characteristics or one or more body parameters, such as where the dependent variable can be directly proportional to the independent variables. In an example, the error signal can be multiplied by a system gain, such as a gain proportional to an indication of a eye characteristic, to realize a pump control signal that can operate the pump 220 to deliver the therapeutic pressure level required to treat the eye condition of the eye 100.

The functional relationship between and independent and dependent variables can include a nonlinear function of the independent variable to generate the control signal. A nonlinear function can include combinations of mathematical operations applied to at least one of one or more indications of eye characteristics or one or more body parameters, such as where the dependent variable can be indirectly proportional to the independent variables. A nonlinear function can include combinations of mathematical operations applied to one or more indications of parameters exclusive from the patient, such as the operating characteristics of a device including a frequency domain and time domain characterizations of device operation. In an example, the error signal can be weighted by a nonlinear function or parameter, such as a function or parameter describing the operating characteristics of the pump 220 where the gauge pressure generated by the pump 220 can be dependent on the speed of the pump 220, to realize a control signal that can operate the pump 220 to deliver the therapeutic pressure level required to treat the eye condition of the eye 100.

Transmitting an indication of the therapeutic pressure level can include communicating the control signal through an output channel of the control circuit 230, such as a first output of the control circuit 230, to a device, such as a device operable to deliver the therapeutic pressure level to the goggle enclosure 210. In an example, the first output of the control circuit 230 can be electrically connected to the pump 220, such that the pump 220 can receive the pump control signal to set, or otherwise generate and control, the gauge pressure delivered to the goggle enclosure 210. In an example, the first output of the control circuit 230 can be electrically connected to one or more valve assemblies, such as motorized valve assemblies including controllable vents and motorized venturi valve assemblies, the valve assemblies including one or more pressurized fluid sources, such as a fluid source containing a positive or negative gauge pressure connected to the goggle enclosure 210 through the valve assemblies.

Setting a therapeutic pressure in the goggle enclosure 210 can include applying a therapeutic pressure to the goggle enclosure 210 to treat an eye condition, such as an abnormal eye condition. Therapeutic pressure can be generated with a pressure source, such as the pump 220, and applied to the cavity 212 of the goggle enclosure 210, such as by creating a gauge pressure in the goggle enclosure 210, to treat an eye condition of the eye 100. The applied therapeutic pressure can include a gauge pressure, such as a positive or negative gauge pressure applied to the goggle enclosure 210. The gauge pressure can be generated on demand, such as with the pump 220, or supplied by one or more pressurized fluid sources, such as a pressurized cylinder of gas, including a control valve, such as a pressure regulator, to meter gauge pressure applied to the goggle enclosure 210.

Setting a therapeutic pressure in the goggle enclosure 210 can include establishing the duration of therapeutic pressure to apply to the cavity 212 to treat the eye condition of the eye 100. The duration of therapeutic pressure applied can depend on the eye condition treated with the therapeutic pressure. In an example, establishing the duration of therapeutic pressure applied can include identifying the eye condition of the eye 100 requiring treatment and prescribing the duration of therapeutic pressure to apply to the cavity 212. Prescribing a duration of therapeutic pressure can include specifying a length of time to apply the therapeutic pressure to the cavity 212.

Further monitoring of the received data to control the pump can include adjusting the therapeutic pressure, such as in the goggle enclosure 210. Adjusting the therapeutic pressure can include improving the effect of the applied therapeutic pressure can include varying the therapeutic pressure level applied to the goggle enclosure 210 to minimize the difference between the received indications of one or more feedback signals and a received target value of the physiological parameter. Adjusting the therapeutic pressure for application to the eye 100 can include the use of feedback control principles, such as closed-loop control principles implemented with algorithms running on the CPU of the control circuit 224, to adjust the therapeutic pressure level applied to the goggle enclosure 210.

Adjusting the therapeutic pressure in the goggle enclosure 210 can include detecting one or more feedback signals, such as from a patient wearing the apparatus 200. The one or more feedback signals can include information regarding a pressure indication including an indication of a physiological parameter and an indication of the therapeutic pressure level applied to the goggle enclosure 210, such as detected with one or more sensing instruments 513. The apparatus 200 can receive information regarding the one or more feedback signals with the control circuit 224, such as by receiving one or more feedback signals with one or more input channels on the control circuit 224.

Adjusting the therapeutic pressure level in the goggle enclosure 210 can include processing one or more feedback signals. Processing a feedback signal can include calculating a composite indication of a physiological parameter, such as where the composite indication can be a function of one or more feedback signals.

Adjusting the therapeutic pressure level in the goggle enclosure 210 can include receiving updated target values for the feedback signals, such as updated target values for one or more indications of a physiological parameter and one or more indications of the body parameters of the patient. Updated target values can be received from a user of the apparatus 200, such as through the UI of the control circuit 224. Receiving updated target values can further include calculating updated composite target values for the feedback signals, such as with the CPU of the control circuit 224, based upon received updated target values.

Adjusting the therapeutic pressure level in the goggle enclosure 210 can include determining the difference between the feedback signals and the received target values for the feedback signals, such as to form an updated error signal.

Adjusting the therapeutic pressure level can include selecting an updated therapeutic pressure level based on the updated error signal, and transmitting an updated control signal, such as an updated pump control signal, to a device operable to deliver the updated therapeutic pressure to the goggle enclosure 210, such as the pump 220.

Adjusting the fluid pressure, such as the fluid pressure level 503, can include generating a pump signal 501, such as in response to a detected eye parameter signal 502. A detected eye parameter signal can be detected, such as by performing a visualization, such as of the central retinal vein 133 displaying a SVP, and analyzing the visualization, such as analyzing first and subsequent visualizations, such as of the SVP, to determine a change in at least one eye or other physiologic characteristic between the first and subsequent visualizations, such as a change in caliber of the SVP. Visualization can be performed with a VAD 509, such as an OCT system 509D. Based on the detected eye parameter signal 502, such as the change in caliber of the SVP, the control circuit can generate a pump signal 501, such as an adjusted pump signal that can be at least one of in-phase or out-of-phase with the detected eye parameter signal 502. In an example, the pump signal 501, such as an in-phase pump signal 501, can generate a fluid pressure level 503, such as an in-phase fluid pressure level 503 that can be applied to the goggle enclosure 210, such as to minimize the dynamic component of TMP. In an example, the pump signal 501, such as an out-of-phase pump signal 501, can generate a fluid pressure level 503, such as an out-of-phase fluid pressure level 503 that can be applied to the goggle enclosure 210, such as to maximize the dynamic component of TMP.

Controlling the pump 220 can include processing the received data, such as with the control circuit 230. The received data can include the composite signal 513, such as can include at least one of the detected eye parameter signal 510, the target eye parameter signal 512, or the enclosure sensor signal 507.

Figure 10:
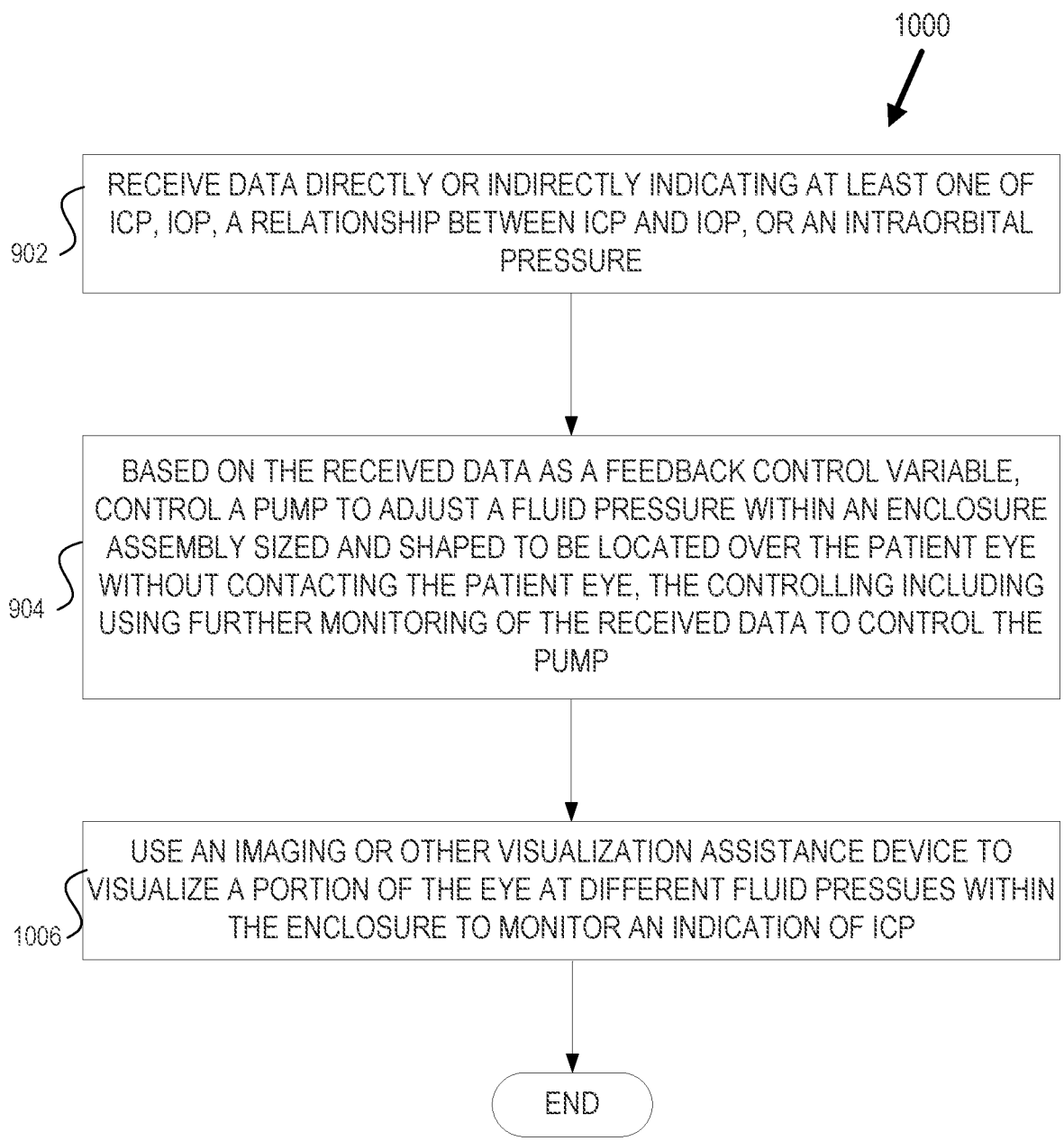
FIG. 10 shows an example of a method for using the apparatus to apply a pressure to an eye to monitor ICP.

Controlling the pump 220 can include transmitting an indication of the processed composite data 501 to the pump 220. Indications of the processed composite data 501 can be transmitted by at least one of an electrical connection, such with a wired connection between the control circuit 230 and the pump 220, or a wireless connection. The pump 220 can receive the indication of the processed data 201, such as by at least one of an electrical interface, such as with a wired interface between the control circuit 230 and the pump 220, or a wireless interface, FIG. 10 shows an example of a method 1000 for using the apparatus 200 to apply a pressure to an eye 100 to monitor ICP. At 1006, an imaging device or other visualization assistance device 509 can visualize a portion of the eye 100, such as at different fluid pressures within the goggle enclosure 210, such as to monitor an indication of ICP.

Figure 11:
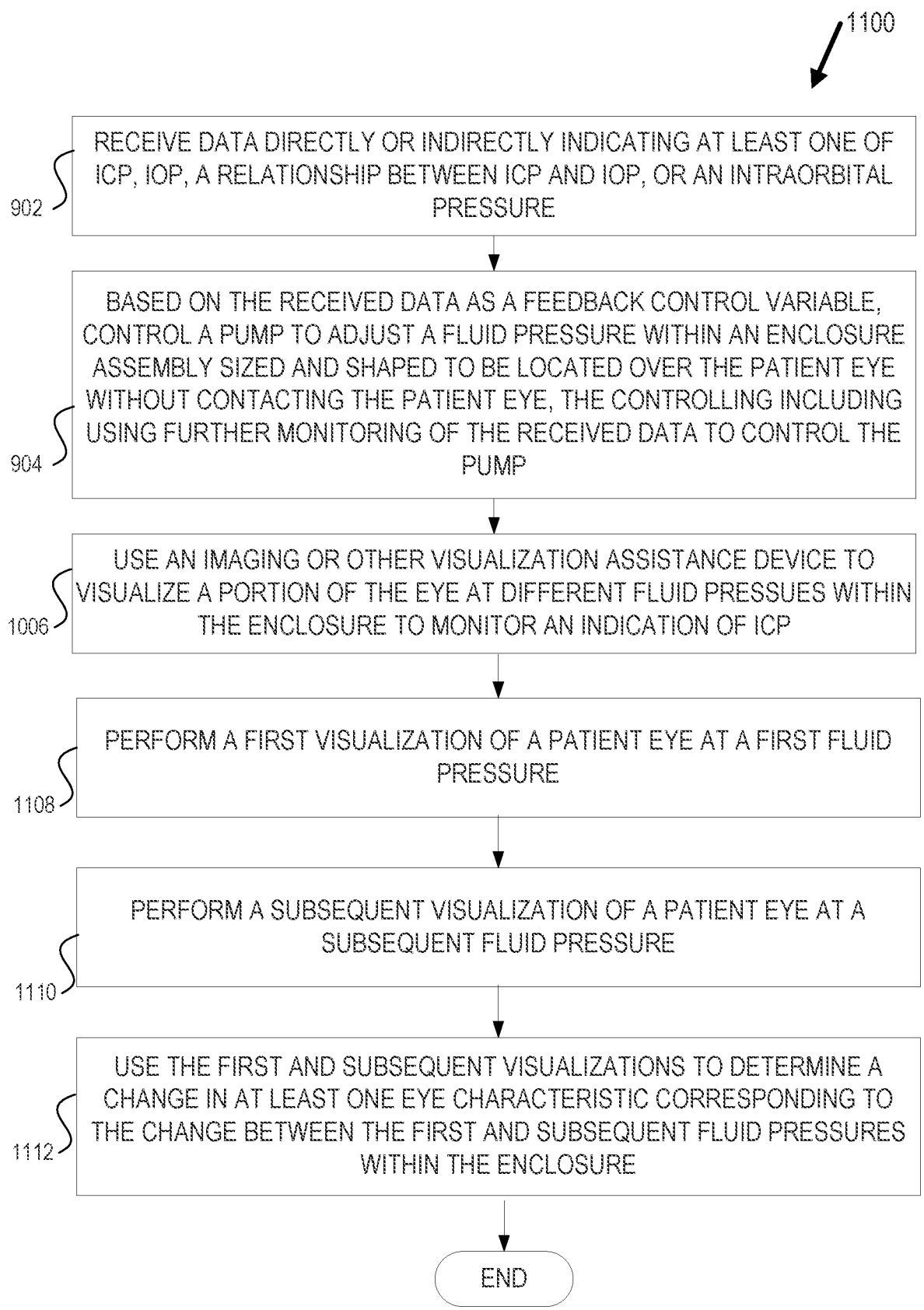
FIG. 11 shows an example of a method for using the apparatus to apply a pressure to an eye, such as for determining ICP or monitoring ICP.

FIG. 11 shows an example of a method 1100 for using the apparatus 200 to apply a pressure to an eye 100, such as for determining ICP or monitoring ICP. At 1208, a first visualization of a patient eye 100 at a first fluid pressure can be performed, such as with a goggle enclosure 210 sized and shaped to be located over the patient eye 100 without contacting the patient eye 100.

At 1110, a subsequent visualization of the patient eye 100 at a subsequent fluid pressure can be performed, such as the subsequent fluid pressure can be different from the first fluid pressure. A subsequent visualization can include a visualization, such as a visualization performed after the first visualization, such as a second, third, fourth, fifth, or other visualization.

At 1112, the first and subsequent visualizations can be used to determine a change, such as in at least one eye characteristic, such as corresponding to the change between the first and second fluid pressures within the enclosure. The eye characteristic can include a change in the caliber of a blood vessel, such as a blood vessel of the eye, such as at least one of a blood vessel in the intraocular space including a venous blood vessel, or a blood vessel on the patient eye 100, such as an episcleral venous vessel. The eye characteristic can include a state of a blood vessel, such as a collapsed state of an intraocular venous blood vessel, such as due to a fluid pressure applied to the cavity 212 of the goggle enclosure 210. In an example, an eye characteristic change criterion can include the collapse of an intraocular venous blood vessel, such as due to a fluid pressure applied to the cavity 212 of the goggle enclosure 210.

Performing a visualization can include selecting a VAD 509, such as a VAD 509 to achieve the objectives of examination for the patient eye 100. Performing a visualization can include selecting one or more detector devices 508, such as to be used in combination with a VAD 509, to achieve at least one of determining or monitoring an eye characteristic.

Determining a change in at least one eye characteristic can include processing a visualization, such as with a processing technique. A processing technique can include manually processing at least one visualization, such as by observing a visualization, such as with the eye of an observer.

Observing a visualization can include perceiving an undocumented image of a patient eye 100, such as an observer observing a patient eye 100, and assessing the eye 100, such as by drawing a conclusion based upon observation of the undocumented image. In an example, processing a visualization can include an observer, such as an ophthalmologist, observing a patient eye 100, such as with an ophthalmoscope, to visualize an eye characteristic, such as the cup-to-disc ratio of the optic nerve 118, to determine an indication of the presence of a possible abnormality in the patient eye 100, such as a cup-to-disc ratio that can be different from a ratio of 0.3.

Observing a visualization can include perceiving one or more undocumented images of a patient eye 100, such as to detect a change in an eye characteristic between at least one of a first or subsequent undocumented images. In an example, processing a visualization can include locating an apparatus 200 on a patient eye 100, applying a first fluid pressure to a cavity 212 of the goggle enclosure 210, visualizing an eye characteristic of the patient eye 100, such as a cup-to-disc ratio due to the first fluid pressure, applying a second fluid pressure to the cavity 212, such as a second fluid pressure different from the first fluid pressure, visualizing the eye characteristic, such as the cup-to-disc ratio due to the second fluid pressure, and detecting a change in the cup-to-disc ratio due to the first and second fluid pressures, such as by detecting a change between the first and second images, such as first and second undocumented images.

A processing technique can include digitally processing at least one visualization, such as by observing a visualization with a VAD 509, such as a VAD 509 with the capability to store a digital image.

Observing a visualization can include perceiving a documented image of a patient eye 100, such as with a VAD 509 with the capability to store a digital image, and assessing the eye 100, such as by drawing a conclusion based upon observation of the documented image. In an example, processing a visualization can include an observer, such as an ophthalmologist observing the documented image of a patient eye 100, such as the cup-to-disc ratio of the optic nerve 118, to determine an indication of the presence of a possible abnormality in the patient eye 100, such as a cup-to-disc ratio that can be different from a ratio of 0.3.

Observing a visualization can include perceiving one or more documented images of a patient eye 100, such as to detect a change in an eye characteristic between at least one of a first or subsequent documented images. In an example, processing a visualization can include locating an apparatus 200 on a patient eye 100, applying a first fluid pressure to a cavity 212 of the goggle enclosure 210, visualizing an eye characteristic of the patient eye 100, such as a cup-to-disc ratio due to the first fluid pressure with a first image, applying a second fluid pressure to the cavity 212, such as a second fluid pressure different from the first fluid pressure, visualizing the eye characteristic, such as the cup-to-disc ratio due to the second fluid pressure with a second image, and detecting a change in the cup-to-disc ratio due to the first and second fluid pressures, such as by observing a change between the first and second images, such as first and second digital images.

Analyzing can include observing a change, such as between first and second digital images. Observing a change can include manually processing the first and second digital images, such as to determine a change in an indication of an eye characteristic. Manually processing can include detecting a change between a first and second digital image, such as a change between at least one of pixel or voxel characteristics in corresponding digital elements with an eye of an observer. Detecting a change can include the eye of an observer perceiving the first digital image, perceiving the second digital image, and determining differences between the first and second digital images.

Observing a change between first and second digital images can include digitally processing the first and second digital images, such as to determine a change in an indication of an eye characteristic. Digitally processing a first and second image can include detecting a change between a first and second digital image, such as a change between at least one of pixel or voxel characteristics in corresponding digital elements with a computing device. Detecting a change can include placing representations of the first and second digital images into the memory of a computing device, such as random access memory or RANI, and running an algorithm, such as a digital comparator algorithm, to determine differences between the first and second digital images. Running an algorithm can include initiating a software code, such as a software code implemented on a computing device, and applying a set of instructions in the software code to the representations of the first and second digital images.

Figure 12:
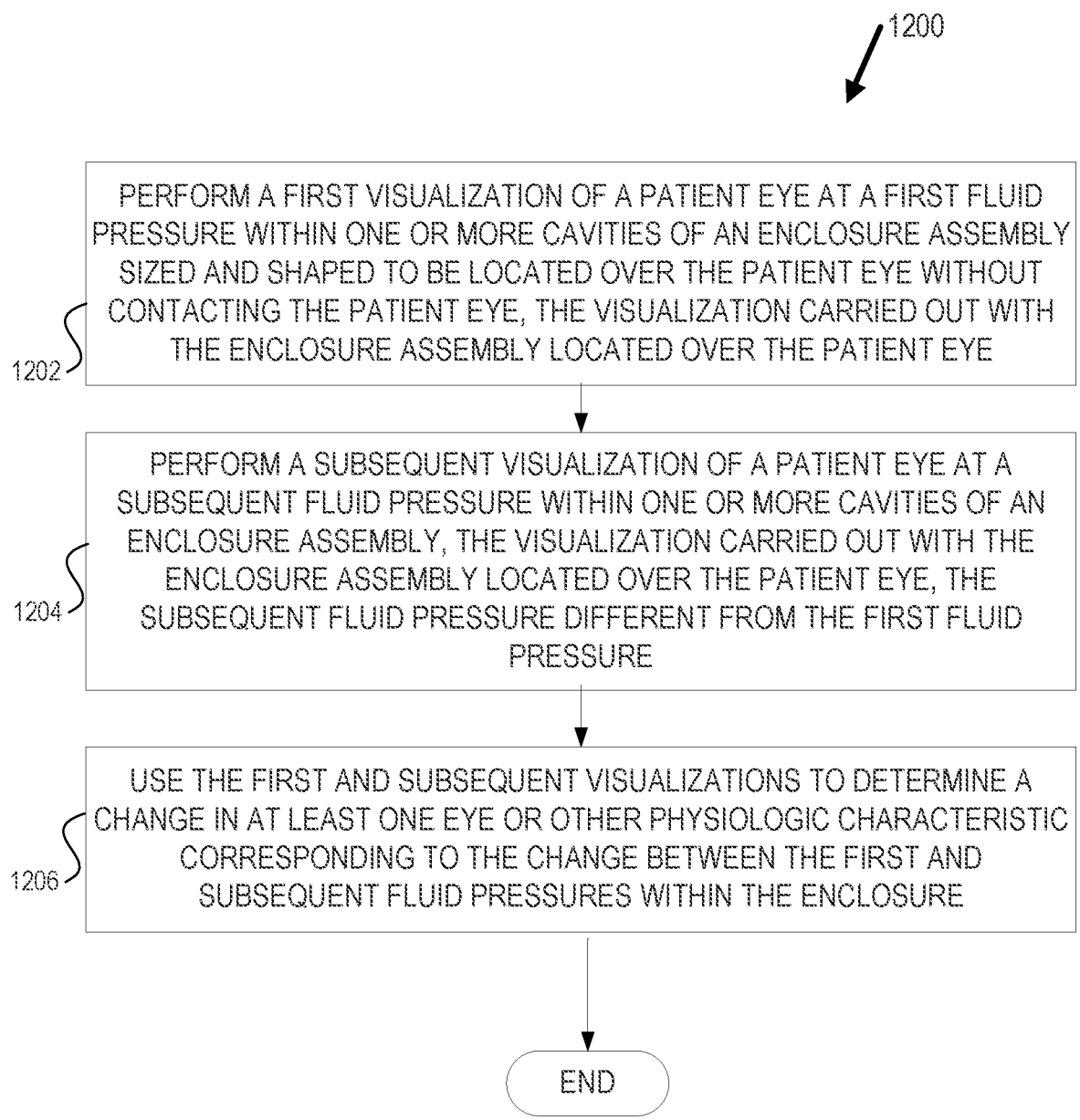
FIG. 12 shows an example of a method for using the apparatus, such as for determining an indication of ICP.

FIG. 12 shows an example of a method 1200 for using the apparatus 200, such as for determining an indication of ICP. At 1202, a first visualization of a patient eye 100 at a first fluid pressure within one or more cavities 212 of an goggle enclosure 210 sized and shaped to be located over the patient eye 100 without contacting the patient eye 10 can be performed, the visualization carried out with the goggle enclosure 210 located over the patient eye 100.

At 1204, a subsequent visualization of a patient eye 100 at a subsequent fluid pressure within one or more cavities 212 of a goggle enclosure 210, the visualization carried out with the goggle enclosure 210 located over the patient eye 100, the subsequent fluid pressure different from the first fluid pressure.

At 1206, the first and subsequent visualizations can be used to determine a change in at least one eye or other physiological characteristic corresponding to the change between the first and subsequent fluid pressures within the enclosure.

Figure 13:
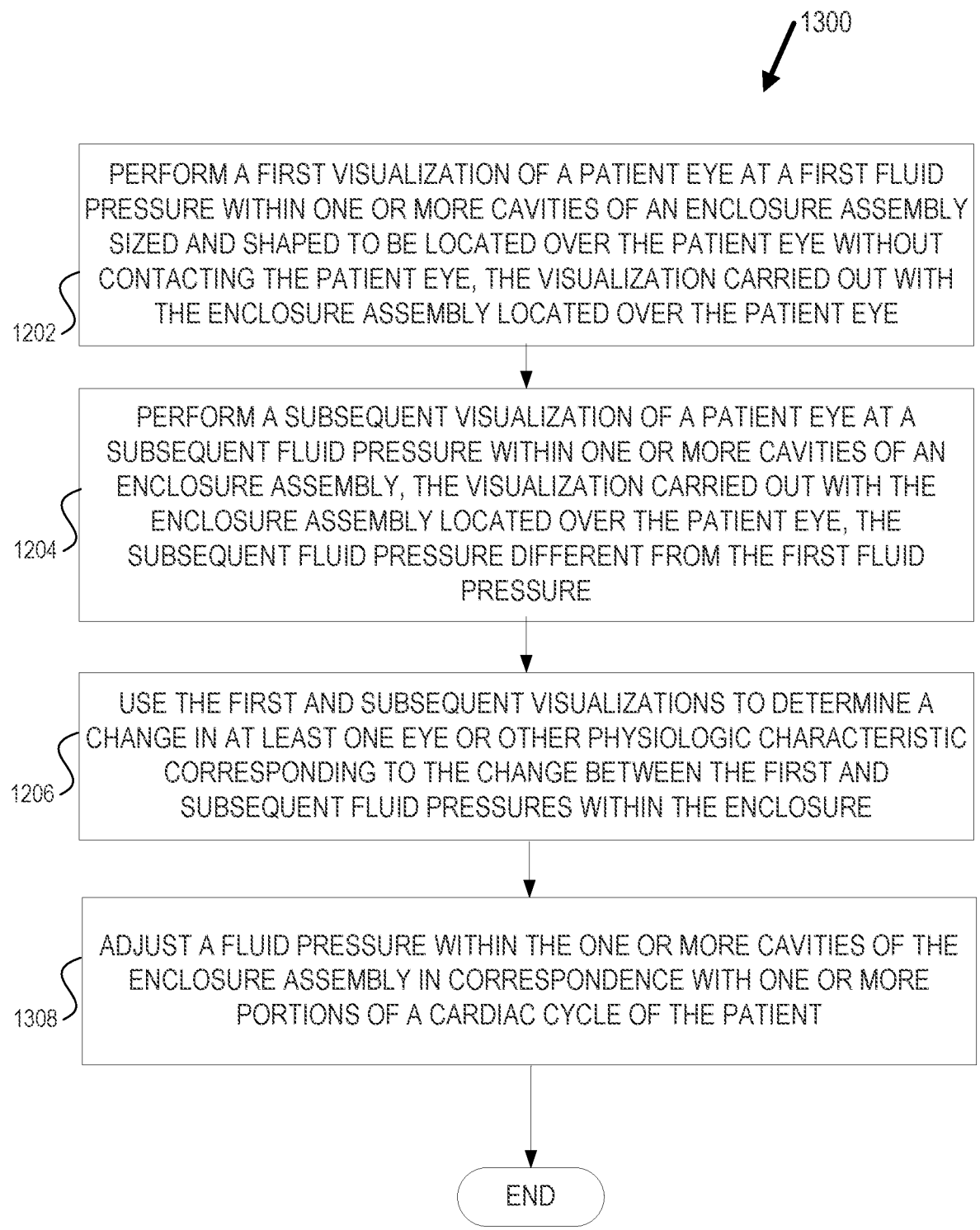
FIG. 13 shows an example of a method for using the apparatus for synchronizing pressure applied to the goggle enclosure with the patient cardiac cycle.

FIG. 13 shows an example of a method 1300 for using the apparatus 200 for synchronizing pressure applied to the goggle enclosure 210 with the patient cardiac cycle. At 1308, a fluid pressure within the one or more cavities of the goggle enclosure 210 can be adjusted in correspondence with one or more portions of a cardiac cycle of the patient.

Figure 14:
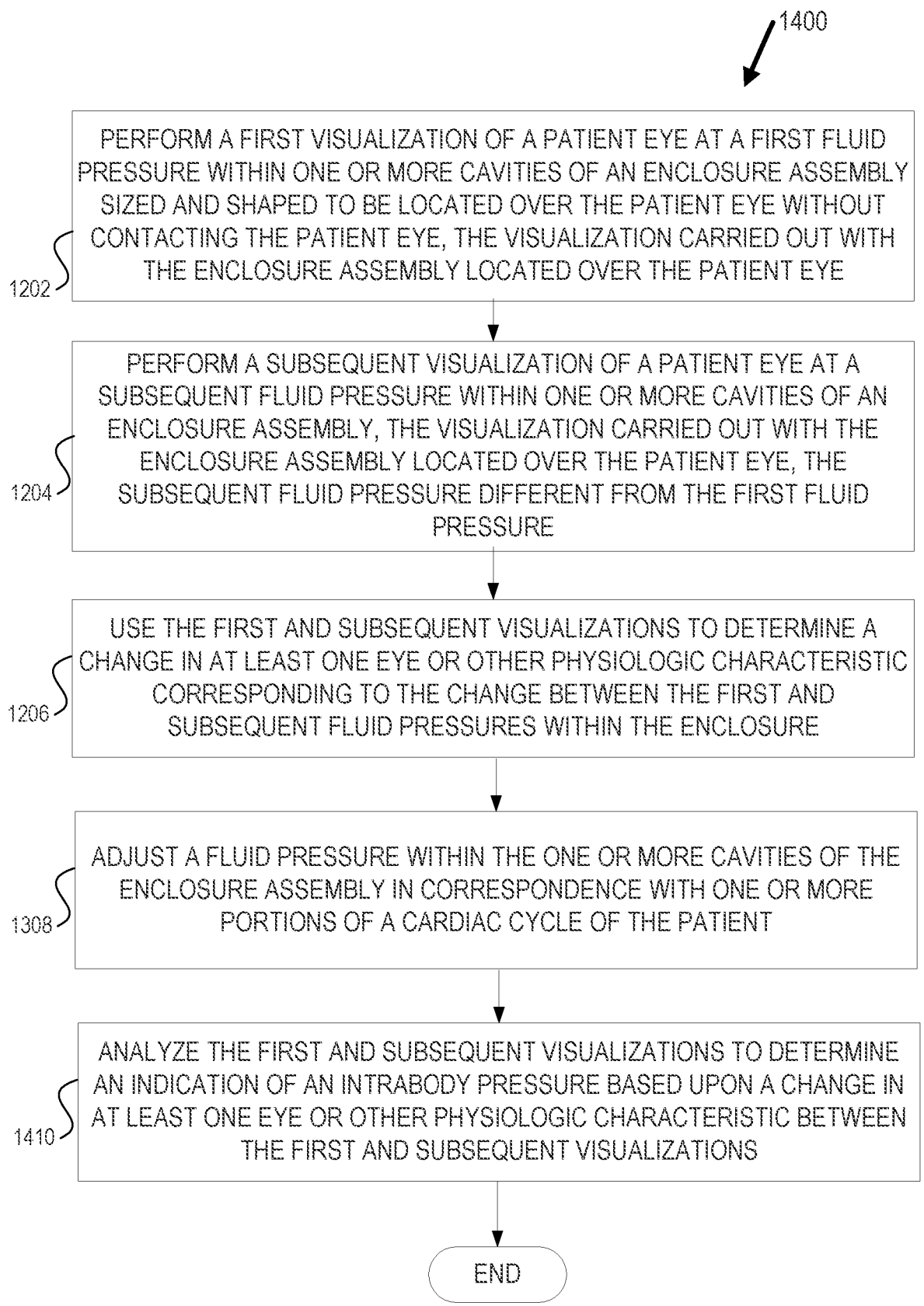
FIG. 14 shows an example of a method for using the apparatus for determining ICP based upon an indication of the patient cardiac cycle.

FIG. 14 shows an example of a method 1400 for using the apparatus 200 for determining ICP based upon an indication of the patient cardiac cycle. At 1410, the first and subsequent visualizations can be analyzed to determine an indication of an intrabody pressure based upon a change in at least one eye or other physiological characteristic between the first and subsequent visualizations.

Figure 15:
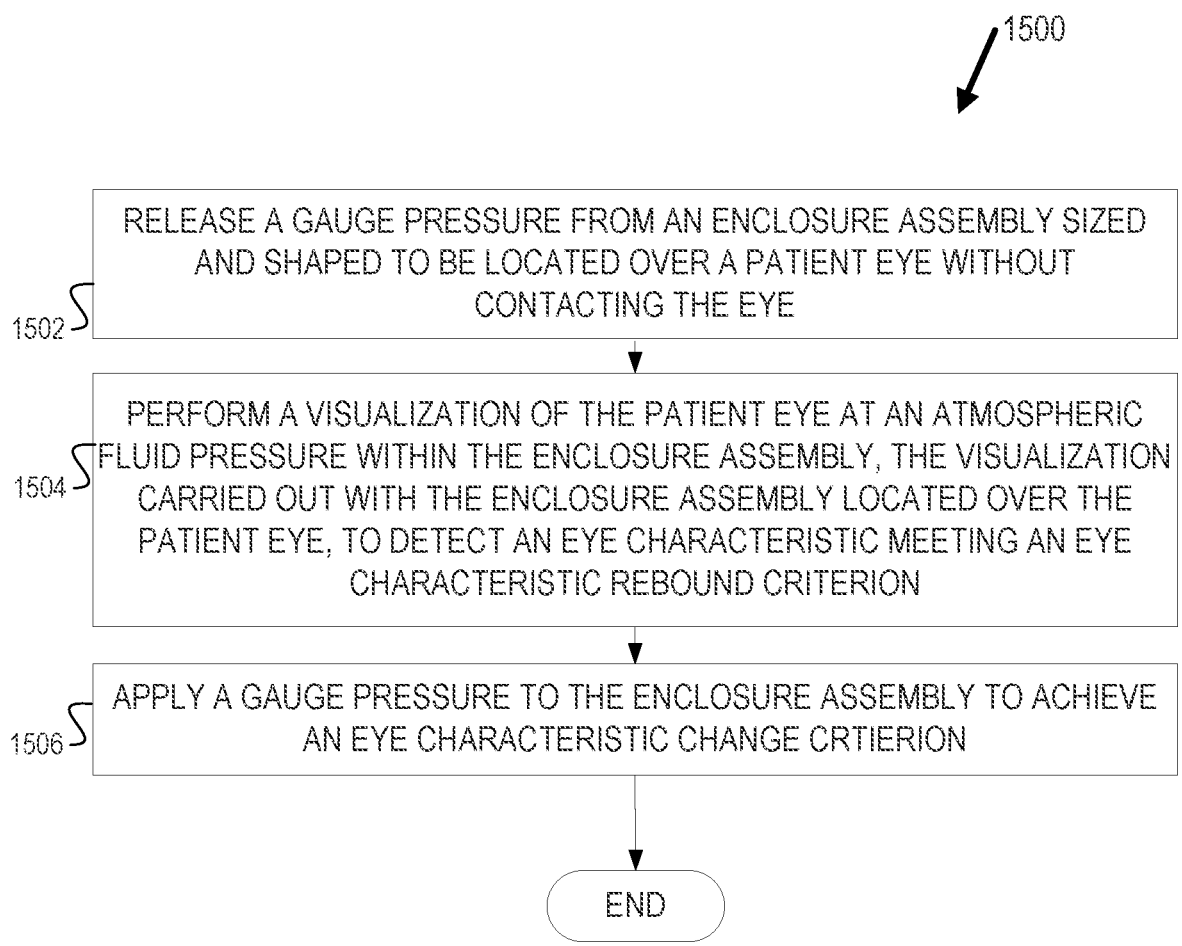
FIG. 15 shows an example of a method, such as for conducting a diagnostic examination of the eye after concluding a therapeutic session using the apparatus.

FIG. 15 shows an example of a method 1500, such as for conducting a diagnostic examination of the eye 100 after concluding a therapeutic session using the apparatus 200. The method 1500 can include an example of a method for using the apparatus 200, such as by combining a diagnostic method and a therapeutic method, such as for monitoring and treating at least one of an acute or a chronic abnormal eye condition.

At 1502, a gauge pressure can be released from a goggle enclosure 210 sized and shaped to be located over a patient eye 100 without contacting the eye.

At 1504, a visualization of the patient eye 100 can be performed at an atmospheric fluid pressure within the goggle enclosure 210, the visualization carried out with the goggle enclosure 210 located over the patient eye 100, to detect an eye characteristic meeting an eye characteristic rebound criterion. In an example, an eye characteristic rebound criterion can include the recovery of the central retinal vein 133 to an ambient cross-sectional shape, such as a generally circular shape.

At 1506, a gauge pressure can be applied to the goggle enclosure 210, such as to achieve an eye characteristic change criterion. In an example, an eye characteristic change criterion can include the collapse of an intraocular venous blood vessel, such as due to a fluid pressure applied to the cavity 212 of the goggle enclosure 210.

Applying a gauge pressure to the patient eye 100, such as a positive or negative gauge pressure, can cause the patient eye 100 to deform, such as at least one of compressing due to a positive gauge pressure or expanding due to a negative gauge pressure, to assume a deformed state. Short term deformation of the patient eye 100, such as deformation induced during a diagnostic examination using the apparatus 200, can cause a change in the eye characteristics of the patient eye 100, such as a temporary change in the eye characteristics of the patient eye 100 as referenced from baseline eye characteristics. Baseline eye characteristics, such as a first set of baseline eye characteristics, can include eye characteristics detected from a patient eye 100 in a relaxed state, such as in the absence of a gauge pressure applied to the patient eye 100 including eye characteristics detected at an ambient or atmospheric pressure.

Long term deformation of the patient eye 100, such as deformation induced during therapeutic use of the apparatus 200 on the patient eye 100, can cause the patient eye 100 to remodel or otherwise adapt to the applied fluid pressure, such as to induce a permanent change in the eye characteristics, such as to permanently shift the first set of baseline eye characteristics of the patient eye 100. In other words, remodeling of a patient eye 100, such as due to long term deformation of the patient eye 100 with the use of the apparatus 200, can cause the patient eye 100 to assume a second set of baseline eye characteristics, the second set of baseline eye characteristics different from the first set of baseline eye characteristics.

Assessment of the patient eye 100, such as an assessment to determine the effectiveness of a therapeutic regimen, can benefit from conducting diagnostic tests on a patient eye 100 in a relaxed state. The time for a patient eye 100 to transition from a deformed state to relaxed state can vary, such as due to patient physiology. Releasing the gauge pressure, such as from the goggle enclosure 210, can include exposing the patient eye 100 to an ambient pressure, such as to allow the patient eye 100 to recover from a deformed state to a relaxed state. An ambient pressure can include at least one of an atmospheric pressure or a fluid pressure not influenced by the pump 220. Gauge pressure can be released through the controllable vent, such as by opening the controllable vent, such as by providing a low resistance fluid path to equalize the differential fluid pressure between the goggle enclosure 210 and the surrounding atmosphere. Gauge pressure can be released by turning off the pump 220, such as allow gauge pressure in the goggle enclosure 210 to bleed off, such as by providing a variable resistance fluid path to equalize the differential fluid pressure between the goggle enclosure 210 and the surrounding atmosphere.

Detecting an eye characteristic meeting an eye characteristic rebound criterion can include visualizing a portion of the patient eye 100, such as a portion of the patient eye 100 including an indication of an eye characteristic, observing the visualization, such as to compare the eye characteristic to an eye characteristic rebound criterion. In an example, an eye characteristic, such as the caliber of a central retinal vein 133 deformed due to a gauge pressure in an goggle enclosure 210 of an apparatus 200, can be visualized, such as with an OCT system 509D, such as during release of gauge pressure from the goggle enclosure 210, and compared to an eye characteristic rebound criterion, such as the relaxed caliber of the central retinal vein 133.

Releasing the gauge pressure can include visualizing the eye 100, such as after an eye characteristic rebound criterion of the eye 100 has been achieved. In an example, the patient eye 100 can be visualized, such as to detect an indication of an eye characteristic, such as with the patient eye 100 in a relaxed state.

The relaxed caliber of a central retinal vein 133 can be determined, such as by at least one of measuring the caliber of the central retinal vein 133 in a relaxed state, such as in the patient eye 100 under atmospheric conditions, or by calculating an estimate of the caliber of the central retinal vein 133. Calculating an estimate of the caliber of the central retinal vein 133 can include performing a visualization of the central retinal vein 133 subjected to a gauge pressure applied with the apparatus 200, such as at a gauge pressure sufficient to cause the central retinal vein 133 to collapse, detecting the caliber of the central retinal vein 133, such as in a deformed state, such as at collapse of the central retinal vein 133, and calculating an estimate of the caliber of the relaxed central retinal vein 133. Calculating an estimate of the caliber of the relaxed central retinal vein 133 can include dividing the detected caliber of the central retinal vein 133, such as in a collapsed state, by the mathematical constant known as pi ($\pi$), such as to calculate an estimate of the radius of the undeformed central retinal vein 133, and multiplying the estimate of the radius by 2 resulting in an estimate of the caliber of the undeformed central retinal vein 133.

Setting a therapeutic pressure can include identifying an eye condition of the eye 100, such as an abnormal eye condition, such as for purposes of prescribing a treatment regimen of therapeutic pressure for the eye condition. The presence of an abnormal eye condition can be identified through evaluation of one or more indications of an eye characteristic, such as the TPD of the eye 100. An indication of TPD can include the cup-to-disc ratio of the optic disc 150. An eye 100 with a cup-to-disc ratio of about 0.3 can indicate a "normal" TPD for the eye 100, such as an eye 100 with physiologically normal function. An eye 100 with a cup-to-disc ratio less than or greater than about 0.3 can indicate an "abnormal" TPD, such as an eye 100 without physiologically normal function, such as an eye 100 requiring treatment.

A value of the cup-to-disc ratio greater than about 0.3 can indicate the presence of an abnormal eye condition, such as glaucoma. For example, cup-to-disc ratios in the range of about 0.35 to about 0.9, such as cup-to-disc ratios of about 0.35, about 0.4, about 0.5, about 0.6, about 0.7, about 0.8, and about 0.9, can indicate the presence of an abnormal eye condition including glaucoma. A value of the cup-to-disc ratio less than about 0.3 can indicate the presence of an abnormal eye condition, such as optic disc edema. For example, a cup-to-disc ratio of about 0.25, about 0.2, about 0.15, about 0.1, about 0.05, and the absence of a discernible cup in the optic disc 150, such as indicated with a cup-to-disc ratio of about 0.00, can indicate the presence of an abnormal eye condition including optic disc edema and papilledema.

Figure 16:
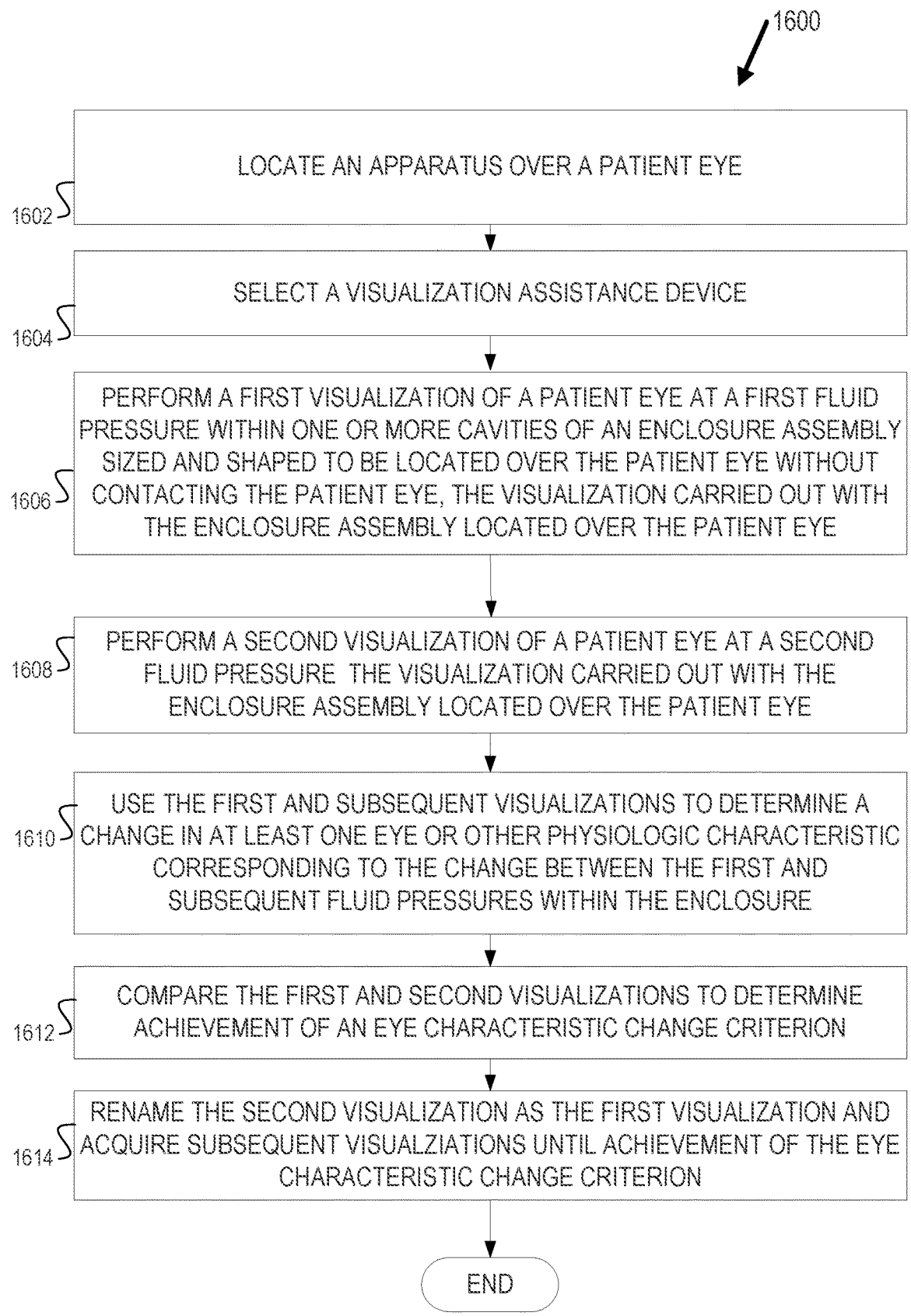
FIG. 16 shows an example of a method for determining at least one of ICP or IOP using the apparatus, such as for diagnostic purposes.

FIG. 16 shows an example of a method 1600 for determining at least one of ICP or IOP using the apparatus 200, such as for diagnostic purposes. At 1602, the apparatus 200 can be located on a patient, such as a patient suspected of suffering from an abnormal eye condition.

At 1604, a visualization assistance device 509 can be selected, such as to visualize at least a portion of the patient eye 100. Selection of the VAD 509 can be based on whether IOP, ICP or both are to be measured.

At 1606, a visualization can be performed on the patient eye 100, such as a first visualization at a first fluid pressure. The apparatus 200 can record metadata, including applied pressure, etc. The first image can include a baseline image, such as an image to which other images can be compared to detect a change in an eye characteristic.

At 1608, a visualization, such as a second visualization at a second fluid pressure, can be performed. The second fluid pressure can be different from the first fluid pressure.

At 1610, first and second visualizations can be used to determine a change in at least one eye or other physiological characteristic corresponding to the change between the first and second fluid pressures within the enclosure.

At 1612, the change in an eye characteristic can be compared to at least one change criterion, such as to determine if the change criterion has been achieved.

At 1614, the second visualization can be renamed as the first visualization, and a subsequent visualization acquired, such as until the eye characteristic change criterion can be achieved.

Figure 17:
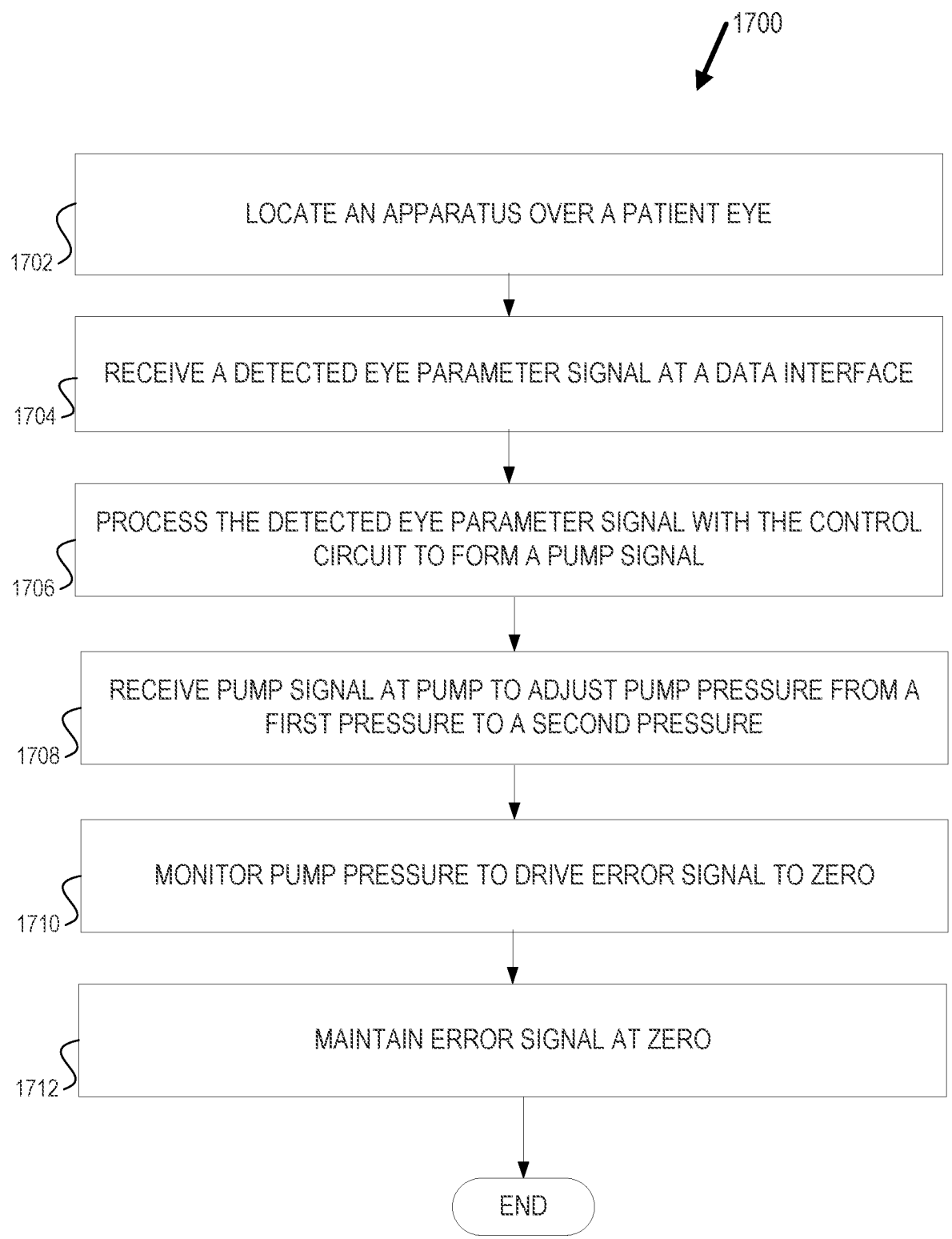
FIG. 17 shows an example of a method for using the apparatus, such as for therapeutic purposes including treating at least one of an acute or a chronic abnormal eye condition.

FIG. 17 shows an example of a method 1700 for using the apparatus 200, such as for therapeutic purposes including treating at least one of an acute or a chronic abnormal eye condition.

At 1702, the apparatus 200 can be located on a patient, such as a patient diagnosed with an abnormal eye condition.

At 1704, a detected eye parameter signal 510 can be received at the data interface 232.

At 1706, the detected eye parameter signal 510 can be processed by the control circuit 230, such as to form a pump control signal 501. Processing can include comparing an indication of the first fluid pressure to a setpoint, such as to cacluate an error signal. The pump control signal 501 can include a pump signal, such as a pump signal that reduces the error signal at a predetermined rate.

At 1708, the pump control signal 501 can be received by the pump 220, such as to adjust the fluid pressure delivered to the goggle enclosure 210 from a first pressure to a second pressure, the second pressure different from the first pressure.

At 1710, the fluid pressure in the goggle enclosure 210 can be monitored, such as to drive and error signal to zero.

At 1712, the error signal can be maintained at zero, such as for a clinically relevant period of time.

Figure 18:
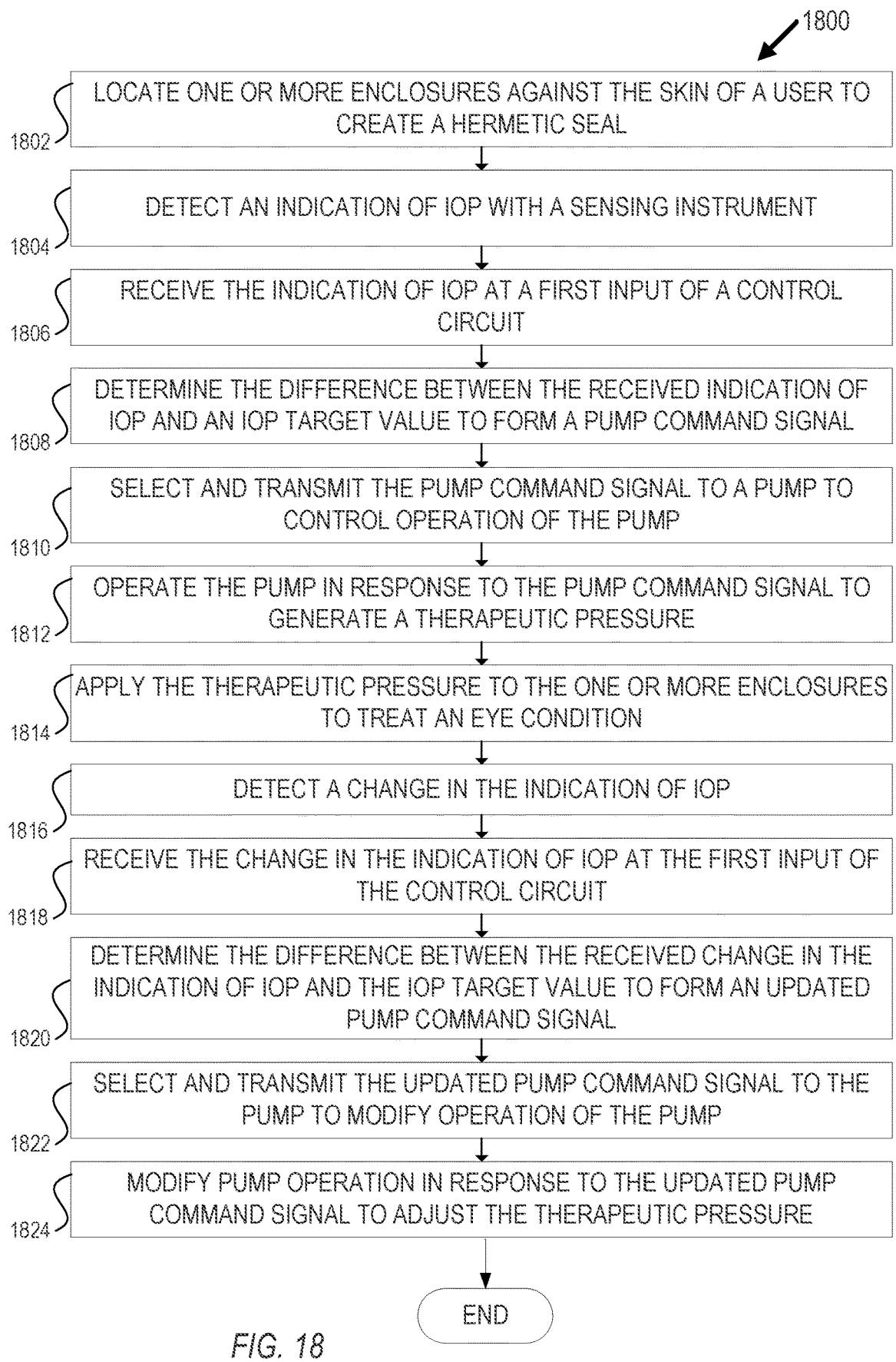
FIG. 18 illustrates an example method of setting and adjusting a therapeutic pressure using IOP for application to an eye, such as for treatment of an abnormal eye condition.

FIG. 18 illustrates an example method 1800 of setting and adjusting a therapeutic pressure using IOP for application to an eye 100, such as for treatment of an abnormal eye condition. At 1802, an apparatus 200 can be worn by a patient, such as locating a goggle enclosure 210 over an eye 100 of a patient, so that the goggle enclosure 210 contacts the skin of the patient, such as to form a hermetic seal between the goggle enclosure 210 and the skin of the patient.

At 1804, information regarding a pressure indication, such as an indication of a physiological parameter including IOP, can be detected, such as with a sensing instrument 513 including an internal sensing instrument 513*b*.

At 1806, the indication of IOP, can be received by the control circuit 224, such as at a first input channel of the control circuit 224.

At 1808, the difference between the received indication of IOP and an IOP target value, such as an IOP target value received through the UI attached to the control circuit 224, can be determined, such as by a CPU attached to the control circuit 224. The difference between the received indication of IOP and an IOP target value can be a signal, such as an error signal.

At 1810, the pump command signal can be selected, such as based on the error signal, and transmitted from the CPU through one or more output channels of the control circuit 224 to another device, such as a pump 220, to control operation of the device.

At 1812, the pump 220 can respond to receiving the pump command signal from one or more output channels of the control circuit 224, such as by operating the pump to generate a therapeutic pressure to apply to the goggle enclosure 210 of the apparatus 200.

At 1814, the therapeutic pressure can be applied to the goggle enclosure 210 to create a therapeutic pressure level in the cavity 212, such as to treat an eye condition.

At 1816, a sensing instrument 513, such as an internal sensing instrument 513*b*, can detect a change in an indication of a physiological parameter, such as IOP, in response to applying the therapeutic pressure. The change in IOP can be a feedback signal, such as an IOP feedback signal.

At 1818, the IOP feedback signal, can be received by the control circuit 224, such as at a first input channel of the control circuit 224.

At 1820, the difference between the IOP feedback signal and an IOP target value, such as an updated IOP target value, can be determined, such as with the CPU attached to the control circuit 224. The difference between the IOP feedback signal and an updated IOP target value can be a signal, such as an updated error signal.

At 1822, the updated pump command signal can be selected, such as based on the updated error signal, and transmitted from the CPU through one or more output channels of the control circuit 224 to another device, such as the pump 220, to modify operation of the device.

At 1824, the pump 220 can respond to receiving the updated pump command signal, such as by operating the pump to generate an updated therapeutic pressure to apply to the goggle enclosure 210 of the apparatus 200.

Various Notes

To further illustrate the apparatus and methods of the present disclosure, a non-limiting list of Examples is provided here:

Example 1 can include or use subject matter, such as an apparatus for at least one of diagnosing or treating an eye condition. The subject matter can comprise a goggle enclosure, sized and shaped to be seated on an eye socket of an eye to provide one or more cavities within the enclosure that extend about an entire exposed anterior portion of the eye, a pump, in fluidic communication with the one or more cavities to apply a fluid pressure to the one or more cavities, the pump configured to adjust a fluid pressure within the one or more cavities of the goggle enclosure, and a control circuit, including a data interface to receive data directly or indirectly indicating at least one of intraorbital pressure, ICP, IOP, or a relationship between ICP and IOP, and based on processing the received data as a feedback control variable, controlling the pump to adjust the fluid pressure within the one or more cavities, the controlling including using further monitoring of the received data to control the pump.

Example 2 can include, or can optionally be combined with the subject matter of Example 1, to optionally include a data interface attached to the control circuit to receive data directly indicating at least one of intraorbital pressure, ICP, IOP, or a relationship between ICP and IOP, the received data including an indication of at least one of, a sensed IOP sensed by a pressure sensor previously placed within an intraocular space of the eye, a sensed ICP sensed by a sensor previously placed in fluid communication with a cerebrospinal region, or a sensed intraorbital pressure sensed by a sensor previously placed in fluid communication with the orbit of the skull.

Example 3 can include, or can optionally be combined with the subject matter of Example 1 or 2 to optionally include the control circuit data interface to receive data indirectly indicating at least one of intraorbital pressure, ICP, IOP, or a relationship between ICP and IOP, the received data including an indication of at least one of an eye blood vessel characteristic, a translaminar pressure difference including a cup-to-disc relationship, a systemic blood pressure, a body parameter including a body mass index (BMI), a differential hydrostatic pressure corresponding to different postural positions or orientations, a spontaneous venous pulsation or an induced venous pulsation, a laminar cribrosa shape or position, an episcleral venous pressure, or an orbital pressure.

Example 4 can include, or can optionally be combined with the subject matter of Examples 1-3 to optionally include a visualization assistance device to visualize a portion of the eye at different fluid pressures within the enclosure to monitor an indication of ICP.

Example 5 can include, or can optionally be combined with the subject matter of Examples 1-4 to optionally include a visualization assistance device wherein the visualization assistance device is configured to obtain an indication of cup-to-disc ratio.

Example 6 can include, or can optionally be combined with the subject matter of Examples 1-5 to optionally include a visualization assistance device to provide at least some of the data, wherein the visualization assistance device includes a fundus camera.

Example 7 can include, or can optionally be combined with the subject matter of Examples 1-6 to optionally include a visualization assistance device to provide at least some of the data, wherein the imaging device includes an optical coherence tomography (OCT) system.

Example 8 can include, or can optionally be combined with the subject matter of Examples 1-7 to optionally include a blood pressure sensor to provide at least some of the data.

Example 9 can include, or can optionally be combined with the subject matter of Examples 1-8 to optionally include a detector device to provide at least some of the data by detecting a change in at least one of a blood vessel dimension, flow characteristic, pulsation, oxygenation, or color characteristic.

Example 10 can include, or can optionally be combined with the subject matter of Examples 1-9 to optionally include a differential hydrostatic pressure sensor including an inclinometer or posture sensor to provide at least some of the data.

Example 11 can include, or can optionally be combined with the subject matter of Examples 1-10 to optionally include a tonometer to provide at least some of the data, the tonometer being integrated with or coupled to the enclosure to provide access of the tonometer to the eye.

Example 12 can include, or can optionally be combined with the subject matter of Examples 1-11 to optionally include a contact lens to provide at least some of the data, wherein the contact lens includes an integrated strain or other sensor to detect an eye characteristic.

Example 13 can include, or can optionally be combined with the subject matter of Examples 1-12 to optionally include an axonal transport imaging device to provide at least some of the data.

Example 14 can include, or can optionally be combined with the subject matter of Examples 1-13 to optionally include a laminar cribrosa position or shape detection device to provide at least some of the data.

Example 15 can include, or can optionally be combined with the subject matter of Examples 1-14 to optionally include wherein the data interface is to receive and process an indication of ICP obtained by performing a first visualization of a patient eye at a first fluid pressure within an goggle enclosure sized and shaped to be located over the patient eye without contacting the patient eye, the visualization carried out with the goggle enclosure located over the patient eye, performing one or more subsequent visualizations of the patient eye at one or more subsequent fluid pressures within the goggle enclosure, the visualization carried out with the goggle enclosure located over the patient eye, the subsequent fluid pressures different from the first fluid pressure, and using the first and subsequent visualizations, determining a change in at least one eye characteristic corresponding to the change between the first and subsequent fluid pressures within the enclosure.

Example 16 can include or use subject matter, such as an apparatus for at least one of diagnosing or treating an eye condition. The subject matter can comprise a goggle enclosure, sized and shaped to be seated on an eye socket of an eye to provide one or more cavities within the enclosure that extend about an entire exposed anterior portion of the eye, a pump, in fluidic communication with the one or more cavities to apply a fluid pressure to the one or more cavities, the pump configured to adjust a fluid pressure within the one or more cavities of the goggle enclosure, and a visualization assistance device, in communication with the pump, for visualizing at least a portion of the patient eye when the goggle enclosure is seated against the patient for the pump to adjust the fluid pressure within the cavity of the goggle enclosure.

Example 17 can include, or can optionally be combined with the subject matter of Example 16, to optionally include a control circuit, controlling the pump to adjust the fluid pressure within the one or more cavities for visualizing using the visualization assistance device at one or more fluid pressures within the one or more cavities of the goggle enclosure.

Example 18 can include, or can optionally be combined with the subject matter of Example 16 or 17 to optionally include wherein the control circuit is configured to control the pump to adjust the fluid pressure within the one or more cavities for visualizing using the visualization assistance device at one or more fluid pressures within the one or more cavities of the goggle enclosure, including for performing a first visualization of a patient eye at a first fluid pressure within the one or more cavities of the goggle enclosure, performing one or more subsequent visualizations of the patient eye at one or more subsequent fluid pressures within the goggle enclosure, the visualization carried out with the goggle enclosure located over the patient eye, the subsequent fluid pressures different from the first fluid pressure, and using the first and subsequent visualizations, determining a change in at least one eye characteristic corresponding to the change between the first and subsequent fluid pressures within the enclosure.

Example 19 can include, or can optionally be combined with the subject matter of Examples 16-18 to optionally include wherein the visualization assistance device includes an optical coherence tomography (OCT) device.

Example 20 can include, or can optionally be combined with the subject matter of Examples 16-19 to optionally include wherein the visualization assistance device includes a fundus camera.

Example 21 can include, or can optionally be combined with the subject matter of Examples 16-20 to optionally include wherein the visualization assistance device includes an ultrasound imaging device.

Example 22 can include, or can optionally be combined with the subject matter of Examples 16-21 to optionally include wherein the visualization assistance device includes or is coupled to an image processor circuit to analyze the first and subsequent visualizations to determine a change in at least one eye or other physiologic characteristic between the first and subsequent visualizations.

Example 23 can include, or can optionally be combined with the subject matter of Examples 16-22 to optionally include wherein the image processor circuit is configured to compare pixels or voxels associated with an image of a blood vessel to determine a change in blood flow velocity between the first and subsequent visualizations at different applied pressures within the one or more cavities of the enclosure.

Example 24 can include, or can optionally be combined with the subject matter of Examples 16-23 to optionally include wherein the image processor circuit is configured to compare pixels or voxels associated with an image of a blood vessel to determine a change in a color characteristic associated with a blood vessel between the first and subsequent visualizations at different applied pressures within the one or more cavities of the enclosure.

Example 25 can include, or can optionally be combined with the subject matter of Examples 16-24 to optionally include wherein the image processor circuit is configured to determine whether a change in an eye or other physiological characteristic between the first and subsequent visualizations indicates whether a specified blood vessel caliber change or other specified criterion has been met.

Example 26 can include, or can optionally be combined with the subject matter of Examples 16-25 to optionally include wherein the image processor circuit is configured to determine an indication of an intrabody pressure based upon a change in an eye or other physiological characteristic between the first and subsequent visualizations at different applied pressures within the one or more cavities of the enclosure.

Example 27 can include, or can optionally be combined with the subject matter of Examples 16-26 to optionally include wherein the image processor circuit is configured to correlate a cerebrospinal fluid (CSF) pressure to the indication of intrabody pressure based upon a change in an eye or other physiological characteristic between the first and subsequent visualizations at different applied pressures within the one or more cavities of the enclosure.

Example 28 can include, or can optionally be combined with the subject matter of Examples 16-27 to optionally include wherein the visualization assistance device includes or is coupled to an image processor circuit to analyze the first and subsequent visualizations to determine a change in at least one eye or other physiologic characteristic between the first and subsequent visualizations, wherein the at least one eye or other physiologic characteristic includes at least one amplitude, blood vessel caliber, location, or other characteristic of a spontaneous venous pulsation or induced venous pulsation.

Example 29 can include, or can optionally be combined with the subject matter of Examples 16-28 to optionally include wherein the control circuit is configured to operate the pump to adjust a fluid pressure within the one or more cavities of the goggle enclosure in correspondence with one or more portions of an ocular pulse cycle of the patient.

Example 30 can include, or can optionally be combined with the subject matter of Examples 16-29 to optionally include wherein the control circuit is configured to operate the pump to adjust a fluid pressure within the one or more cavities of the goggle enclosure in correspondence with one or more portions of an ocular pulse cycle of the patient.

Example 31 can include, or can optionally be combined with the subject matter of Examples 16-30 to optionally include wherein the control circuit is configured to operate the pump to adjust a fluid pressure within the one or more cavities of the goggle enclosure in correspondence with one or more portions of a cardiac cycle of the patient over a plurality of cardiac cycles of the patient so as to change (maximize, minimize, or neutralize) an amplitude or other characteristic of a spontaneous blood vessel pulsation, induced venous pulsation, or other eye or other physiologic characteristic over the plurality of cardiac cycles.

Example 32 can include, or can optionally be combined with the subject matter of Examples 16-31 to optionally include wherein the control circuit is configured to operate the pump to adjust a fluid pressure within the one or more cavities of the goggle enclosure in correspondence with one or more portions of an ocular pulse cycle of the patient over a plurality of ocular cycles of the patient so as to change an amplitude or other characteristic of a spontaneous blood vessel pulsation, induced venous pulsation, or other eye or other physiologic characteristic over the plurality of ocular pulse cycles.

Example 33 can include, or can optionally be combined with the subject matter of Examples 16-32 to optionally include wherein the control circuit is configured to operate the pump to adjust a fluid pressure within the one or more cavities of the goggle enclosure in correspondence with one or more portions of an intracranial pressure cycle of the patient over a plurality of intracranial pressure cycles of the patient so as to change an amplitude or other characteristic of a spontaneous blood vessel pulsation, induced venous pulsation, or other eye or other physiologic characteristic over the plurality of intracranial pressure cycles.

Example 34 can include, or can optionally be combined with the subject matter of Examples 16-33 to optionally include wherein the visualization assistance device includes or is coupled to an image processor circuit to analyze the first and one or more subsequent visualizations to determine an indication of an intrabody pressure based upon a change in at least one eye or other physiologic characteristic between the first and subsequent visualizations.

Example 35 can include or use subject matter, such as a method. The subject matter can comprise a method comprising, receiving data directly or indirectly indicating at least one of intracranial pressure (ICP), intraocular pressure (IOP), or a relationship between ICP and IOP, and based on the received data as a feedback control variable, controlling a pump to adjust a fluid pressure within an goggle enclosure sized and shaped to be located over the patient eye without contacting the patient eye, the controlling including using further monitoring of the received data to control the pump.

Example 36 can include, or can optionally be combined with the subject matter of Example 1, to optionally include wherein the receiving data includes receiving data directly indicating at least one of intraorbital pressure, ICP, IOP, or a relationship between ICP and IOP using an indication of at least one of a sensed IOP sensed by a fluid pressure sensor previously placed within an intraocular space of the eye, a sensed ICP sensed by a fluid pressure sensor previously placed in fluid communication with a cerebrospinal region, or a sensed intraorbital pressure sensed by a sensor previously placed in fluid communication with a cerebrospinal region.

Example 37 can include, or can optionally be combined with the subject matter of Example 35 or 36 to optionally include wherein the receiving data includes receiving data indirectly indicating at least one of intraorbital pressure, ICP, IOP, or a relationship between ICP and IOP, the received data including an indication of at least one of, an eye blood vessel characteristic, a translaminar pressure difference including a cup-to-disc relationship, a systemic blood pressure, a body parameter including body mass index (BMI), a differential hydrostatic pressure corresponding to different postural positions or orientations, a spontaneous venous pulsation or induced venous pulsation, a laminar cribrosa shape or position, an episcleral venous pressure, or an orbital pressure.

Example 38 can include, or can optionally be combined with the subject matter of Examples 35-37 to optionally include using a visualization assistance device to visualize a portion of the eye at different fluid pressures within the enclosure to monitor an indication of ICP.

Example 39 can include, or can optionally be combined with the subject matter of Examples 35-38 to optionally include using a visualization assistance device to obtain an indication of cup-to-disc ratio.

Example 40 can include, or can optionally be combined with the subject matter of Examples 35-39 to optionally include using a fundus camera as the visualization assistance device.

Example 41 can include, or can optionally be combined with the subject matter of Examples 35-40 to optionally include using an optical coherence tomography (OCT) system as the visualization assistance device.

Example 42 can include, or can optionally be combined with the subject matter of Examples 35-41 to optionally include using an indication of blood pressure data as at least some of the data.

Example 43 can include, or can optionally be combined with the subject matter of Examples 35-42 to optionally include using an indication of at least one of spontaneous venous pulsation data or induced venous pulsation data as at least some of the data.

Example 44 can include, or can optionally be combined with the subject matter of Examples 35-43 to optionally include providing at least some of the data by detecting a change in at least one of a blood vessel dimension, flow characteristic, pulsation, oxygenation, or color characteristic.

Example 45 can include, or can optionally be combined with the subject matter of Examples 35-44 to optionally include using information about the inclination or posture of the patient to provide at least some of the data.

Example 46 can include, or can optionally be combined with the subject matter of Examples 35-45 to optionally include using a tonometer to provide at least some of the data, the tonometer being integrated with or coupled to the enclosure to provide access of the tonometer to the eye.

Example 47 can include, or can optionally be combined with the subject matter of Examples 35-46 to optionally include using a contact lens to provide at least some of the data, wherein the contact lens includes an integrated strain or other sensor to detect an eye characteristic.

Example 48 can include, or can optionally be combined with the subject matter of Examples 35-47 to optionally include using information about axonal transport to provide at least some of the data.

Example 49 can include, or can optionally be combined with the subject matter of Examples 35-48 to optionally include using information about a laminar cribrosa position or shape to provide at least some of the data.

Example 50 can include, or can optionally be combined with the subject matter of Examples 35-49 to optionally include performing a first visualization of a patient eye at a first fluid pressure within an goggle enclosure sized and shaped to be located over the patient eye without contacting the patient eye, the visualization carried out with the goggle enclosure located over the patient eye, performing a one or more subsequent visualizations of the patient eye at a subsequent fluid pressure within the goggle enclosure, the visualization carried out with the goggle enclosure located over the patient eye, the subsequent fluid pressure different from the first fluid pressure, and using the first and subsequent visualizations, determining a change in at least one eye characteristic corresponding to the change between the first and subsequent fluid pressures within the enclosure.

Example 51 can include or use subject matter, such as a method. The subject matter can comprise performing a first visualization of a patient eye at a first fluid pressure within one or more cavities of an goggle enclosure sized and shaped to be located over the patient eye without contacting the patient eye, the visualization carried out with the goggle enclosure located over the patient eye, performing a subsequent visualization of the patient eye at the subsequent fluid pressure within one or more cavities of the goggle enclosure, the visualization carried out with the goggle enclosure located over the patient eye, the subsequent fluid pressure different from the first fluid pressure, and using the first and subsequent visualizations, determining a change in at least one eye or other physiologic characteristic corresponding to the change between the first and subsequent fluid pressures within the enclosure.

Example 52 can include, or can optionally be combined with the subject matter of Example 51, to optionally include wherein the visualization includes performing optical coherence tomography (OCT).

Example 53 can include, or can optionally be combined with the subject matter of Example 51 or 52 to optionally include wherein the visualization includes using a fundus camera.

Example 54 can include, or can optionally be combined with the subject matter of Examples 51-53 to optionally include wherein the visualization includes performing ultrasound imaging.

Example 55 can include, or can optionally be combined with the subject matter of Examples 51-54 to optionally include wherein the visualization includes analyzing the first and subsequent visualizations to determine a change in at least one eye or other physiologic characteristic between the first and subsequent visualizations.

Example 56 can include, or can optionally be combined with the subject matter of Examples 51-55 to optionally include wherein analyzing includes comparing pixels or voxels associated with an image of a blood vessel to determine a change in blood flow velocity between the first and subsequent visualizations at different applied pressures within the one or more cavities of the enclosure.

Example 57 can include, or can optionally be combined with the subject matter of Examples 51-56 to optionally include wherein analyzing includes comparing pixels or voxels associated with an image of a blood vessel to determine a change in a color characteristic associated with a blood vessel between the first and subsequent visualizations at different applied pressures within the one or more cavities of the enclosure.

Example 58 can include, or can optionally be combined with the subject matter of Examples 51-57 to optionally include wherein analyzing includes determining whether a change in an eye or other physiological characteristic between the first and subsequent visualizations indicates whether a specified blood vessel caliber change or other specified criterion has been met.

Example 59 can include, or can optionally be combined with the subject matter of Examples 51-58 to optionally include wherein analyzing includes determining an indication of an intrabody pressure based upon a change in an eye or other physiological characteristic between the first and subsequent visualizations at different applied pressures within the one or more cavities of the enclosure.

Example 60 can include, or can optionally be combined with the subject matter of Examples 51-59 to optionally include wherein analyzing includes correlating an intracranial pressure (ICP) to the indication of intrabody pressure based upon a change in an eye or other physiological characteristic between the first and subsequent visualizations at different applied pressures within the one or more cavities of the enclosure.

Example 61 can include, or can optionally be combined with the subject matter of Examples 51-60 to optionally include wherein analyzing includes using the first and subsequent visualizations to determine a change in at least one eye or other physiologic characteristic between the first and subsequent visualizations, wherein the at least one eye or other physiologic characteristic includes at least one amplitude, blood vessel caliber, location, or other characteristic of a spontaneous blood vessel pulsation or induced venous pulsation.

Example 62 can include, or can optionally be combined with the subject matter of Examples 51-61 to optionally include adjusting a fluid pressure within the one or more cavities of the goggle enclosure in correspondence with one or more portions of a cardiac cycle of the patient.

Example 63 can include, or can optionally be combined with the subject matter of Examples 51-62 to optionally include adjusting a fluid pressure within the cavity of the goggle enclosure in correspondence with one or more portions of an ocular pulse cycle of the patient.

Example 64 can include, or can optionally be combined with the subject matter of Examples 51-63 to optionally include adjusting a fluid pressure within the one or more cavities of the goggle enclosure in correspondence with one or more portions of a cardiac cycle of the patient over a plurality of cardiac cycles of the patient so as to maximize an amplitude or other characteristic of at least one of a spontaneous blood vessel pulsation, an induced venous pulsation, or other eye or other physiologic characteristic over the plurality of cardiac cycles.

Example 65 can include, or can optionally be combined with the subject matter of Examples 51-64 to optionally include analyzing the first and subsequent visualizations to determine an indication of an intrabody pressure based upon a change in at least one eye or other physiologic characteristic between the first and subsequent visualizations.

Example 66 can include or use subject matter, such as a method. The subject matter can comprise releasing a gauge pressure from an goggle enclosure sized and shaped to be located over a patient eye without contacting the patient eye, performing a visualization of the patient eye at an atmospheric fluid pressure within the goggle enclosure, the visualization carried out with the goggle enclosure located over the patient eye, to detect an eye characteristic achieving an eye characteristic rebound criterion, and applying a gauge pressure to the goggle enclosure to achieve an eye characteristic change criterion.

Example 67 can include, or can optionally be combined with the subject matter of Example 66, to optionally include wherein releasing a gauge pressure includes opening a controllable vent in fluid communication with the goggle enclosure.

Example 68 can include, or can optionally be combined with the subject matter of Example 66 or 67 to optionally include performing a first visualization of a patient eye at a gauge pressure within an goggle enclosure sized and shaped to be located over the patient eye without contacting the patient eye, the first visualization performed immediately prior to releasing the gauge pressure from the goggle assembly located over the patient eye, performing one or more subsequent visualizations of the patient eye, the one or more subsequent visualizations performed after releasing the gauge pressure from the goggle assembly located over the patient eye, and using the first and subsequent visualizations, determining the occurrence of an eye characteristic rebound criterion in at least one eye characteristic corresponding to the release of a gauge pressure from the goggle assembly.

The above description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Geometric terms, such as "parallel", "perpendicular", "round", or "square", are not intended to require absolute mathematical precision, unless the context indicates otherwise. Instead, such geometric terms allow for variations due to manufacturing or equivalent functions. For example, if an element is described as "round" or "generally round," a component that is not precisely circular (e.g., one that is slightly oblong or is a many-sided polygon) is still encompassed by this description.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in or in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The claimed invention is:

1. An apparatus for at least one of diagnosing or treating an eye condition in a patient, the apparatus comprising:
   a goggle enclosure, sized and shaped to be seated on an eye socket of an eye to provide one or more cavities within the enclosure that extend about an entire exposed anterior portion of the eye;
   a pressure source, in fluidic communication with the one or more cavities to apply a fluid pressure to the one or more cavities, the pressure source configured to adjust the fluid pressure within the one or more cavities of the goggle enclosure; and
   a control circuit including a data interface configured to receive data from a detector device, the detector device including at least one of:
   an optical signature sensor system,
   a blood pressure sensor system,
   an inclinometer sensor system,
   a contact pressure system,
   an MRI system, or
   an X-ray system, and
   wherein the control circuit is configured to control, using the received data as a feedback control variable, the pump to adjust the fluid pressure within the one or more cavities.

2. The apparatus of claim 1, wherein the detector device includes the inclinometer and at least one of a direct IOP sensor system, a tonometer, or a direct ICP sensor system.

3. The apparatus of claim 1, wherein the detector device includes an eye surface sensor system.

4. The apparatus of claim 1, wherein the detector device includes an eye surface sensor system system.

5. The apparatus of claim 1, wherein the detector device includes the inclinometer sensor system.

6. The apparatus of claim 1, wherein the detector device includes the contact pressure sensor system.

7. The apparatus of claim 1, wherein the detector device includes the MRI system.

8. The apparatus of claim 1, wherein the detector device includes the X-ray system.

9. The apparatus of claim 1, wherein the detector device includes an ultrasound system.

10. The apparatus of claim 1, wherein the detector device includes an OCT system.

11. The apparatus of claim 1, comprising an enclosure pressure sensor.

12. The apparatus of claim 1, wherein the detector device includes the blood pressure sensor system.

13. The apparatus of claim 1, wherein the detector device includes a color/intensity sensor system.

14. The apparatus of claim 1, wherein the detector device includes a camera system.

15. The apparatus of claim 5, wherein the inclinometer includes a tilt sensor.

16. The apparatus of claim 5, wherein the inclinometer includes an accelerometer.

17. The apparatus of claim 5, wherein the inclinometer is configured to indicate the relative position of the patient with respect to a local reference frame including at least one of a sagittal, a coronal, or a transverse plane associated with the patient.

18. The apparatus of claim 1, wherein the control circuit includes a processing unit to process the feedback control variable to control the pump to adjust fluid pressure in the one or more cavities toward a target eye parameter value based at least in part on the received data.

19. The apparatus of claim 18, wherein the target eye parameter includes a target IOP value.

20. The apparatus of claim 18, wherein the target eye parameter includes a target translaminar pressure difference (TPD) value.

21. A method of using an apparatus, the apparatus comprising a goggle enclosure, sized and shaped to be seated on an eye socket of an eye to provide one or more cavities within the enclosure that extend about an entire exposed anterior portion of the eye, a pressure source in fluidic communication with the one or more cavities to apply a fluid pressure to the one or more cavities, the pressure source configured to adjust the fluid pressure within the one or more cavities of the goggle enclosure, and a control circuit including a data interface configured to receive data from a detector device, the detector device including at least one of an optical signature sensor system, a blood pressure sensor system, an inclinometer sensor system, a contact pressure system, an MRI system, or an X-ray system, wherein the control circuit is configured to control, using the received data as a feedback control variable, the pump to adjust the fluid pressure within the one or more cavities, the method comprising:
   receiving data from the detector device; and
   adjusting the fluid pressure within the one or more cavities based at least in part on the received data from the detector device.

22. The method of claim 21, wherein receiving data includes receiving data from the inclinometer sensor and further receiving an indication of at least one of intracranial pressure (ICP), intraocular pressure (IOP), or a relationship between ICP and IOP.

23. The method of claim 21, wherein adjusting the fluid pressure includes adjusting the fluid pressure toward a target eye parameter value based at least in part on the received data.

24. The method of claim 23, wherein adjusting toward the target eye parameter value includes adjusting the fluid pressure toward a target IOP value.

25. The method of claim 23, wherein adjusting toward the target eye parameter value includes adjusting the fluid pressure toward a target translaminar pressure difference (TPD) value.

\* \* \* \* \*